US007941534B2

(12) United States Patent
de la Huerga

(10) Patent No.: US 7,941,534 B2
(45) Date of Patent: May 10, 2011

(54) SYSTEM AND METHOD TO AUTHENTICATE USERS TO COMPUTER SYSTEMS

(76) Inventor: Carlos de la Huerga, Milwaukee, WI (US)

( * ) Notice: Subject to any disclaimer, the term of this patent is extended or adjusted under 35 U.S.C. 154(b) by 1604 days.

(21) Appl. No.: 10/899,520

(22) Filed: Jul. 26, 2004

(65) Prior Publication Data

US 2005/0091338 A1 Apr. 28, 2005

Related U.S. Application Data

(63) Continuation-in-part of application No. 10/127,734, filed on Apr. 22, 2002, now Pat. No. 6,779,024, which is a continuation-in-part of application No. 09/170,169, filed on Oct. 13, 1998, now Pat. No. 6,408,330, which is a continuation-in-part of application No. 08/834,634, filed on Apr. 14, 1997, now Pat. No. 5,960,085.

(51) Int. Cl.
*G06F 13/00* (2006.01)

(52) U.S. Cl. ......... 709/225; 709/219; 709/227; 709/250

(58) Field of Classification Search .................. 709/217, 709/219, 223, 224, 225, 227, 228, 250
See application file for complete search history.

(56) References Cited

U.S. PATENT DOCUMENTS

| | | | | |
|---|---|---|---|---|
| 5,878,142 | A * | 3/1999 | Caputo et al. | 713/159 |
| 6,088,450 | A * | 7/2000 | Davis et al. | 713/182 |
| 6,181,803 | B1 * | 1/2001 | Davis | 382/115 |
| 6,381,631 | B1 * | 4/2002 | van Hoff | 709/202 |
| 6,910,136 | B1 * | 6/2005 | Wasserman et al. | 726/4 |
| 7,028,897 | B2 * | 4/2006 | Fernandes et al. | 235/449 |
| 7,324,972 | B1 * | 1/2008 | Oliver et al. | 705/40 |

OTHER PUBLICATIONS

Contextual Digital Assistant Model 1000, Product Data Sheet CN-PDCDA 1000 R1; Copyright Jan. 2002 CartaNova, Inc. ; 2 pages.

Contextual Digital Assistant Model 1000, Product Data Sheet CN-PDCDA 1000 R1; Copyright Feb. 2002 CartaNova, Inc. ; 4 pages.

* cited by examiner

*Primary Examiner* — Viet Vu
(74) *Attorney, Agent, or Firm* — Quarles & Brady

(57) ABSTRACT

A system utilizing a personal security device to provide access to a computer terminal where the personal security device includes circuitry and transceiver components for transmitting identification information and exchanging other digital information with a computer terminal and other compatible devices and the personal security device establishes a communication link with a computer terminal to allow a user to logon to the terminal so that when a user leaves the computer terminal, the communication link is terminated, causing the computer terminal to lock the keyboard, blank the monitor, and/or logoff the user if the communication link is not restored within a sufficient time period and also allowing the personal security device to facilitate subsequent computer access within a time range by providing time related access codes to the terminal that can be used to reestablish computer terminal access.

47 Claims, 54 Drawing Sheets

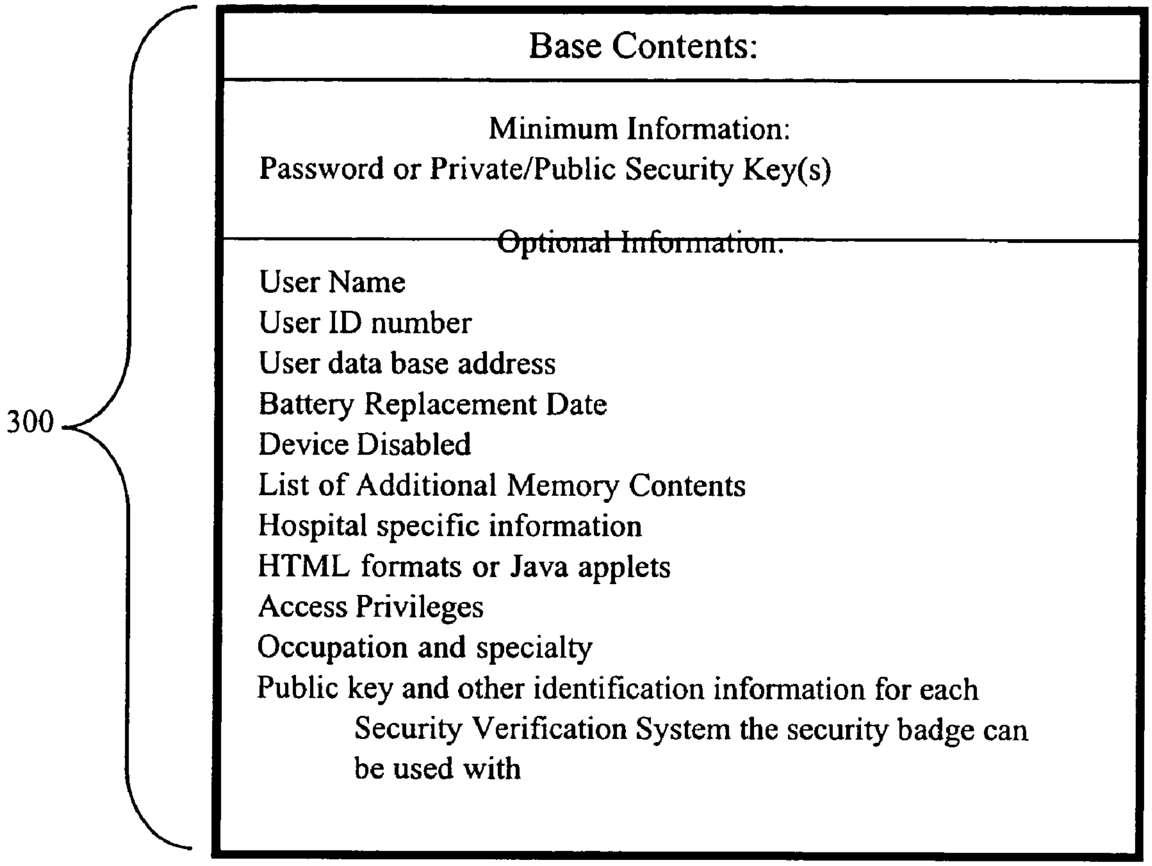

Figure 8

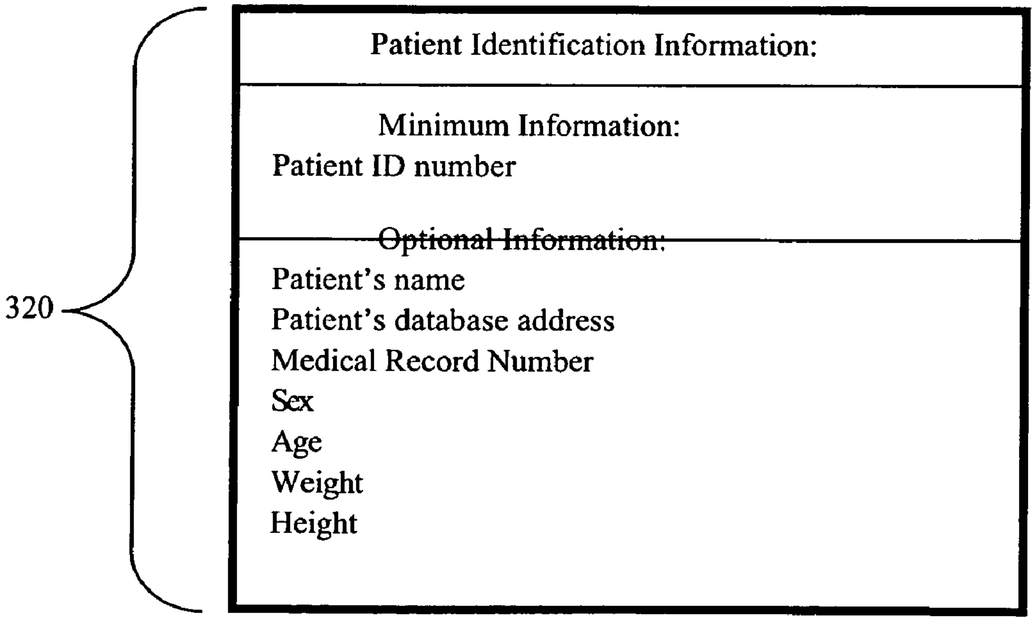

| Base Contents: |
|---|
| Minimum Information:<br>Password or Private/Public Security Key(s) |
| Optional Information:<br>User Name<br>User ID number<br>User data base address<br>Battery Replacement Date<br>Device Disabled<br>List of Additional Memory Contents<br>Hospital specific information<br>HTML formats or Java applets<br>Access Privileges<br>Occupation and specialty<br>Public key and other identification information for each<br>        Security Verification System the security badge can<br>        be used with |

320 — {

| Patient Identification Information: |
|---|
| Minimum Information:<br>Patient ID number |
| Optional Information:<br>Patient's name<br>Patient's database address<br>Medical Record Number<br>Sex<br>Age<br>Weight<br>Height |

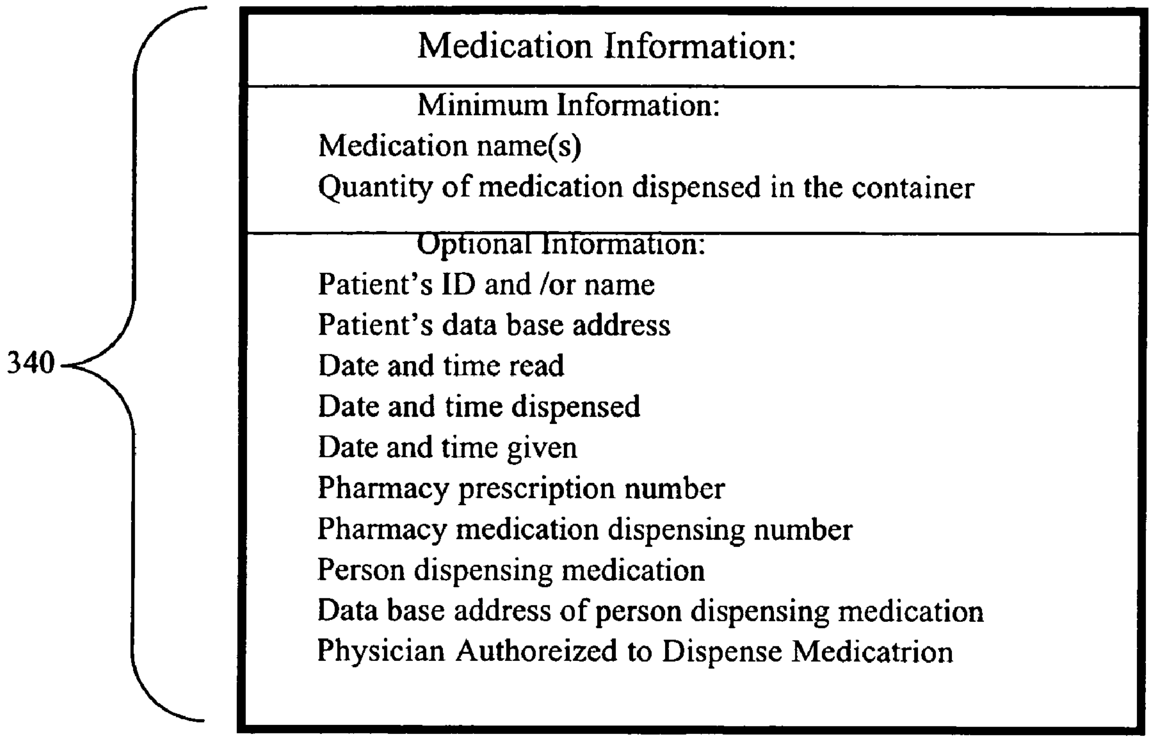

Figure 10

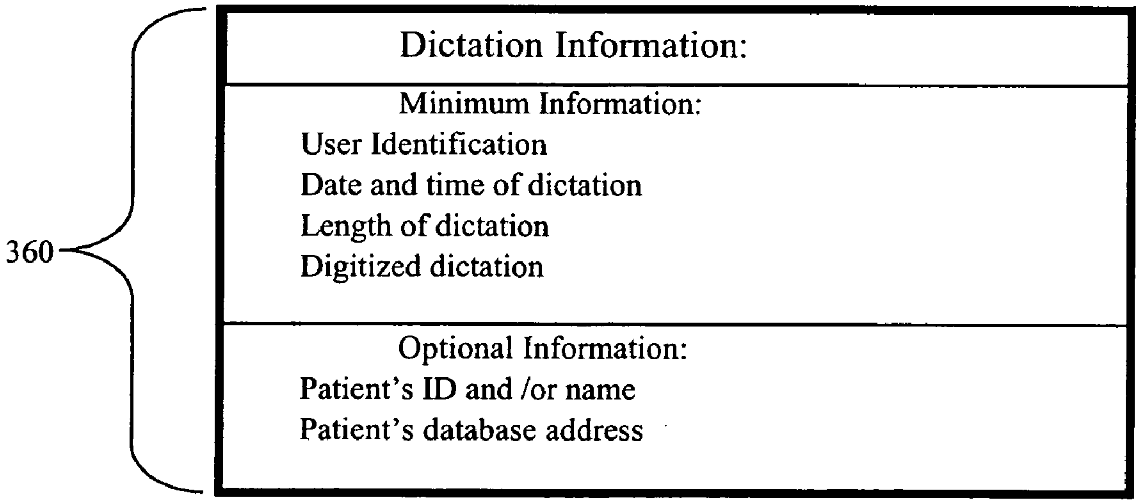

Figure 11

| Medication Information: |
|---|
| Minimum Information:<br>Medication name(s)<br>Quantity of medication dispensed in the container |
| Optional Information:<br>Patient's ID and /or name<br>Patient's data base address<br>Date and time read<br>Date and time dispensed<br>Date and time given<br>Pharmacy prescription number<br>Pharmacy medication dispensing number<br>Person dispensing medication<br>Data base address of person dispensing medication<br>Physician Authoreized to Dispense Medicatrion |

340

| Dictation Information: |
|---|
| Minimum Information:<br>User Identification<br>Date and time of dictation<br>Length of dictation<br>Digitized dictation |
| Optional Information:<br>Patient's ID and /or name<br>Patient's database address |

360

```
<html>

<head>
<title>Medication Administration</title>
</head>

<form action="http://hww.st_mary.springfield/medication/given/987654321/
19_May_1996/13:42" method=put>

<a href="http://hww.st._mary.springfield/demographics/987654321/19_May_1996">
ID: 987654321</a><br>

Report type: Medication Administration<br>
Patient ID Verified: YES
<br><br>

<table border=2 cellspacing=5>
<tr><td colspan=3 align=center>Medication Given:</td></tr>

<tr><td>Penicillin</td><td>100mg</td><td>
<select name=Penicillin>
<option>2
<option>1.5
<option>1
<option>0.5
<option>none
</select> capsules</td></tr>

<tr><td>Tylenol w/Codeine</td><td>200mg</td><td>
<select name=Tylenol_w/Codeine>
<option>1
<option>0.5
<option>none
</select>  capsule</td></tr>

</table>
<br>

Given by:
<a href="http://hww.st._mary.springfield/staff_directory/M_T_Adamson.html">
 Mary T. Adamson, R.N.</a>,   at: 13:49 19-May-1996<br>

Dispensed by:
<a href="http://hww.st._mary.springfield/staff_directory/S_W_Johnson.html">
 Sam W. Johnston, R.N.</a>,   at: 13:42 19-May-1996<br>
<br>
ID Device Serial Number: 1265338<br>
```

```
<input type=hidden name=Pat.I.D. value=987654321>
<input type=hidden name=Pat.I.D.Addr
                value="http://hww.st._mary.springfield/demographics/987654321/
19_May_1996">
<input type=hidden name=Date value=13:59 19-May-1996>
<input type=hidden name=Report_type value=Medication_Administration>
<input type=hidden name=Patient_ID Verified value=YES>
<input type=hidden name=Med1 value=Penicillin-100mg-2_capsules>
<input type=hidden name=Med2 value=Tylenol_w/Codeine-200mg-1_capsule>
<input type=hidden name=Given_by
value=http://"hww.st._mary.springfield/staff_directory/M_T_Adamson.html"
_Mary_T._Adamson,_R.N-13:49_19-May-1996>
<input type=hidden name=Dispensed_by
value=http://"hww.st._mary.springfield/staff_directory/S_W_Johnson.html"
_Sam_W._Johnston,_R.N.-13:42_19-May-1996>
<input type=hidden name=ID_Device_Serial_Number value=1265338>

<br>
<input type=submit value=Approve&#information>

</html>
```

Figure 14B

SYSTEM AND METHOD TO AUTHENTICATE USERS TO COMPUTER SYSTEMS

CROSS-REFERENCE TO RELATED APPLICATIONS

This is a continuation in part of U.S. patent application Ser. No. 10/127,734 which was filed on Apr. 22, 2002 now U.S. Pat. No. 6,779,024 and is entitled "Data Collection Device System" and which was a continuation in part of U.S. patent application Ser. No. 09/170,169, filed Oct. 13, 1998, now U.S. Pat. No. 6,408,330 entitled "Remote Data Collecting And Address Providing Method And Apparatus" which issued on Jun. 18, 2002 and U.S. patent application Ser. No. 08/834,634, filed Apr. 14, 1997, now U.S. Pat. No. 5,960,085 entitled "Security Badge For Automated Access Control And Secure Data Gathering" which issued on Sep. 28, 1999. Each of the references is incorporated by reference.

STATEMENT REGARDING FEDERALLY SPONSORED RESEARCH OR DEVELOPMENT

Not applicable.

BACKGROUND OF THE INVENTION

The present invention relates to computer systems for the management of information distributed across a plurality of electronic system devices. More particularly, the invention relates to a system which includes a plurality of network servers, interface terminals, remote data collecting devices and other smart devices to facilitate information collection, approval, editing and storage such that the network server storage location of specific information can be specified using a remote collecting device. The invention also relates to record verification methods.

As an initial matter, in the interest of simplifying this explanation and unless indicated otherwise, the description which follows describes the invention in the context of a medical facility. However, it should be recognized that the invention should not be so limited and clearly has applications which are outside a medical facility, only some of which are specifically discussed hereinafter.

In many industries a need exists for remote information collection and information storage which facilitates easy subsequent information retrieval. For example, in medical facilities there is a need, for purposes of patient protection, quality control, record keeping, billing, and forensics, to monitor, control, and record access to medicine dispensation, medicine administration, IVs, blood transfusions, and other treatments as well as the collection, administration, and testing of blood and tissue samples. These events have traditionally been controlled and monitored manually by doctors, nurses and other facility personnel (hereinafter "physicians" generally).

Unfortunately the increasing specialization and complexity of medical care has vastly increased both the types and amount of routine record keeping that is required to track all events which occur in a facility. Advantageously, rapid growth of computer technologies has provided tools which can be used to store and retrieve specific information from a vast quantity of medical records. In particular, Internet technology is now routinely used to create hospital Intranets, link discrete hospital databases and make their data, images, and audio video records commonly accessible.

Most medical facility Intranet systems include a plurality of network servers disposed in either one central information systems department or at various locations throughout the facility, a plurality of computer terminals located throughout the facility and a data bus which links all of the servers and computers together. Software is loaded onto each computer to facilitate information entry and specify server addresses for information retrieval and storage.

The first Intranet systems were used for only very few applications and therefore were not extremely complex. However, over time, as Intranet applications became more numerous and their use as information management tools became more widely recognized, single server systems could no longer meet the information management needs of even a single medical facility. This information management capacity problem has been exacerbated by prolific mergers and acquisitions among medical groups such that many medical groups now have several locations and vast amounts of information to manage.

To facilitate information management on such a huge scale Intranet systems have evolved over time. In most cases, so as to increase management capability without wasting existing capability (i.e. without completely replacing existing servers and computers), instead of replacing entire Intranet systems, additional servers and computers are simply added to an existing Intranet network.

While this piecemeal approach to Intranet enhancement minimizes hardware costs, this approach results in an extremely complex system wherein it is often relatively difficult to direct information to known electronic memory locations (i.e. server storage addresses) which are later easily accessible. While such storage addresses could be manually provided, providing such addresses manually is particularly cumbersome as many addresses are complex and difficult to specify. This is because a single facility or related facilities may employ many different servers and each server may have access to several different memory devices. Addressing schemes have been further exacerbated by the Internet where there may be several thousand servers and it would be impractical for a user to attempt to manually enter every server address used for storage.

To overcome the addressing problem most Intranet servers are equipped to automatically assign server addresses to specific types of user provided information. To this end, a browser is typically loaded onto each Intranet capable computer which communicates with system servers. When a user contacts a server to interact therewith (i.e. to provide information thereto or receive information therefrom), the server sends instructions to the browser indicating what should be displayed on the computer screen. Typically the screen indicates the server which originated the browser instructions, includes hyperlinks to various related server addresses, includes some instructions on how to use the server via the browser and provides blanks for entering information which is to be returned to the server for storage or processing.

In addition the server provides addresses to displayed hyperlinks and for information which is to be entered by a user. Typically the server provided addresses are held in computer memory and not displayed. After the physician indicates that information has been entered or selects a hyperlink, the browser software transmits the information to the server or contacts the server indicated by the hyperlink address.

Where information is sent to a server, when the server receives information the server may do any of a number of different things including storing the information at a server address or some type of processing and sending additional instructions to the browser. Where a user selects a hyperlink the server indicated by the hyperlink address responds to the selection by providing a different set of browser instructions for configuring the browser screen.

For example, in the hospital environment a first browser screen might display several user selectable hyperlinks for entering different types of information into the system and no blanks for entering information. For instance, a first hyperlink may be to a pharmacy server to request a screen presentation to enter pharmacy information, a second link may be to a billing server, a third link may be to a patient history server and a fourth link might be to a prescription server. In this case, to enter information the user first has to select one of the hyperlinks.

When a hyperlink is selected, the server indicated by the hyperlink address provides instructions to the browser for configuring the browser screen. For example, a server used by a pharmacy may provide instructions to configure a screen including, along with instructions for filling in blanks, a first blank for entry of a patient's name, a second blank for entry of a physician's name, a third blank for entry of a dispensed drug and a quantity indicator and a fourth blank for entry of the dispensing date and time.

After a physician indicates that required information has been provided, the browser transmits the information to the pharmacy server. When the server receives the information the server stores or processes the information and then typically returns a message indicating that the information has been stored or processed.

After a pharmacy-record has been stored, when a pharmacist reviews records on the pharmacy server the pharmacist can verify, among other things, that a specific prescription was dispensed, the date and time of dispensing, which patient received the prescription and which physician dispensed the prescription.

To enter some other type of information such as billing information, using the first screen, a physician might select a second billing server hyperlink. When the second hyperlink is selected, the billing server provides screen configuration instructions and a return target address for information to be returned to the server for storage. The browser displays the billing input screen and waits for the physician to indicate that information has been provided. Thereafter the provided information is transmitted to the server at the target address and is either stored or processed. In this manner all information addressing and control is facilitated by the servers, not the system user.

While such information receiving and addressing systems can meet the information gathering needs of some facilities, such systems have a number of shortcomings. First, information gathering and entry into such a system is extremely time consuming and therefore is often thought of as an onerous task which is to be avoided. For example, in a medical facility, when a physician makes her rounds, the physician may visit with twenty or more patients, performing examinations and procedures, diagnosing illnesses and prescribing and administering drugs. Each visit requires information gathering related to symptoms, diagnosis, prescription, procedures and examinations performed and drugs prescribed and administered. When this information is gathered via a pen and clip board, the information must later be entered into the system and stored at a specific and accessible location, Most physicians are not particularly adept at data entry. In addition, most physicians are extremely busy and therefore do not have the time to personally enter written information into a system via a browser. For these reasons either information is never entered into a system or a person specifically earmarked for data entry is required. While a data entry person may be expensive, the alternative (i.e. not entering the information into a searchable form) is not acceptable as information must be properly archived.

Second, even where a data entry person is provided, under the press of time many physician's have developed their own, personalized shorthand to expedite note taking during patient visits. In addition, often physician's writing styles are very different making it difficult at best to decipher hand written records during data entry. Shorthand and sloppy or varying writing styles make data entry by someone other than a physician extremely difficult.

Third, when information is entered into a system manually by someone other than a physician, the likelihood of mistakes is extremely high due to imperfect translation of handwritten notes, the fact that entry personnel typically are not trained in medical terminology and the fact that many medical terms are very similar, thereby increasing the likelihood that one term may be substituted for another.

Fourth, because tolerance for errors in medical records is extremely low, there should be some way to force physicians to check the accuracy of system records prior to allowing permanent storage. The present server/browser systems do not require physician approval of records prior to storage. In other words, in many cases a data entry person may enter a physician's notes and the physician may never check the notes for accuracy.

Fifth, even when someone other than a physician enters information into a system and a physician intends to revisit the information prior to permanent storage to check accuracy, despite the importance of record review, because of the press of time, record review by physicians is typically low on a physician's priority list. Where a physician allows even a few days to pass prior to reviewing information for approval, a physician's recollection of what transpired during a patient visit may not be accurate and information errors may result.

Sixth, even where a physician takes on the task of entering all information into a system to ensure quality control, the task of moving about from one browser screen to another to input information which is directed to correct server storage locations is onerous where many different records have to be entered and stored. For example, a physician may collect twenty different records while making rounds. Five of the records may have to be stored in patient record's on a patient history server, five records may have to be stored on a pharmacy server, five records may have to be stored on a billing server and the remaining five records may have to be stored on an inventory server. In this case, the physician would have to jump from one browser screen to another during data entry to enter the twenty records into the system. While this simple task might not be objectionable where there are only a few records, clearly, as the number of records which a physician is expected to make increase, the task of jumping among different browser screens becomes more taxing.

Seventh, in many cases some information may have to be provided to many different servers and therefore might have to be entered by a physician or a data entry person more than once. For example, where a drug is prescribed for a patient drug dispensation and administration information may have to be provided to many different servers for different purposes. A pharmacy server may require an administration record to ensure that a drug has been delivered, a billing server may require a record of dispensation for billing purposes, a patient record server may have to be updated to indicate that the drug was received, when the drug was received, the quantity of the drug received, the physician who administered the drug and so on, an inventory server may require an administration record to update an inventory list and automatically order drugs to meet anticipated requirements, etc. To provide all of these records to all of the servers, a physician would have to access four different browser screens, a separate browser screen for each server, and duplicative information would have to be entered to be delivered to each server.

Eighth, typical systems do not make any record of who approved information entered into a system and therefore there is no way to determine if an authorized physician approved a record or some clerical personnel accidentally approved a record before storage.

Various electronic devices have been developed to aid in the information gathering task. One handy information gathering device is the dictation device (DD) which can be used to record a physician's audio (i.e. voice) notes during a patient visit. To this end, a typical DD includes a processor, a memory (typically an electronic memory), a microphone, a speaker and some type of activation button. To take audio notes a physician positions the activation button in a record position and speaks into the microphone, the processor recording all voice notes in the memory. DDs often also allow audio review of oral notes and re-recording features to correct mistakes.

In facilities where physicians regularly use DDs, recorded notes are provided to data entry personnel who manually type audio records into an Intranet computer terminal for storage on a server. In the alternative, recently some software has been developed which can automatically convert audio records into text files for digital storage.

While DDs are preferred by some physicians, DDs do not overcome many of the shortcomings of manual (i.e. pen and paper) record keeping which are discussed above. For example, unless a system includes voice recognition software, data entry personnel are still required, physician shorthand causes transcription problems for both a data entry person and transcription software, mistakes may be made during transcription due to imperfect dictation and complex medical terminology, there is no procedure to ensure that information accuracy is checked or to indicate who approved information prior to permanent storage and it takes a large amount of time to enter information into the system.

Another handy information gathering device is a hand held device (HHD) which streamlines the information gathering process and the process of entering information into an Intranet system. To this end, a typical HHD may include a keyboard or the like, a processor, a memory and a transmitter. The board takes the place of a conventional clip board and is used to manually and remotely enter information which the processor stores in the memory. After information has been entered via an HHD, to provide the information to the system, the HHD transmitter is positioned in close proximity to a computer input device and the information is transmitted to the input device via a message including a series of signals.

To intelligibly receive a transmitted message and provide information contained therein to a browser for ultimate delivery to a server for storage or processing, a message receiving computer must be capable of translating the transmitted message into the language used by the server which is typically the hypertext markup language (HTML). This task is accomplished in one of two ways. First, the input device may include special dedicated hardware which converts the message into HTML, the hardware resembling a disk drive in the way it interacts with a browser. Second, the input device may simply provide the received message to the computer processor and software loaded onto the processor might be designed to translate the message into HTML.

Thus, HHDs can be used to eliminate physician's hand written notes thereby streamlining the data gathering/entry process. In addition, as a physician enters information into an HHD, the physician can approve entered information immediately eliminating the need to later revisit the information for approval.

While HHD technology goes a long way to solving many of the problems associated with remote information gathering, problems still exist. First, it is likely that physicians will object to having to manually enter information into an HHD for the same reasons that physicians object to entering information into regular computer terminals. In addition, with an HHD information entry is even more objectionable because most HHD keyboards are relatively small.

Second, patient's will likely object when they perceive that a physician's time during a visit is split between the patient and an HHD for information entry. This is particularly true in the case where it might be difficult to enter information into the HHD thereby requiring additional data entry time.

Third, even if there were some quick way to enter information into an HHD, transmission of the information from the HHD to a browser and ultimately to a server for storage or processing is a relatively complex task. For example, assuming five records are stored in an HHD for transmission to a browser and that each of the five records is different such that each record ultimately has to be stored on a different server. In this case, prior to transmitting each record to the browser, the physician would have to select the proper browser screen for data transmission. For example, if the first record is to be stored on a pharmacy server, the physician has to select the pharmacy browser screen prior to transmitting the first record. After the first record is transmitted to the browser the browser then provides the record to the pharmacy server which is associated with the screen. Next, assuming the second record is to be stored on the a billing server, the physician has to select the billing browser screen prior to transmitting the second record. After the second record is transmitted the browser provides the record to the billing server. Not only is this process cumbersome, but the HHD would have to have some mechanism which indicated to the physician which record is queued up for transmission so that the physician could select the proper browser screen and associated server address.

Fourth, conventional HHDs do not indicate who approved a record for ultimate storage.

Fifth, again, where duplicative information must be provided to several different servers, a physician has to separately select a browser screen associated with each server and transmit the information to be stored once for each server which is to receive the information. This is time consuming and therefore objectionable.

Some HHDs have been designed to facilitate a pseudo-addressing scheme whereby an ultimate server target address can be selected for some specific types of HHD information. For example, some HHDs allow a user to enter an E-mail address for a message to be delivered via an Intranet or Internet system.

At first blush an HHD which specifies a pseudo-address appears to overcome many of the problems associated with transferring information from an HHD to a server for ultimate storage. Thus, if server addresses can be specified, a single generic browser screen can be used as an intermediary between an HHD and servers, the HHD, not the servers, specifying where HHD information should ultimately be delivered for storage or processing.

Unfortunately, instead of simplifying the information management task, pseudo-address specifying HHDs add a new wrinkle of complexity to a browser system. To this end, while existing address specifying HHDs can provide both information (i.e. a message in the case of E-mail) and an ultimate target address, a dedicated "clearing house" server is required for a number of purposes. First, because the HHD cannot specify configuration of a browser screen, a clearing house server is required for screen configuration.

Second, because Intranet addresses are often extremely complex and difficult to manually specify, to simplify address specification, HHD provided addresses usually take a short hand form which in and of itself cannot be used by a browser to direct information to a specific server. The short hand address is provided to the clearing house server via the browser. Thereafter, the clearing house server uses the short hand address to formulate a more detailed target address specifying a different server for message delivery. Thus, the clearing house server must have some clearing house software for processing received information.

Third, in addition to providing browser screen configuration information, the clearing house server also has to specify the clearing house server address so that HHD information and the short hand target address are provided to the clearing house server for further distribution.

In short, even where an HHD can provide a pseudo-address for targeting information, a dedicated clearing house server with special processing software is required.

To appreciate the added wrinkle of complexity in systems which facilitate pseudo-address specification, consider an exemplary system including HHDs which can specify E-mail messages and associated pseudo-addresses. In this case, to provide an E-mail message to an Intranet, an HHD user must first select an E-mail browser screen via a computer. When the E-mail screen is selected, the computer communicates with an associated E-mail server which provides information to the browser including screen configuration information and the E-mail server address. The browser thereafter displays a properly configured screen for receiving information from the HHD.

Next, the HHD user positions the HHD in close proximity to a computer input device and transmits the E-mail message, including E-mail address, to the browser. The device provides the message and E-mail address to the browser which in turn transmits the message and E-mail address to the E-mail server specified by the server address associated with the screen. When the E-mail server receives the message and E-mail address, the E-mail server uses the E-mail address to form a relatively more complex address specifying the target for the E-mail message and then transmits the E-mail message to the more complex address and intended recipient. Clearly this system is more complex than a typical Intranet system as a dedicated clearing house server is required for both screen configuration and additional processing.

One advantage of conventional paper type reporting systems is that original documents can be authenticated simply via a personal signature. Thus, to determine authenticity an original document can be located and a signature examined.

Unfortunately, often original documents cannot be located for authentication. Because copies are easy to manipulate (e.g. signature cut and paste and general information modification), document copies usually cannot be relied upon for verification of their content. Usually, the only reason copies are relied upon is because original documents cannot be retrieved.

Document authentication problems are further exacerbated in the digital realm as document modification and signature picture cutting and pasting is relatively easy using standard computer functions. Thus, for example, where a document is transmitted from one computer to another and includes some type of signature picture, it would be advantageous to have some way to authenticate the content of the received document.

One solution to this authentication problem is described in U.S. Pat. No. 5,689,567 (the "'567 patent") which is entitled "Electronic Signature Method and Apparatus," which issued on Nov. 18, 1997. In the '567 patent, to enable document authentication of a digitally stored document which is subsequently accessed, prior to storing the document, a digital signature picture is encrypted as a function of the document content and is further encrypted as a function of a private (i.e. secret) key. The encrypted signature picture and document are stored.

Thereafter, when the document is reaccessed, the signature picture is decrypted using a public key and as a function of the document content thereby generating the document including a signature picture. Where the document is authentic, the resulting signature picture matches the original signature picture. Authentication is performed by visually comparing the resulting signature picture to the original signature picture.

While the '567 patent invention is useful, the '567 invention has a number of shortcomings. First, after a document is retrieved and decrypted, often it will be useful to store the document in a more accessible form such as in the form of a conventional word processor document, spread sheet, etc. In this case, after the initial decryption, there is essentially no way to subsequently authenticate a document. Thus, for instance, after a word processor document is generated and stored in decrypted or plain text form, the document may not again be accessed for a long time (e.g. years). The next time the document is accessed, because of the passage of time, it may be desirable to re-authenticate. The '567 reference does not facilitate re-authentication.

Second, it is often advantageous to generate a hard copy (i.e. paper) of a digital document for more conventional storage or conveyance to another party. Again, the '567 patent facilitates a first authentication by visual comparison but thereafter authentication is impossible. For example, after a paper document with a digital signature picture is generated, the paper document may be stored in a conventional binder-type file for a long time (e.g. 5 years). Thereafter, the paper document may be retrieved for review. When retrieved there is no way to authenticate the document. This problem is exacerbated by the fact that many documents are copied and copies of documents are copied and, as with an original paper document which is digitally signed there is no way to authenticate a copy.

Thus, it would be advantageous to have an information gathering system for remotely gathering information, reviewing and approving information, identifying who generated information and identifying who approved information prior to storing the information. In addition, it would be advantageous if such a system facilitated easy downloading of the information from an information gathering device to a browser for ultimate transmission to a server for storage or processing. Moreover, it would be advantageous if such a system could be used with a conventional Intranet and did not require a dedicated clearing house server or specialized server software. Furthermore, it would be advantageous to have a system which can authenticate either a hard copy or a digitally stored document by simply analyzing information provided on the document.

Many devices and software programs have been developed to improve the security of computers and computer networks. Securing computers and networks is essential to protect confidential information, to prevent fraud, and to ensure that computers are not compromised by amateur hackers for their entertainment or by terrorists intent on disrupting or endangering public safety.

The public has seen the effects of insecure computer systems in recent years including the mass release of customer credit card numbers, the use of computers by hackers to launch denial of service attacks, and outright theft from e-commerce sites. These and other events threaten to undermine the public's interest in using computers for conducting a variety of online business activities referred to as e-commerce.

Today and for the last thirty years the most prevalent form of security is the use of software to request from a person who wants to use a computer his user name and password. This information is typically sent to a remote security server, which uses the unique user name to look up the corresponding password for that person. Then the entered password is compared with the stored password, when there is a match the person is grated access to the computer, if not they are denied access.

Unfortunately, user name and password schemes can often be overcome by hackers attempting to guess common passwords, e.g. "xxx", "123", blanks spaces, and the default password for many systems "password". In an attempt to fortify passwords, computer users are sometimes required to use long password strings (e.g. at least 8 characters), to use passwords that combine letters with numbers and/or punctuation marks, to change their password every month or so, and to prevent the reuse of a prior password for a year or longer. However, the security improvements are often illusionary; as password get longer, more complicated, or change frequently users tend to write them down, as they can't remember them. The users then leave the written password in a place that is all to often easily found, e.g. taped to the underside of keyboard, in their desk drawer, or other common location.

Another problem with complicated or changing passwords is that users who do not write them down frequently forget them. This results in their not being able to use their computers, which forces them to call the computer system help desk for assistance in recalling their password or resetting their password to allow the user to enter another new complicated password, which they probably will also forget or write down. The user now can continue to work, but the computer help desk staff is thus conditioned to expect a large number of users to forget their passwords. This allows a hacker or other person to attempt to impersonate one of the computer users to gain password information, after all the help desk cannot really verify the identity of the person calling by telephone.

Passwords are also disliked by those users who need to use computers for very short periods throughout the day, forcing them to enter the user name and password (e.g. this may require 15 seconds) in order to view one value or measurement (e.g. this may only take 3 seconds) and then log off. Nurses, physicians, and many factory workers have this problem; effectively spending more time logging on and off of a computer than the time they spend using it. Furthermore for very busy environments, the constant authentication and reauthentication of users can create a drain on network bandwidth and strain the security server.

Once the user has properly entered a password he is typically admonished to logout when leaving the workstation environment to prevent unauthorized access. The system may automatically log a user off after a predetermined period of inactivity. For users who must access the system frequently but intermittently, short inactivity periods for automatic logout will be a source of constant inconvenience. Alternatively, if long inactivity periods are used, another user may inadvertently use the terminal under the previous person's security authorization.

To improve the security of computer systems a number of other technologies have been developed, but are they used in relatively low numbers. One of the most common technologies includes the use of a biometric indicia (fingerprint, iris image, voice, facial image, etc.) that is measured or sensed and sent to a remote security server. The server compares the indicia against a database of indicia for registered users. To speed the process up and to make it more specific, the user is usually requested to enter a user name. Now the server only has to compare the measured or imaged indicia against the stored indicia corresponding to the entered username. In some cases the user may be further asked to enter a password creating what is sometimes referred to as a two factor authentication system.

However, these systems can take a long time to determine if there is a match or not and none of them are perfect. Each tolerates a level of false positives in order to ensure the level of false negatives, which irritate the user by rejecting them, are kept to a minimum. Furthermore these systems can be confused by biometric indicia changes (laryngitis for voice imagers, finger cuts or trauma for fingerprint readers, or shaving facial hair for face detectors). In some environments it is not easy to measure the biometric indicia, for example fingerprints for workers wearing protective gloves (e.g. nurses, those exposed to environmental extremes) or facial features for workers wearing hats or masks (e.g. when the temperature is extremely cold).

In situations where computers users frequently use a computer for a period of time, leave it for a while, and then later user it or another again, biometric indicia measurements can be a substantial drain on the users' time. They spend more time being authenticated than using the computer.

Other technologies used include smart cards with or without proximity detectors and electronic token generators. A smart card can be inserted into a reader attached to a computer, which reads a special code (e.g. time varying codes) and sends that to the security server often with a user name and password, also creating a two factor user authentication. When the user is finished working at the computer they must be careful to remove the smart card otherwise anyone else can use the computer. When a smart card can be detected by wireless proximity means, the user gains access as mentioned but by leaving the computer they can be logged off the computer when the card can no longer be detected. This prevents anyone else form using the computer without authenticating himself. In some cases smart cards are used with biometric indicia to create a three factor user authentication. While smart cards can provide a higher level of security they are at least as time consuming as passwords for workers who use computers for short periods of time, frequently throughout the day.

Electronic token generators are typically calculators that compute time varying codes that are presented to a user via a LCD screen. The user who wants to access a computer uses a terminal to enter their user name, the current code, and sometimes a password as well. This is received by a security server, which compares the code with an algorithm that is unique for the specific user to determine if the user and the entered code match. Token generators are particularly disliked when the user must access computer terminals frequently throughout the day as they must examine the token and enter the long numeric value properly.

Another restricted access system involves the use of user-specific password-generating devices. Typically, a user seeking access to a secure system is presented a code or instruction on a system terminal screen. The user enters the code or the information demanded by the instruction, via manual entry or optical coupling, into his own password generating device. The password generating device then calculates a second code based upon the user's input and an encryption algorithm stored by the device, and displays this second code to the user for entry into the computer terminal or workstation. After the user enters the second code, the computer terminal or workstation then performs a verification check on it to confirm its creation by the password calculator of an authorized user of the computer terminal or workstation. If confirmed, the user is granted access in accordance with the user's system access privileges.

Yet another restricted access system requires a user to insert an authorization card, e.g. a PCMCIA card, into a computer card reader to authorize access and to authenticate information entered at the computer terminal with the users digital signature. One potential weakness of such a system is that a hidden program could present documents for signature without the proper control of the user. Another weakness with these implementations is the relatively high risk that an authorized user will forget to or fail to remove his card in the card reader before he leaves the terminal—a risk that is particularly acute for a nurse or doctor who may have to leave a terminal in emergency situations to attend to a patient's care. Also, the loss of the card will result in a significant inconvenience to the owner and the system administrator.

Lemelson, in U.S. Pat. Nos. 5,202,929 and 5,548,660, discloses an access control system utilizing detection devices such as speech recognition equipment and fingerprint scanners to analyze one or more physical characteristics of a person attempting access to a computer. The system also incorporates physical presence sensors such as motion detectors and limit switches embedded in seat cushions to track the presence of an authorized user so as to prevent continued access to the system when the authorized user leaves or is absent. This system is primarily directed to accessing desktop computer terminals on a sensitive computer network and is not easily adaptable, however, for restricting access to laptops, portable instruments, medical equipment such as respirators, or electronically-controlled medication dispensers. Moreover, the implementation of the Lemelson invention requires a significant amount of detection equipment and analysis software, which may not be adaptable to the cost, space, and portability requirements of many devices for which restricted access and auditing control is desired.

Users and system owners need improved user authentication systems that do not impede the workflow, yet maintain a higher level of security and to do not slow down security servers with constant reauthentications.

BRIEF SUMMARY OF THE INVENTION

The present invention relates to a limited access system for a computer network with a multitude of users. More particularly, the present invention relates to a limited access system providing automatic log-on and log-out for network users by means of coded communications between transceiver devices worn by network users and transceiver devices connected to computer terminals on the network. It also facilitates rapid secondary log on to a computer network by the user provided the secondary log on attempt is within a time range of an initial successful log on.

This invention uses an electronic device to assist computer systems authenticate users. The device may be a smart card with electrical contacts, a wireless proximity identification badge conveniently worn by a user, a PDA, cellular phone, or other acceptable forms. The device is used to assist with the authentication and reauthentication of users to computer systems. In some cases it is also used to authenticate users to computers, to automatically log users off computers upon their departure, and track which users are accessing each computer terminal in a network.

In an initial or basic version, the user has an electronic security device and authenticates himself according to the standard computer security protocol, e.g. a user name and password, biometric indicia, or by using codes in the electronic device itself. When the user has been granted access to the computer terminal a reauthentication code is transferred to the electronic device by a security server or by the local computer terminal. This code includes a time component and may also include a location component. The code is transferred by inserting the device into a reader/writer attached to the computer terminal or via a wireless link when the device is addressed using an identifier associated with the user and owner of the device. The user uses the computer as normal and logs off the computer when they leave.

It should also be noted that the electronic security device can be used to assist in logging the user off the terminal. When the electronic security device is a smart card the user may be logged off by removing it from the reader/writer. When the electronic security device has wireless communication that has a limited range (e.g. 3 m or less) it can be used to log the user off when he moves from the computer terminal beyond the limited range. To do this the computer terminal transmits signals addressed to the device on a periodic basis, which in turn transmits a response signal back to the computer terminal. When the user leaves the area near the computer workstation (e.g. within 3 m) the response signals are not longer received by the computer terminal, which then logs the user off (although a short period of absence may be accepted before the user is logged off). Alternately the security device may periodically or continuously transmit a signal identifying itself with a limited range. Once the user has logged onto the computer terminal the terminal receives signals from the device that it can correlate to the user. When the signals are no longer received for a period of time the computer terminal logs the user off.

When the user returns to any terminal they may insert their smart card into the reader/writer, which in turn reads the reauthentication code. The local terminal can examine the reauthentication code previously recorded in the smart card. The time component of the code is examined to see if the current time is within a time range defined by the time component. If it is the user is allowed to use the computer terminal without having to enter his password or provide a biometric indicia, if not the user must log into the computer system as mentioned before.

When the electronic device has wireless communication it can be used to log the user onto the computer system. This can be done by pressing an activation button on the device, which then transmits the reauthentication code and other user information as needed within a limited range. A nearby terminal with a wireless receiver will receive the code and again compare the time component to determine if the current time is within a range defined by the time component. Alternately the electronic device may continuously broadcast a user identifier and the code on a continuous basis to any terminal the user is near. Provided no one else is using the computer terminal, the user will be logged in if the time component is within the time range. A further alternate is for the user to press a key on the keyboard of the computer terminal, which in turn transmits a signal to the users electronic device requesting a user identifier be provided and the code. Again the time component of the code is compared to determine if it is within a time range. In an alternate configuration the computer terminal or computer network maintains the reauthentication code used to the period of time during which the user can be re-logged onto the terminal or computer system without being requested to reauthenticate himself.

In some cases the security device can use a timer to determine a time period in which it can be used to log a user onto a computer terminal by transmitting a log on code. In this case a reauthentication code is not needed. Once a user has been successfully logged onto a computer they can leave the terminal of computer system be logged off of at least have the computer be placed in a suspended state so that it is not readily accessible by others, and then when they return within the time period they can be logged on or given access to the computer without having to reauthenticate themselves to the computer manually. In this case the time period can be governed by the computer terminal.

There are other variations possible, but in each case the user is identified and a time component is provided that the computer terminal can recognize. The user is granted access to the computer terminal without having to enter additional information or request a reauthentication by the security server. It should be noted that there can be concern that the electronic device might be lost or stolen and then another person (an unauthorized one) will use the device to gain access to a computer terminal of the computer system. To prevent this the time range for automatically being re-logged in can be adjusted from a few minutes to perhaps several hours based on the goals of the computer security planners. A smart card or a PDA is easily left behind without notice and therefore they may have a shorter time range defined, while an electronic identification badge is typically worn all day without removal and therefore is less likely to be lost and may be granted a longer time range.

When the reauthentication code includes a location component it can be used to define a portion of the entire computer system that the user previously logged onto. If the code received, read, or obtained from a computer network by a computer terminal for a specific security device doesn't include a location component that is the same as the computer terminal, the code will be ignored and the user if they want to use the computer system will have to log in to the system using the standard log process (e.g. user name and password). In other cases the location component is used to define neighborhoods of terminals within a computer system. These terminals are usually within a common physical area or department. The computer terminal after receiving the location component may further compare it to determine if it specifies the same neighborhood as the current terminal. If so the user is logged on to the computer system, if not the user must log on as usual. When the user attempts to use a computer terminal that is not in the same neighborhood as indicated by the location component, the reauthentication code in the electronic device or in a computer network (e.g. a security server) can be erased. This will force the user to log in, even if he returns to a terminal in the previous neighborhood.

Using the methods defined above, a user who is authenticated (by logging on normally) can use any terminal within a neighborhood for a period of time without having to be reauthenticated. Yet if the time period is exceeded or if the user attempts to use the terminal in a different neighborhood, they will be required to authenticate themselves again. This provides an increased ease in user access to computer terminals while still providing each terminal a level of security that can be tuned by the computer security planners and is referred to as the neighborhood roam feature.

In some situations it will be desirable for part of the reauthentication code (e.g. a user identifier) received by the computer terminal to be transferred to the security system along with a terminal identifier (e.g. Ethernet address). The security system can maintain a list of users who are currently using terminals. When a user leaves a terminal and is automatically logged off, as described above, a message is sent to the security server that the user is no longer using the terminal. In this manner the security server maintains a list of which user is using each terminal.

When the electronic security device is used to provide automated log on to terminals via the transmitted reauthentication code there is a concern that someone can misplace the device and an unauthorized person would try to use a terminal using the reauthentication code. Once missing the user who is associated with the electronic security device may be unaware they no longer have it. This allows another person to use it as long as the time component is within a defined time range and the neighborhood component matches that of a computer terminal.

However, once the user notices that they cannot locate the electronic security device; he places a call to the computer security staff telling them that his device (e.g. an identity or other badge) is missing. The staff can then make an entry in the security system that if the user's device is attempted to be used to gain access to the computer system that it should be denied and that other nearby staff should be notified (e.g. by e-mail, pager, or phone) to question the individual attempting to use it.

However the person who has the device may already been used it to be logged on to a terminal by the reauthentication code (assuming the user has not yet noticed the device is missing). In this case once the user identifies the missing device to the computer staff, whom will enter information about the device into security system. The system will determine that the electronic security device is already being used by someone to access computer resources. The security system will send a message to the computer terminal indicating that the terminal is to immediately log the person off the terminal and erase any information on its display. Again a message can be sent to nearby staff that the person at that terminal should be questioned. In some cases the computer terminal will activate an alarm to draw attention to the unauthorized use of the terminal and erase the reauthentication code.

A further benefit to the use of an electronic security device is that it can be used to detect trusted computer systems. Before a user attempts to log onto a computer system, the security device in the form of a smart card is inserted in to a reader/writer or as a wireless device is brought within the vicinity of a computer terminal. The computer terminal is queried for or automatically provides information identifying the computer system and/or the terminal. The security device will have been preprogrammed with a list of trusted computer system identifiers. The received computer system identifier is compared to the list of trusted site identifiers, if there is a match the user is allowed to log onto the computer system as usual, if not they are denied access and the electronic security device may provide an alert as a message displayed o the computer terminal screen or by activating an audio or visual indicator that is part of the security device. In this manner the user is prevented from attempting to provide their user name, password, or biometric indicia to systems that are not registered with the badge, systems that might have been under the control of hackers who may attempt to gains knowledge of the user's log on identification or measured biometric indicia.

In some cases the electronic security device can include an address of one or more trusted computer systems or servers. The user can be provided a list of these systems when using a terminal that may not otherwise be part of a trusted network (e.g. a public terminal). The user by selecting a system, can then be directed to via the Internet or other communication channel to the selected system. To enhance security critical portions of or all communication with the system is encrypted by the electronic security device; creating a personal "tunnel" or virtual private network. The computer system may be required to provide identity information to the electronic security device, allowing the security device, as above, to determine if it is communicating with a trusted system in the trusted system identifiers list.

As discussed above another benefit to the use of an electronic security device is that it can be used to help provide a user's user name and password (a password that may be too long and complicated for anyone to remember, e.g. "ai8&weMd2F3!mH,kqw7<whz%F9") to a security system. This can be done by using the security device as inserting a smart card in a reader/writer or bringing a wireless device within range of a computer terminal. The electronic security device can send a message to the computer terminal that is presented on the screen of the terminal asking the user to provide the answer to a challenge question. The user enters the answer, which is verified by either the computer terminal or by the electronic security device against a user defined answer stored in the device. If there is a match the user's user name and password are sent by the security device to the security system for authentication.

The challenge question may simply request the user enter a password as a response, or the challenge question may refer to a fact that only the user is likely to know. An example is "What is the name of your favorite TWWOO character?" where the user knows that TWWOO refers to the book the "The Wonderful Wizard of OZ" and the character's name is "Glinda". To further increase security, the user can define several challenge questions and answers that are randomly presented when the user attempts to us the electronic device to assist the user log onto a computer system.

However, an unauthorized person may find a misplaced security device and attempt to use it to access a computer system. Assuming the real user has defined challenge questions and answers that are not obvious the person will have to guess several times to enter a correct answer. To prevent this type of brute force cracking, the electronic security device can be programmed to accept only a limited number (e.g. 4) of incorrect answers or failures to enter an answer at all after being requested. After the limit has been exceeded the device performs a security function. The first time this occurs (which may be within multiple repeated entries or accumulated over an hour) the function can be to deactivate the device for 5 minutes and present an error message on the screen Should the user continue to enter incorrect answers the function may be to erase portions of the security device's memory, e.g. the challenge questions and answers or definitions that are related to the computer system identified by the computer terminal so that the security device will no longer interact with the terminal.

In some cases the terminal will send a message identifying the electronic security device (e.g. by generic serial number or the user's real name), as well as the identity of the terminal, to the security system. The system can mark the identified electronic security device as questionable and before the security device is used to assist the user log on again, it may require the person using it to present themselves to trusted staff to determine that the errors in entering correct answers were mistakes as opposed to hacking attempts.

A similar process can be used when the electronic security device is able to measure and compare a biometric indicia prior to assisting a user log onto to a computer system. For example when the security device is able to read the fingerprint of the user and an incorrect fingerprint is presented multiple times, the electronic security device may perform a security function.

The inventive identifier has several advantages over prior art indicia identification systems. First, because the inventive identifier is personal to a single user, the identifier's memory need only store finger print characteristics for a single user. For this reason minimal memory is required. In addition because only one print has to be interrogated, a relatively simple processor can be used to interrogate a finger print and identify a user.

Second, the inventive identifier or security device keeps personal information secret while still facilitating user identification. In many conventional person interrogating systems which identify body indicia, a person's body indicia has to be "given up" to an interrogation system which is not controlled by the person. For example, to enter a building, an interrogation system may require a person to place her thumb on a finger print reader which identifies her print characteristic and then compares her characteristic to characteristics of prints associated with all people who are authorized to enter the facility. In this case the person's print would have previously had to have been provided to the system so that a comparison could be made. Providing personal indicia is viewed as intrusive by many persons and therefore is objectionable.

With one embodiment of the inventive indicia identifier, all indicia identification occurs on a security device (e.g. a badge, credit card, cell phone, or PDA) which is controlled by the device owner at all times and therefore control of personal indicia is never forfeited. With another embodiment of the invention a user's indicia is provided to an external interrogation system only for interrogation purposes and is thereafter erased from the systems memory. According to this embodiment, for example, a user's fingerprint characteristics may be stored in an electronic security device memory, e.g. a smart card or the like. To gain access to a computer network via terminal an interrogation must occur. To this end, an interrogation system includes a processor which can receive information from the electronic security device and which is linked to a print reader. During an interrogating process the person first enables print characteristic transfer from the electronic security device to the processor. Next the user places her thumb on the print reader which provides print characteristics to the processor. Thereafter the processor compares the prints (i.e. from the reader and the electronic security device) and allows access where the prints are identical but blocks access where the prints are different. Then the processor erases the prints from memory and may indicate so for the user's peace of mind.

The invention also includes a method and apparatus for checking authenticity of a digital or hardcopy document using only content provided on the document. To this end, assuming a document exists in a computer memory and can be displayed for approval on a computer display. A user may examine the document and, if the user approves the document, the user may indicate approval (e.g. via a key or icon selection). When approval is given, the computer performs two tasks. First, the computer provides some form of user or personal identifier to the document in a designated approval field or space. The identifier may take any of several different forms and may include a signature picture of the person who approved the document or a personal watermark. This first task results in a "signed" document. Second, the computer uses document content and uses a personal key which belongs to the approver to compute encryption codes, hash code, etc. The encryption code is then used to modify the identifier which is indicative of signed document content. The modified identifier is appended to the document, making it a signed document. When the document is stored modifier identifier is included therewith and may be displayed when printed when it is in the form of a signature picture. In some cases the identifier provided is the encryption code calculated in part by the document content and a private key provided by the security device.

Subsequently, the content of a signed document can be authenticated as having been singed by a specific security device. When a signature picture is used that is modified in part by the original content the document, the signature picture or watermark can be read from the document and decrypted using a public key which belongs to the person whose signature appears on the document (supposedly the original approver). At the end of the decryption process, the resulting document should match the original document content and can be compared either visually or automatically to authenticate the signature and the document content. When encryption codes are stored with the document instead of a modified signature picture, the encryption coding process can be reversed using a public key corresponding to the private key of a specific security device to determine that the document was signed by the person associated with the specific security device.

These and other objects, advantages and aspects of the invention will become apparent from the following description. In the description, reference is made to the accompanying drawings which form a part hereof, and in which there is shown a preferred embodiment of the invention. Such embodiment does not necessarily represent the full scope of the invention and reference is made therefore, to the claims herein for interpreting the scope of the invention.

BRIEF DESCRIPTION OF THE SEVERAL VIEWS OF THE DRAWINGS

FIG. 8 presents the base memory contents of a security badge;

FIG. 9 presents the contents of the information transferred from a wrist bracelet according to the present invention to a security badge;

FIG. 10 presents the contents of the information transferred from a medical container according to the present invention to a security badge;

FIG. 11 presents the contents of a digital message record incorporating a dictated message and other information corresponding to the dictated message;

FIG. 14A is a graphical representation of a medical administration record with HTML codes for displaying the information in a network browser;

FIG. 14B is a continuation of the graphical representation of a medical administration record of FIG. 14A;

DETAILED DESCRIPTION OF THE INVENTION

The present invention may be adapted for use in a wide variety of applications and is suitable for any environment in which numerous data records having one or multiple forms and/or formats are to be collected, stored, archived, retrieved, or translated. By way of illustration and not by way of limitation, unless indicated otherwise, the preferred embodiment is presented in the context of a medical facility environment in which typically there are numerous computer systems in use by various physicians (e.g. doctors, nurses, administrators, etc.) in several related hospitals, and each physician often desires to have access to patient records created by that physician or by other physicians who practice at one of the related hospitals. Throughout this specification, identical numbers represent similar components and symbols.

I. Hardware

Figure 7:
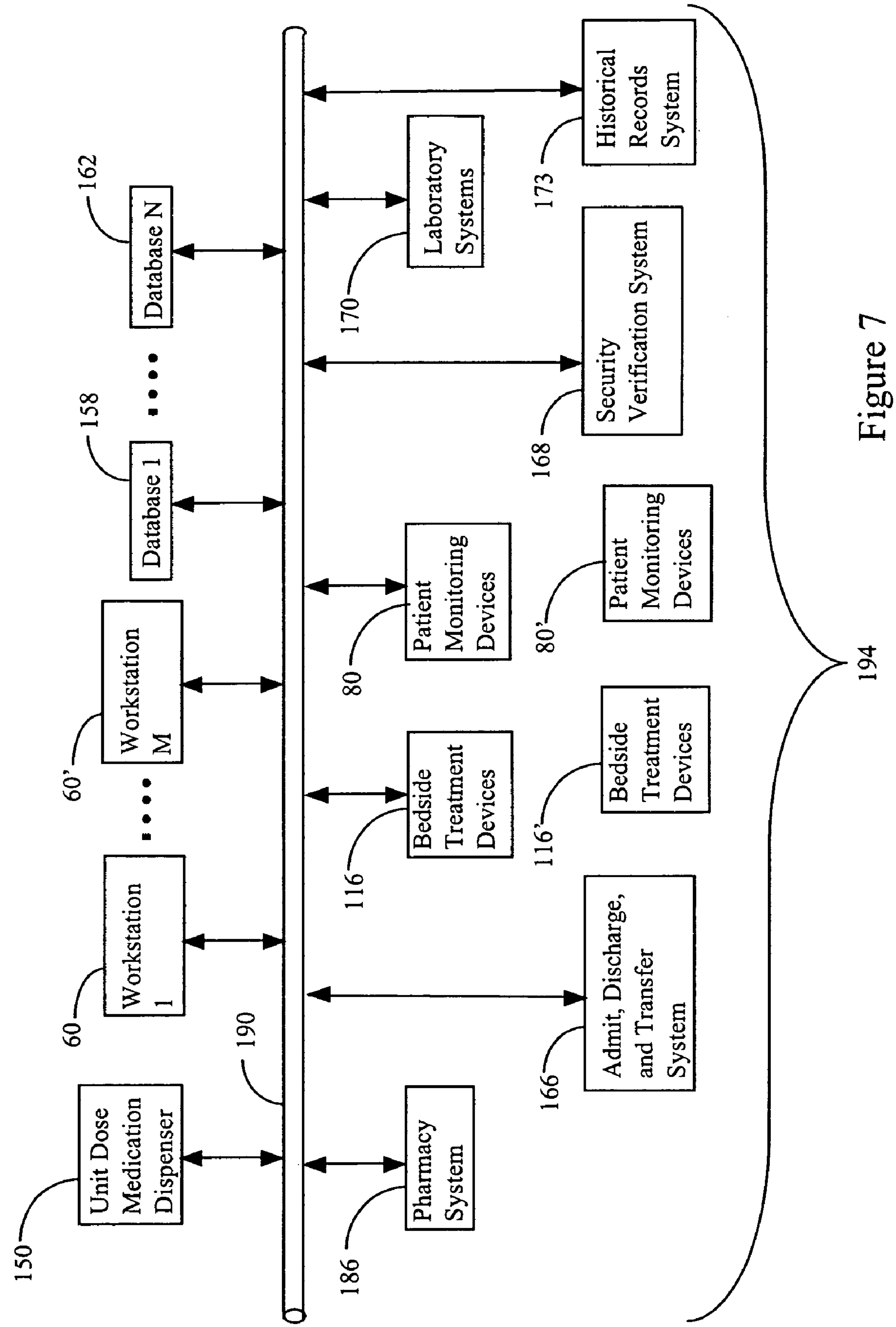
FIG. 7 is a block diagram of a computer network according to the present invention, including a plurality of workstations and databases for data record retrieval and storage and a security verification system.

Referring to FIG. 7, a simplified and exemplary embodiment of a system used with the present invention is illustrated as an electronic system referred to as computer network system 194. System 194 includes a plurality of personal computers or computer terminals comprising workstations 60 and 60' (designated "Workstation 1" and "Workstation M"), which may be located in patient rooms, at nurse stations, in doctor offices and administrative offices, a plurality of network devices including databases 158 and 162 (designated "Database 1" and "Database N") and servers including an Admit, Discharge, and Transfer (ADT) system or server 166, at least one laboratory system or server 170, various bedside treatment devices 116 and 116' such as ventilators and IV infusion pumps, patient monitoring devices 80 and 80', a pharmacy system or server 186, a security verification system or server 168, a billing system or server 171, a patient historical records system or server 173 and a unit dose medication dispenser 150.

For the most part, system 194 components communicate with each other via a communication network 190 which may comprise a combination of local and wide area networks, using ethernet, serial line, token ring, wireless, or other communication standards. Communication network 190 may also be arranged so as to be part of the Internet or as an individual Intranet. The functions performed by the various components of the preferred embodiment of system 194 may be divided among multiple computer systems or consolidated into fewer components.

Each of system servers 186, 166, 173, 168 and 170 has access to one or more databases 158, 162 for storing information including text and/or audio and visual data. As illustrated, some patient monitoring devices (i.e. 80) and treatment devices (i.e. 116) are hardwire linked to network 190 so that data from devices 116 and 80 can be provided directly to network 190. However, there are other monitoring devices 80' and treatment devices 116' which stand alone and apart from network 190 which, although capable of generating data, are not hardwired to network 190 to facilitate information interchange.

Figure 3:
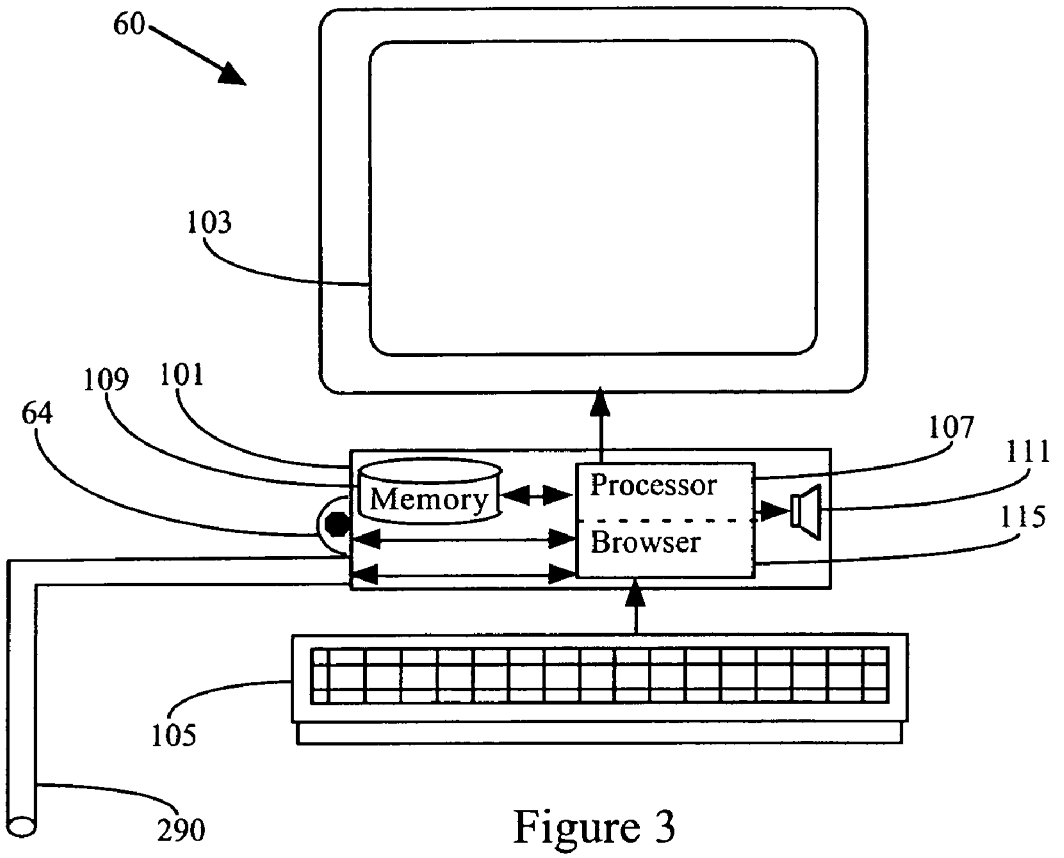
FIG. 3 is a plan view of a computer terminal or workstation being operated by a system user where access is conditioned upon communications between the security badge and the computer terminal.

Referring to FIG. 3, an exemplary terminal 60 includes a computer 101, a display 103, an interactive device 105 and an input device 64. Computer 101 includes a processor 107, a random access memory 109 and an audible alarm 111. Processor 107 is linked to memory 109, alarm 111, input device 64, display 103, and device 105. In addition, processor 107 is linked to network 190 for two-way communication with other components of system 194 (see FIG. 7). Device 105 is illustrated as a keyboard but could be any of several different devices including a mouse or other similar pointing device.

A commercially available Internet browser 115 or similar display, entry and retrieval program using standardized formatting instructions is loaded onto processor 107. For the purpose of simplifying this explanation, while any type of entry, retrieval and display software may be used to implement the present invention, it will be assumed that browser 115 is a standard Internet browser. Generally, browser 115 operates as an interface mechanism between a physician and the servers (e.g. 186, 173 . . . ) of system 194. To this end, browser 115 configures various screens on display 103 providing information such as instructions, hyperlinks and blanks which facilitate interaction between a physician and the servers. Typically, where information is to be provided by a physician (e.g., through selection of a hyperlink or entry via device 105), a target server address for reception of the information is provided.

The target server address will typically take one of two basic forms. First, the target address may simply indicate a data base address on one of data bases 158-162 for storing received information. Second, the target address may specify a specific system 194 server and, when a server receives information, the server may determine how to proceed (i.e. process or store the received information).

Input device 64 is a transceiver which is capable of two-way communication with other devices described hereinafter. While device 64 may be equipped for wired communication, preferably, device 64 is capable of any of several different types of wireless communication. Because of its low cost, energy efficiency, minimally regulated status, and standardization by the Infrared Data Association (IrDA), infrared transmitter and receiver components supporting serial infrared communications links comprise the preferred transceiver 64. A variety of infrared communications devices, such as Hewlett Packard's HSDL-1001 transceiver components, may be used to implement the preferred communication means. Alternatively, other communication means (e.g. acoustic, radio frequency, or electromagnetic coupling) may be supported.

Referring to FIGS. 3 and 7, dispenser 150 may take any of several different forms but preferably is a terminal like terminal 60 including a processor 107, a browser 115, a memory 101, a specifier transmitter or output device 64, and an indicator 111. In addition, other useful functionality is provided by processor 107, for example, timing, counting, indicator and display control and so on. Dispenser 150 is in communication with pharmacy server 186. Thus, server 186 provides screen configuration information as well as server target addresses to dispenser 150 for interaction with a pharmacist who is responsible for dispensing drugs. In addition to dispensing drugs, dispenser 150 may also dispense target address information and browser configuration information to other system devices used for remote information collection and may perform some information tracking tasks described in more detail below.

In addition to the devices, systems, and servers identified above, the inventive system includes a series of other electronic devices which cooperate to remotely gather information within a medical facility and provide information to system 194 for storage and manipulation.

Figure 1:
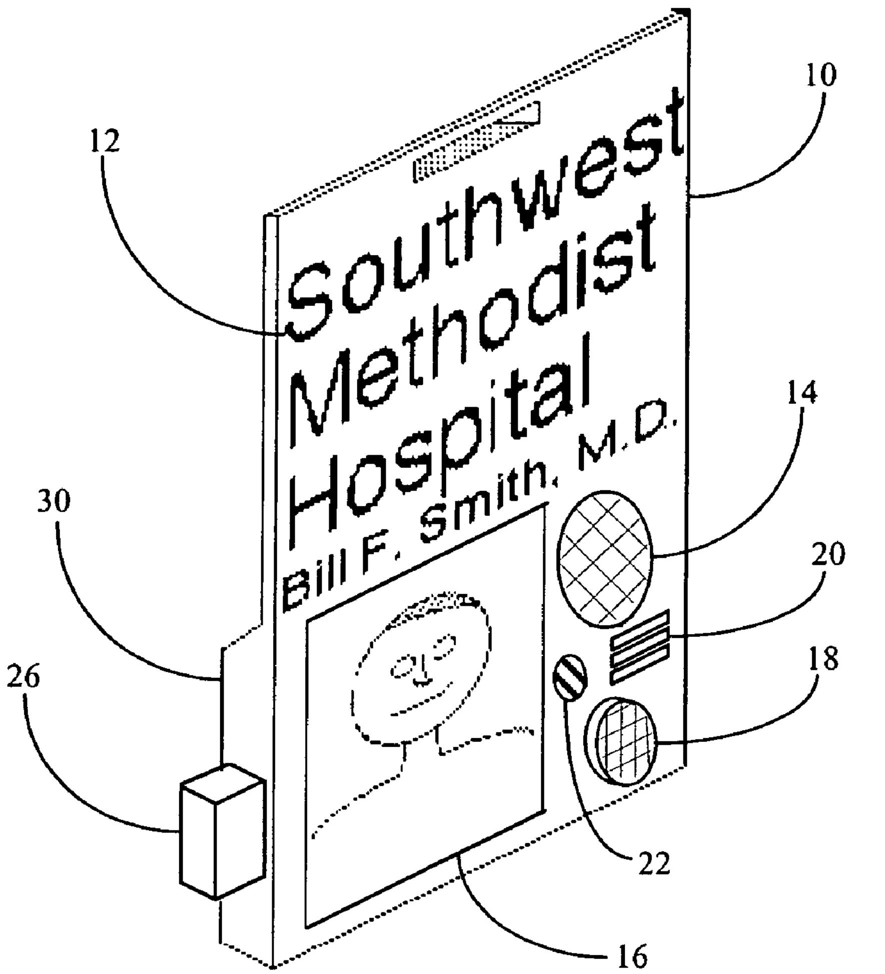
FIG. 1 is a perspective view of a security badge capable of communicating with computer terminals and a plurality of smart devices.

Referring to FIG. 1, a mobile information collecting device (ICD) is illustrated in one embodiment as a security badge 10 which may be clipped to a physician's clothing or worn by chain around a physician's neck. While this embodiment implements the invention in the context of an identification badge, the invention could be instantiated in other shapes, such as a ring, a personalized pointing device or a small hand held computer. In keeping with its preferred resemblance to a typical identification badge, ICD 10 is affixed with identification text 12 and graphic display 16. ICD 10 incorporates a wireless communication means or transceiver 14 (i.e., a receiver/transmitter) which operates as both a data collector and an output device, an audible alerting device 20, an activation button 18, a microphone and audio digitizer 22, and a dictation button 26. ICD 10 may also incorporate additional electronic identification means such as a magnetic strip (the general location illustrated at 30) and may also incorporate a small key pad (not illustrated) for entering additional information.

Figure 6:
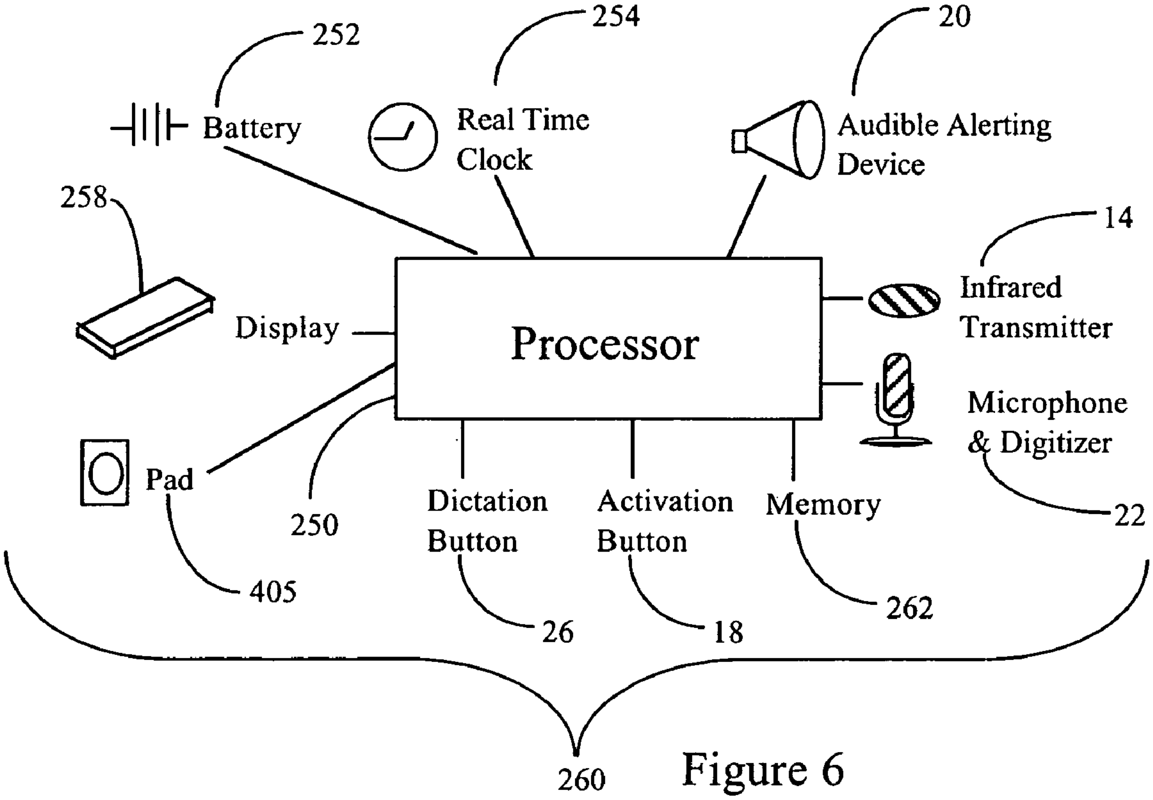
FIG. 6 is a block diagram of various electrical components which are incorporated within an exemplary ICD.

Referring also to FIG. 6, ICD 10 comprises a processor 250 which is linked to each of a battery 252, a real-time clock 254, a memory element 262, audible alerting device 20, transceiver 14, activation button 18, microphone 22 and dictation button 26. Display 16 of ICD 10 may be any of a variety of forms, including but not limited to a photograph, a light emitting diode array, a liquid crystal panel, and an active-matrix display. In addition, ICD 10 may include a display 258 such as a light emitting diode array, an LCD screen, or a passive or active matrix screen, which is linked to processor 250.

Referring to FIG. 8, exemplary information 300 which may be stored in memory element 262 is illustrated. Information 300 includes both "base contents" and "optional information". The base contents comprises the minimum information which should be stored in a personalized ICD such as identification ICD 10 and includes a physician's password or private/public digital security key information which can be used to log onto a computer terminal to provide information to, or review information thereon. The optional information includes other information which is descriptive of a badge owner including a user identifier such as a name, identification number, occupation, privileges and so on.

While personalized ICDs are preferred, the invention also contemplates other types of ICDs which are not personalized and can therefore be used by any facility personnel to collect information for entry into a facility computer system. In this case, however, prior to entering information into the system, it is contemplated that a physician would log on to a computer terminal in a more conventional manner via system 168 which would identify the physician for security purposes. For example, the physician might manually enter a personal identification number to gain access to the computer terminal for information entry and retrieval.

ICD 10 is to be used with a plurality of different "smart devices" for remotely collecting information. In addition to remotely collecting information, inventive ICD 10 is equipped to provide information packets to terminal input devices 64 which are formatted and addressed according to uniform standards in order to minimize the need for human intervention in categorizing and archiving patient records. Information packets are formatted and addressed according to conventions, such as Java or a markup language supporting interactive display by browser 115. While any standard format (e.g. HTML, Java . . . ) may be supported and it is contemplated that the present invention may be used with any computer language format, hereinafter, in the interest of simplifying this explanation, the invention will be described with reference to the HTML format only.

By formatting information packets in HTML format a receiving computer terminal 60 does not need additional programming or input to display or manipulate information in an information packet. In a preferred embodiment, formatting and addressing of information packets is done partially or entirely by ICD 10 itself, using time stamps, patient identification information, and the information or contents 300 (FIG. 8) incorporated in memory element 262 (FIG. 6) of ICD 10. In this manner all the information required to display information packet information and to send the information to an appropriate database or server is included in the information packet transferred from ICD 10. An exemplary information packet is described in more detail below.

Figure 19:
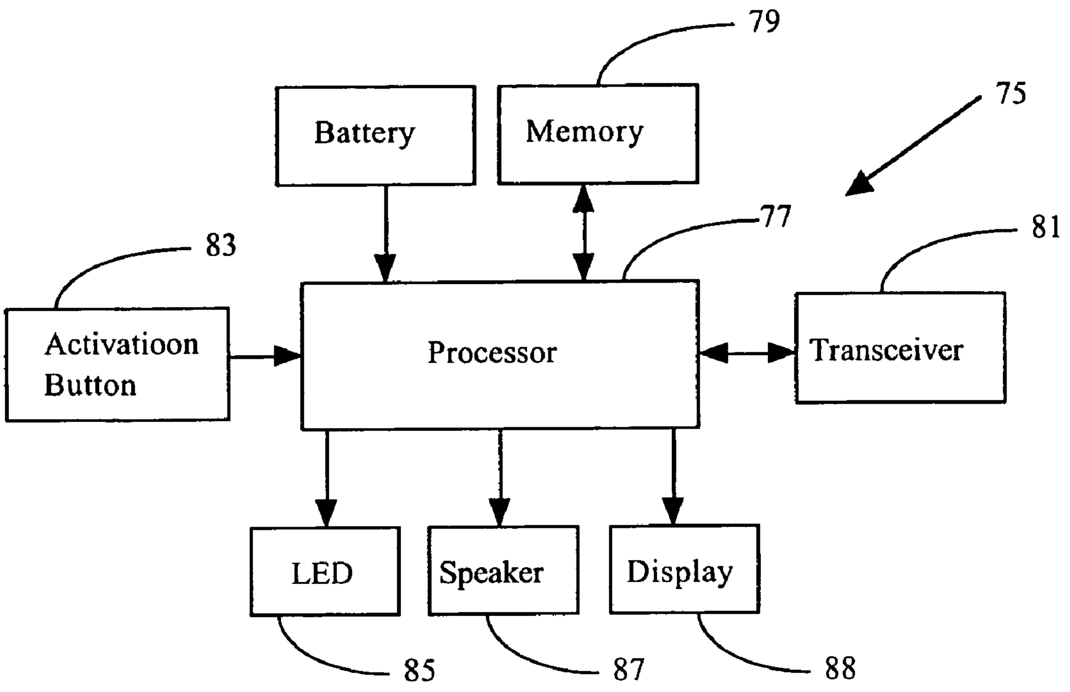
FIG. 19 is a block diagram illustrating the general components of a smart device according to the present invention.

Referring to FIG. 19, an exemplary smart device 75 generally includes a processor 77, a memory 79 linked to processor 77 and either a transmitter or a transceiver 81 (i.e. a receiver/transmitter). In addition, each smart device 75 may also include one or more activation buttons 83, some type of indicator (e.g. a light 85 or audible alarm in the form of a speaker 87) and a display 88. Smart devices like device 75 collect, generate, and/or are provided information which is assembled into information segments to be transmitted to ICD 10 for collection. Many smart devices 75 are contemplated by the present invention, however, in the interest of simplifying this explanation, only a small number of smart devices are described. Hereinafter when specific smart device components are referenced, the specific components will be referenced by the same numbers used in FIG. 19 followed by one or more "'" indicating components associated with specific devices as described hereinafter.

Figure 2:
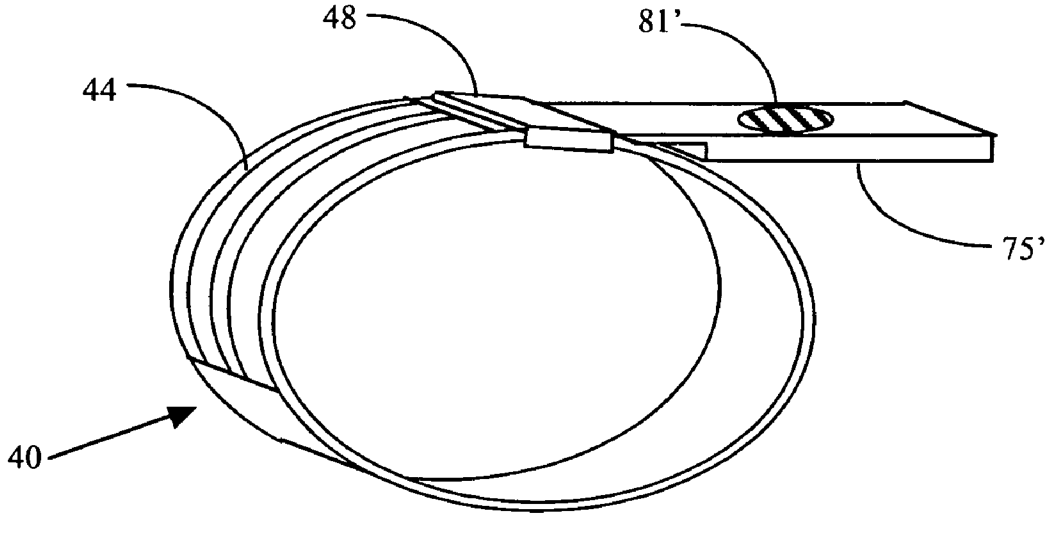
FIG. 2 is a perspective view of a wrist bracelet to be worn by patients or other persons to provide identification through wireless communication with security badges or other smart devices.

Referring now to FIG. 2, one smart device is a patient identification bracelet 40. An exemplary bracelet 40 is described in U.S. patent application Ser. No. 09/007,290, which is entitled "Identification Bracelet With Electronic Information", which was filed by the present inventor and is incorporated herein by reference. Bracelet 40 includes a flexible and extendible band 44, a securing clasp 48, a processing device 75' and a wireless communication means in the form of transceiver 81'. Bracelet 40 is similar to existing bracelets used to identify patients in hospitals, with the exception of the processing device 75' which includes transceiver 81'. Textual information (not illustrated) is typically affixed to band 44. Transceiver 81' is preferably similar to transceiver 14 of ICD 10 so that transceivers 81' and 14 can communicate back and forth. Like general device 75 (see FIG. 19), device 75' includes a processor and a memory element linked to the processor (not illustrated).

Referring also to FIG. 9, exemplary patient identification information 320 to be stored in the memory of device 75' is illustrated and includes, at a minimum, a patient identification number identifying the patient who wears bracelet 40. In addition, the identification information 320 may also include other descriptive information as indicated.

Figure 5:
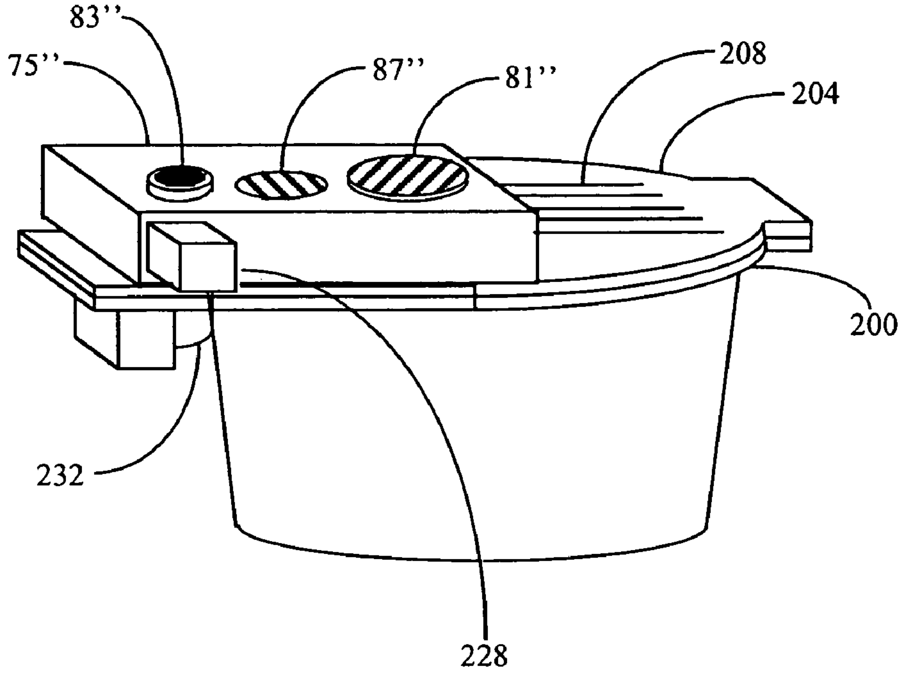
FIG. 5 is a perspective view of a medical container equipped with an electromechanical locking device controlled by communications through transceiver components.

Referring to FIG. 5, another smart device is a medical container 200. U.S. patent application Ser. No. 08/955,475, entitled "System And Apparatus For Administering Prescribed Medication To A Patient", which was filed by the present inventor and is incorporated herein by reference, describes an exemplary medical container. Exemplary container 200, which may be used to transport and provide auditing and limited access for medications, blood or tissue samples, or other inventory, includes a lid 204, a securing latch 232, a latch release button 228, and an electronic identification or processing device 75". Textual identification 208 may be attached to lid 204. Processing device 75", like general smart device 75 (see FIG. 19) includes a processor which is linked to a memory, a battery, a transceiver 81", an activation button 83" and an audible alerting device 87".

Referring also to FIG. 10, exemplary information 340 which might be stored in the memory associated with processing device 75" is illustrated. Once again the information is divided into a minimum amount of information which should be stored and optional information. In the case of a drug to be administered, the minimum information includes medication name and medication quantity. Optional information may include, among other things, the name of a patient for whom the drug is dispensed, the date and time at which the drug should be administered and the names of physicians authorized to administer the drug. Other information would be provided in the case of a tissue sample, a blood sample, etc.

Referring again to FIG. 5, it is contemplated that latch 232 release may be conditioned on any of a number of different precise sequences of events. The events may include release within a time-window for treatment, the successful exchange of identification information between a physician's ICD and processing device 75", the successful exchange of identification information between a patient's identification bracelet processing device 75' (see FIG. 2) and processing device 75" and the manual depression of the latch release button 228. An example of a lid unlocking sequence is described in more detail below.

Figure 4:
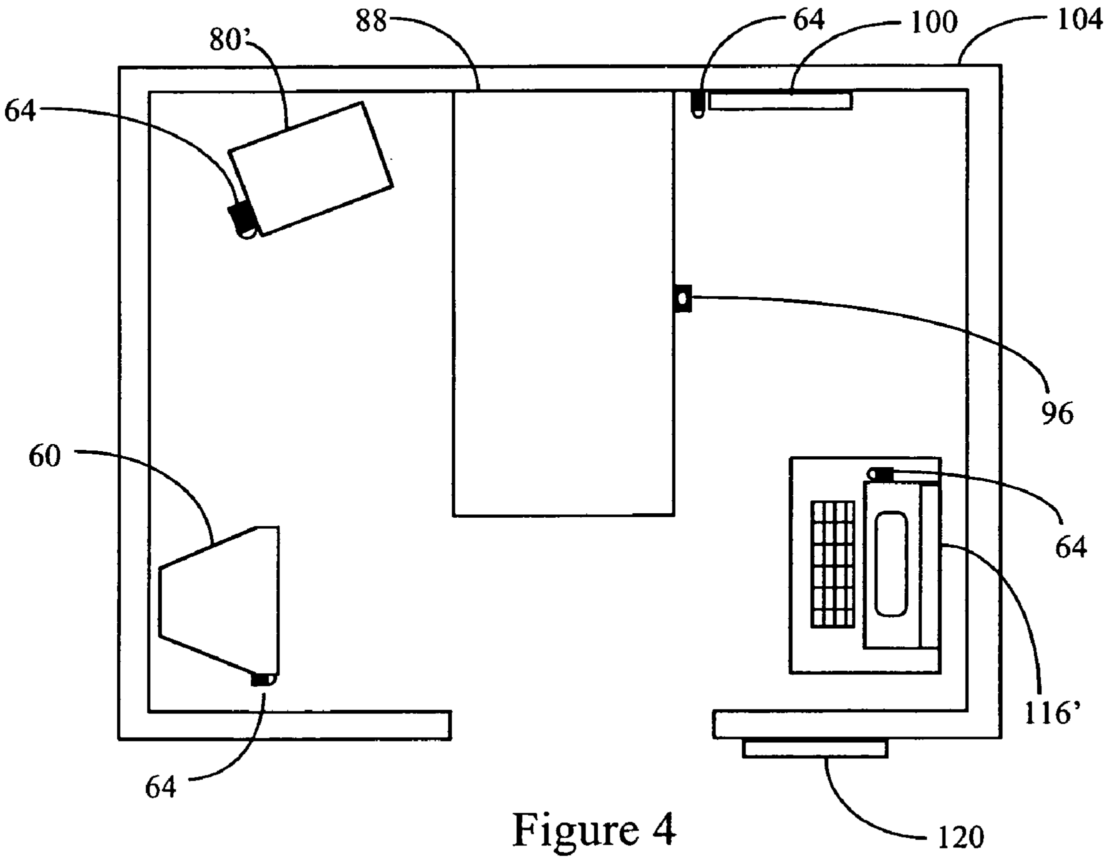
FIG. 4 is a plan view of a hospital patient room equipped with a variety of computerized monitoring, treatment, and information devices.

Referring to FIG. 4, an exemplary patient room 104 includes a computer terminal 60, a patient bed 88 and various other devices. The other devices include two smart devices including a patient monitor 80' and a patient treatment device 116', each equipped with a wireless transceiver input device 64 which is similar to transceiver 81' on band 40 (see FIG. 2) and transceiver 81" on container 200 (see FIG. 5). Monitor 80 and device 116 are smart devices meaning that each of those devices typically include the components illustrated in FIG. 19 (i.e. in addition to a transceiver, each device includes a processor, a memory, at least one activation button and some type of output device such as an LED or computer screen for visual indication or a speaker for audio indication). In this example, it will be assumed that each of devices 80' and 116' are not hardwired to network 194.

Also shown in FIG. 4 is an optional bedside communication device 96 which is equipped to communicate with wireless transceiver devices 64. Communication device 96 may be connected to an optional patient identification display 100 equipped with wireless transceiver device 64 or to a patient identification display 120 outside of room 104.

II. Operation of a Computer Terminal in Access Control

Generally, it is contemplated that a terminal used with an ICD 10 will be capable of, in addition to facilitating transfer of information packets from the ICD 10 to the terminal, facilitating use of other conventional computing programs (e.g. a word processor, a spread sheet, Internet access, . . . ). In enabling access to any facility application, security is extremely important.

In the preferred embodiment, authentication, interrogation and data security will be illustrated through the use of conventional "public key" cryptography, such as that implemented in RSA, though other well-known techniques for authenticating a user and securing transmitted data may be employed. In implementing public key cryptography, the security badges and computer terminals are equipped with "private key rings" of one or more private keys and a "public key ring" of one or more public keys. Depending upon their sophistication and the sensitivity of the information they contain, other smart devices in a medical facility, such as monitoring devices or medical instruments, may also be equipped with cryptographic means. The private keys of each ICD 10 are never transmitted or otherwise made accessible outside the ICD 10. For strong compression, each public and private key would typically be at least 128 bytes long. Today, the preferred implementation for smart card encryption capabilities utilizes the Advanced RISC Microprocessor (ARM), such as the ARM 6, the ARM 710, or a variety of customized chips integrating the ARM technology, such as the Mykronics Capstone or VLSI's VMS 210. A variety of other processors, including the Intel x86 processor, would also be suitable.

FIGS. 15A-15F describe the operation of a computer terminal 60 (FIG. 3) in interrogating, establishing and monitoring access by a physician wearing an ICD 10 (FIG. 1). Access is established by providing a substantially unobstructed signal path between the physical wireless communication means 14 (preferably comprising infrared transmitter and receiver components (see FIG. 1)) of the ICD 10 and the wireless transceiver device 64 of the computer terminal 60. The establishment of an unobstructed signal path is facilitated by having the ICD 10 worn on, or attached to, the front of the physician attempting to log on the computer terminal 60. While it is not necessary that the ICD 10 be worn by or attached to the clothing of the physician, securing the ICD 10 to the physician minimizes the probability that it will be lost by the physician.

Figure 15A:
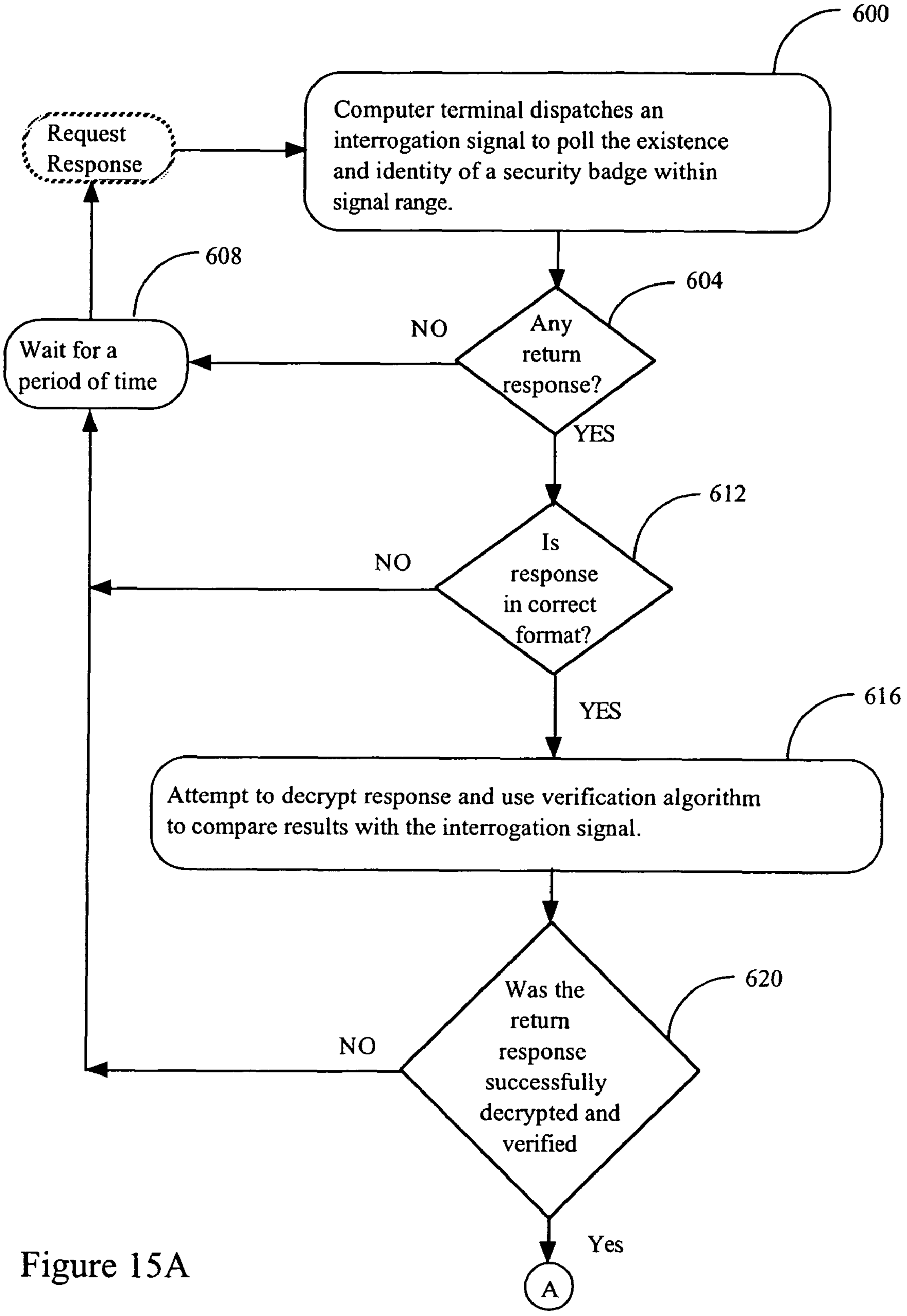
FIGS. 15A-15F are a functional flow chart showing the steps a computer terminal executes in logging on a system user using a security badge for identification.
Figure 15B:
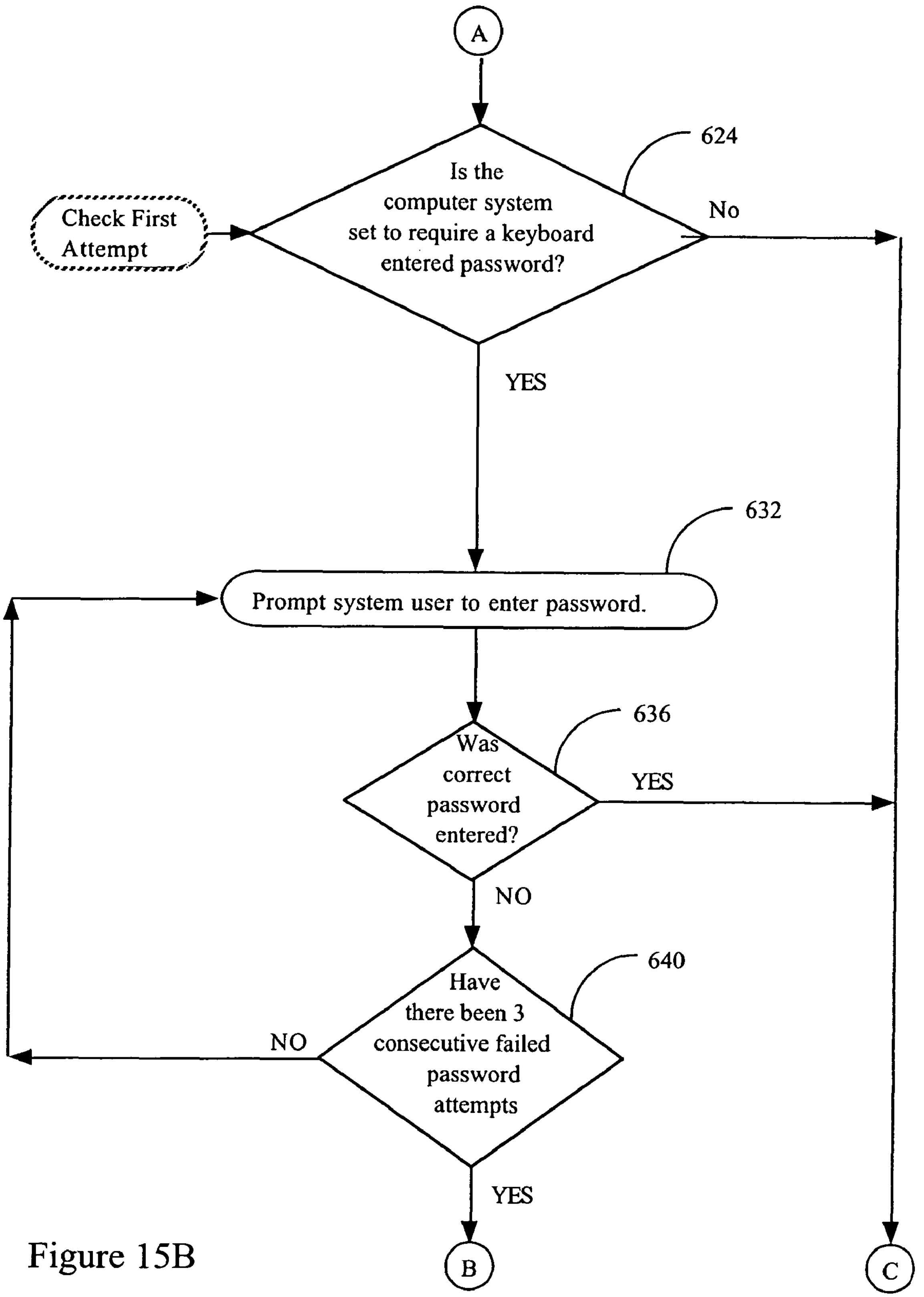

Commencing with FIG. 15A, in step 600 the computer terminal 60 transmits an interrogation signal, which is fashioned from a private key of the security verification system 168 (FIG. 7) of the computer network 194, a large random number, and other identification information unique to the security verification system 168. Provided a substantially unobstructed signal path exists between the wireless transceiver device 64 (FIG. 3) of the computer terminal 60 and the wireless communication means 14 (FIG. 1) of an ICD 10, the ICD 10 will intercept, process, and be operable to return a part of the interrogation signal in a re-encrypted form (according to the operation of the ICD 10 set forth in FIGS. 16A-16F, infra).

In step 604, the computer terminal 60 waits for a period sufficient to allow an ICD 10 to receive, process, re-encrypt, and re-transmit the interrogation signal. If no return response is received, in step 608 the computer terminal 60 waits for a predetermined period of time and, returning to step 600, transmits another interrogation signal. If a return response is received, in step 612 the format of the return response is evaluated. If the format is unrecognized, in step 608 the computer terminal 60 waits for a predetermined period of time and, returning to step 600, transmits another interrogation signal.

If a return response of a recognized format is received by the computer terminal 60, in step 616 it is decrypted or authenticated using the public key of the ICD 10 which returned the response. In a public key cryptographic system, encryption with a private key uniquely identifies the physician possessing that key (assuming the private key has not been stolen) because an encrypted message can only be decoded using the public key matching the physician's private key. Accordingly, the security verification system 168, which stores the public keys of each ICD 10 given access privileges to the computer network, attempts to decrypt the re-encrypted interrogation signal using the public keys it retains.

There are at least two ways in which the decryption procedure may be carried out. In one procedure, the security verification system 168 attempts to decrypt the response signal, one public key at a time, until either a successful decryption is achieved or all the public keys stored by the security verification system 168 fail. Preferably, however, the identification information will have been appended to the encrypted portion of the return response purporting to identify the ICD 10. The security verification system 168 then attempts to decrypt the return response using the public key corresponding to the appended identification information. A successful decryption identifies the ICD 10 that originated the return response. If the decryption is successful, a verification algorithm is used to compare the decrypted return response to the original, pre-encrypted interrogation signal.

It would, of course, be possible to program the computer terminal 60 itself to perform some or all the functions of the security verification system 168. A physically separate security verification system 168, however, will safeguard the computer network 194's private keys and the list of public keys of valid system users, preventing appropriation of the keys by one breaking into the computer terminal 60 itself.

As an additional precaution, the ICD 10 may be programmed to detect and eject interrogation signals that are short and probabilistically non-random. In other word, if an ICD received one or a series of consecutive interrogation signals which were not recognized as being in a valid form, the ICD 10 would reject the signal and fail to respond. This rejection process would frustrate a cryptanalyst's attempt to derive an ICD 10's private key by interrogating the ICD 10 with short messages and intercepting the re-encrypted response. This precaution is especially justified if the ICD 10 is adapted to communicate with devices and computer terminals foreign to the computer network 194 and its security verification system 168. This precaution may also limit the damage that could be imposed were a private key of the security verification system 168 compromised.

In step 620, if the decryption and verification failed to identify an ICD 10 having access privileges to the computer terminal 60, then the operation proceeds again-to step 608, where the computer terminal 60 waits for a predetermined period of time and, returning to step 600, transmits another interrogation signal.

Because an ICD 10 may be misplaced by or stolen from a physician, additional security measures are warranted. The security verification system 168 may be programmed to require that a physician manually enter a password at the beginning of each day. Alternatively, the system could require manual password entry at random times throughout the day, even while the physician is logged on, flagging possible theft and unauthorized use of the ICD 10 should the proper password not be detected. Further, a switch may be incorporated onto the ICD 10 to force it into a mode requiring password entry. More elaborate means, including voice identification or a fingerprint or retinal scan, could also be incorporated into the ICD 10 or at computer terminals 60 to reinforce such security. One example of a fingerprint interrogating ICD and its advantages is described in detail below. It is to be expected, however, that should a physician be dispossessed of an ICD 10, that he or she immediately notify the system security administrator to deactivate the access privileges of the ICD 10.

Provided an ICD 10 having access privileges to the computer terminal 60 has been identified, in step 624 the security verification system 168 determines whether or not to require the entry of a password to enable log on by the physician. This procedure provides a safeguard should the ICD 10 be stolen, deterring unauthorized log on attempts with the threat that the security verification system 168 will detect the breach and apprehend the violator.

If password entry is required, then in step 632 the computer terminal 60 prompts the physician for a password. Information that is entered may not only be processed by the computer terminal 60, but also transmitted to the ICD 10 in encrypted form in order to reset a flag maintained by the ICD 10 indicating that password entry is required. In step 636, the password is analyzed. If the wrong password has been entered, in step 640 a counter is incremented. If the wrong password was entered less than three consecutive times (step 640), the security verification system 168 returns to step 632 and again prompts the physician to enter the password. After three failed attempts (step 640), however, in step 644, the security verification system 168 disables recognition of the ICD 10, records the location of the failed attempt, and notifies the system administration to alert it to a possible attempted breach of the system. Other processes may be performed in the event of a failed interrogation. For example, where data is to be provided to a terminal after a successful interrogation, the terminal may block reception of transmitted data after a failed interrogation or series of interrogations.

If within the first three attempts, the correct password is entered, the operation advances to step 648, logging the physician onto the computer terminal 60 and providing access to program features and databases in accordance with the access privileges of physician. In step 652, the computer terminal queries the ICD 10 for the existence of data records to transfer to the computer network 194 and causes the ICD 10 to transmit them, if any, to the computer terminal 60 for database storage, in accordance with the operation detailed in FIGS. 16A-16F. This query for data records or information packets may be automatic or may simply be a function which periodically queries for records as described in more detail below.

After completion of the data transfer by the ICD 10 to the computer terminal 60 or, in the event no data is transferred but another terminal application (e.g. a wordprocessor) is employed by the physician, if warranted, the computer terminal 60 will continue to periodically poll the ICD 10 with recommitment signals. These recommitment signals may be specifically addressed to the physician's ICD 10 and may incorporate a different random number with each polling. Further, these recommitment signals may be encrypted with the ICD 10's public key stored by the security verification system 168, instead of or in addition to encryption by the security verification system's private key, so that they may only be intelligibly decrypted by the ICD 10 itself, using its own exclusively-guarded private key. By periodically polling the ICD 10, the user input and output devices of the computer terminal 60, including the monitor, keyboard, and mouse, can be disabled if the computer terminal ceases receiving response signals from the ICD 10. A physician may also be automatically logged out by means of periodic polling.

Figure 15C:
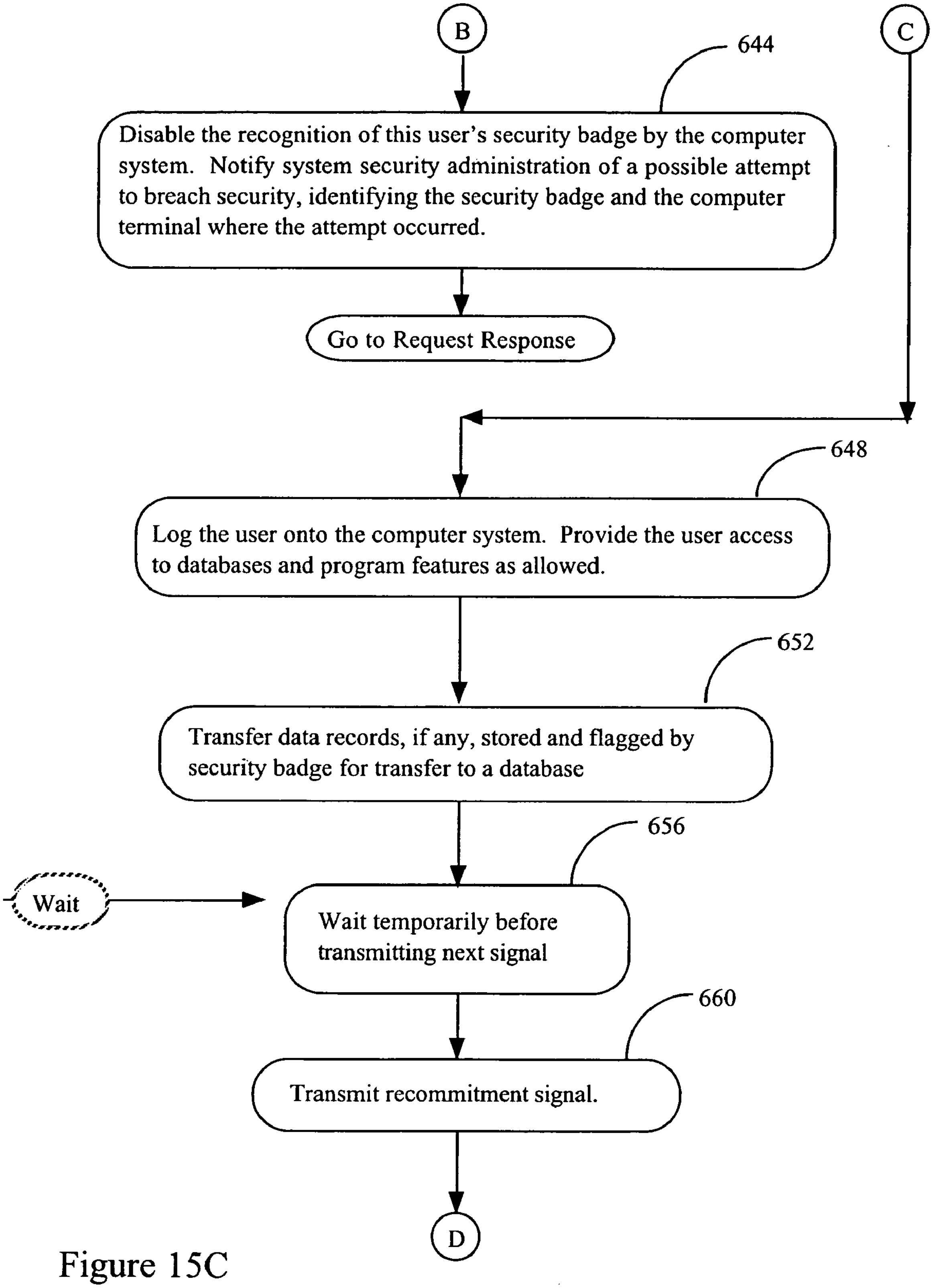
Figure 15D:
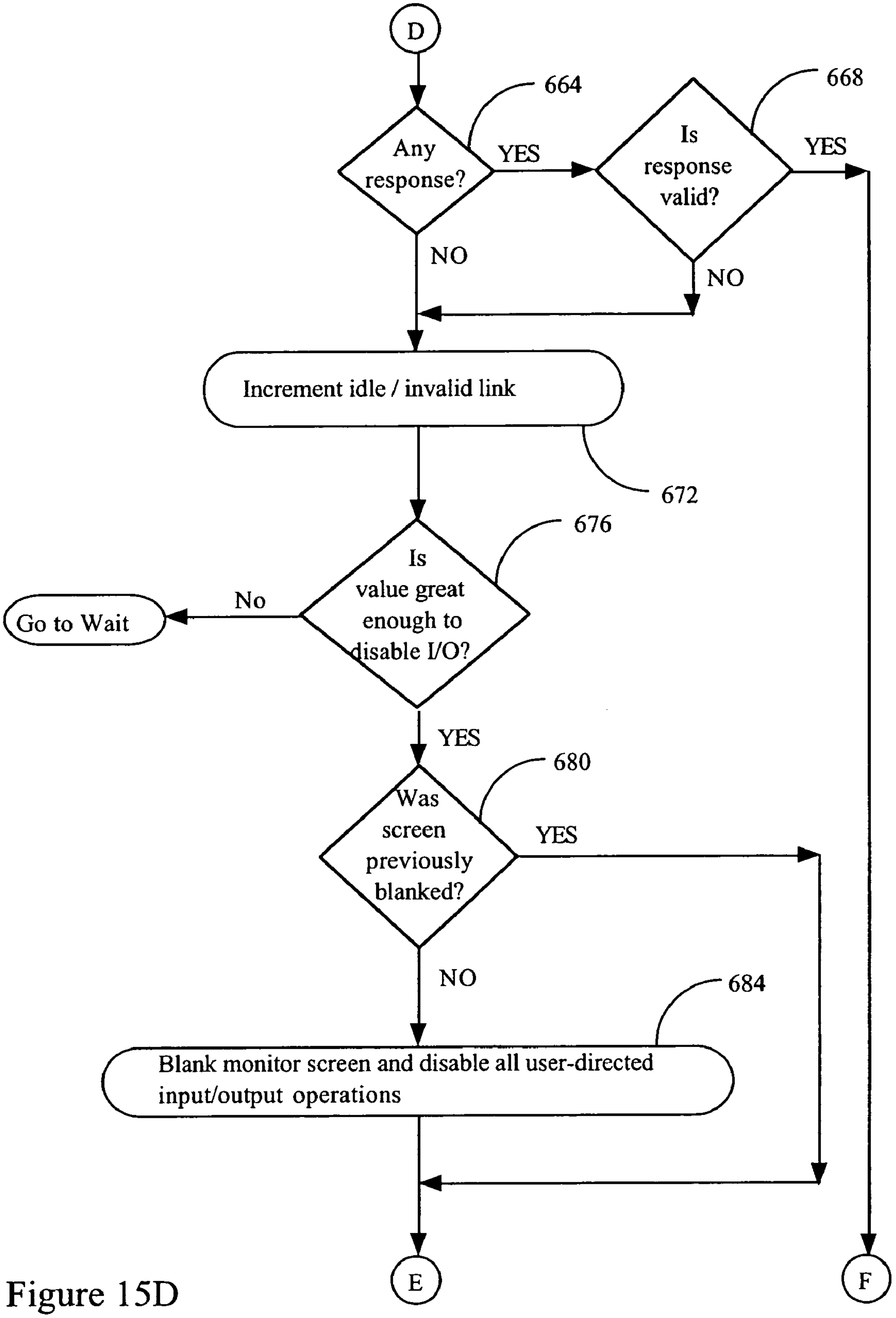
Figure 15E:
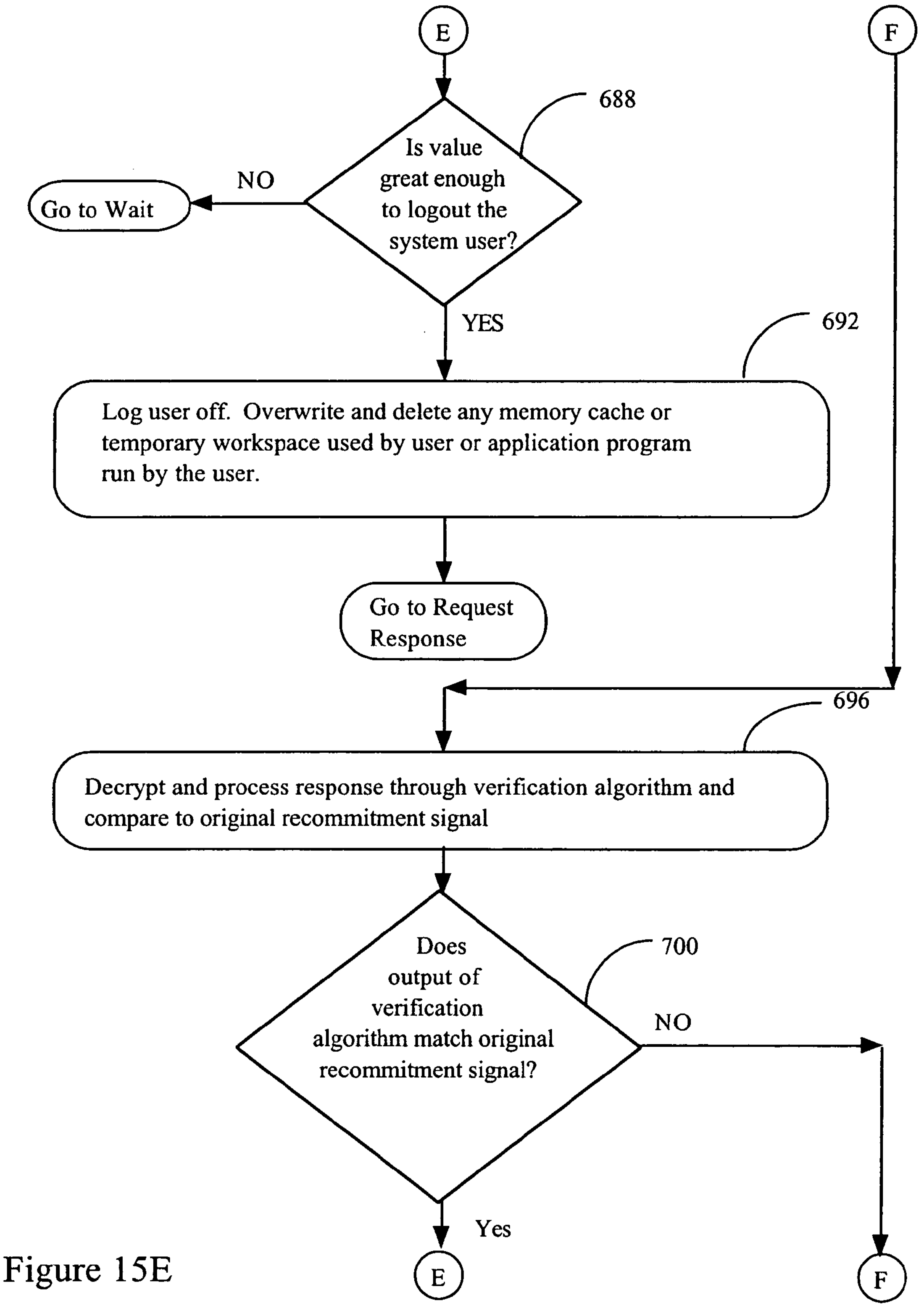
Figure 15F:
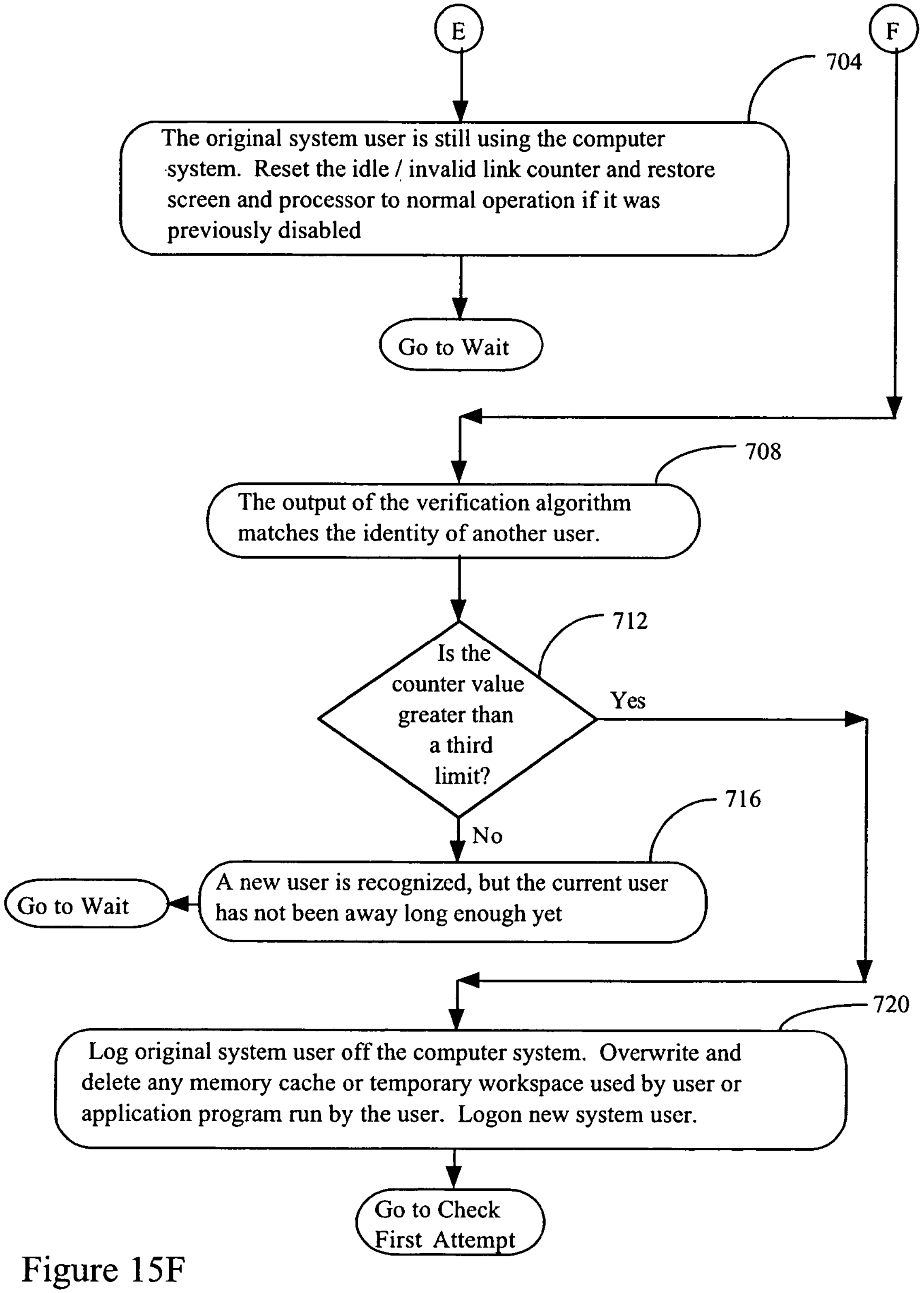
Figure 16A:
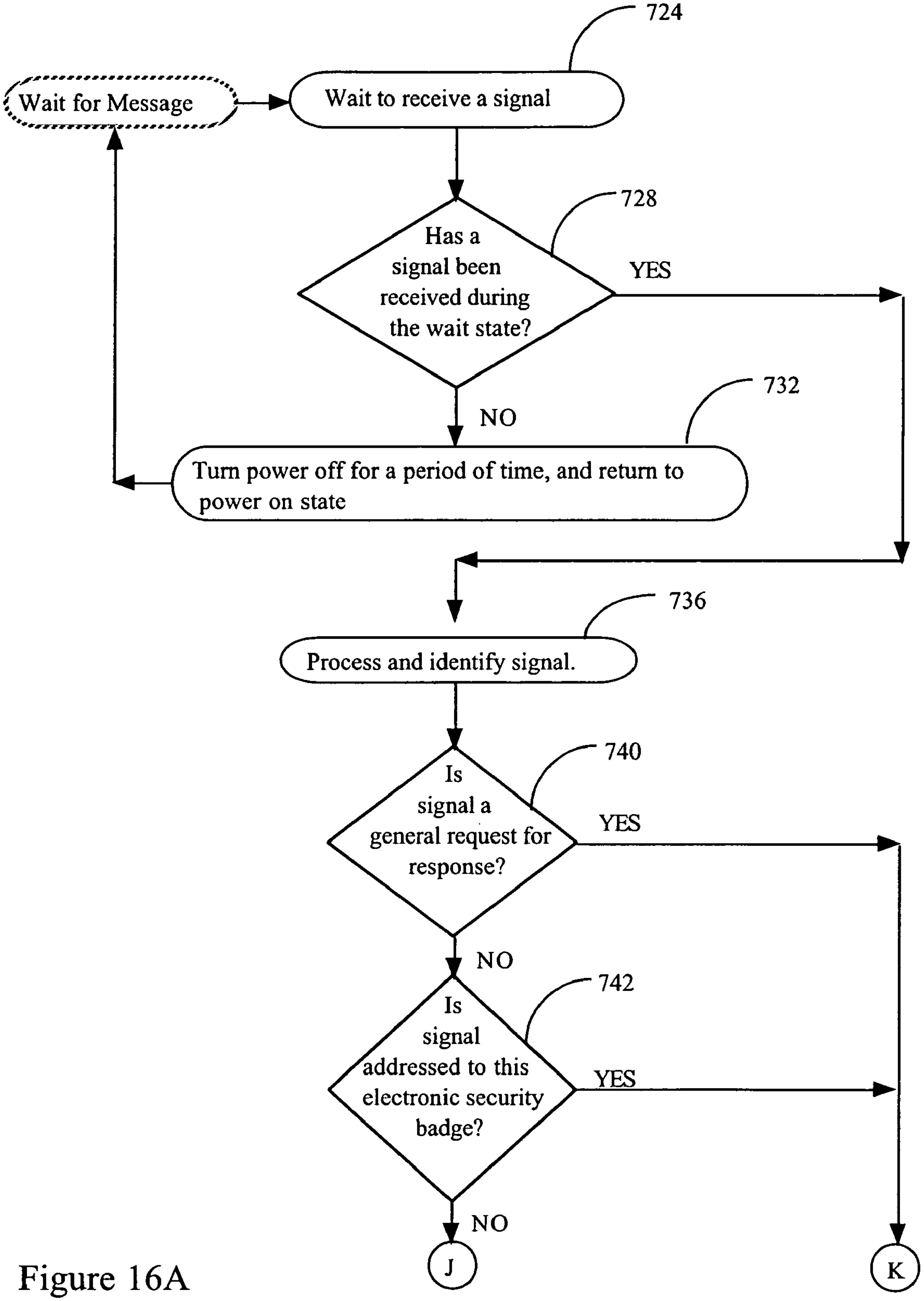
FIGS. 16A-16F are a functional flow chart showing the steps a security badge executes in logging on to a computer system, sending data, or signing a document.
Figure 16B:
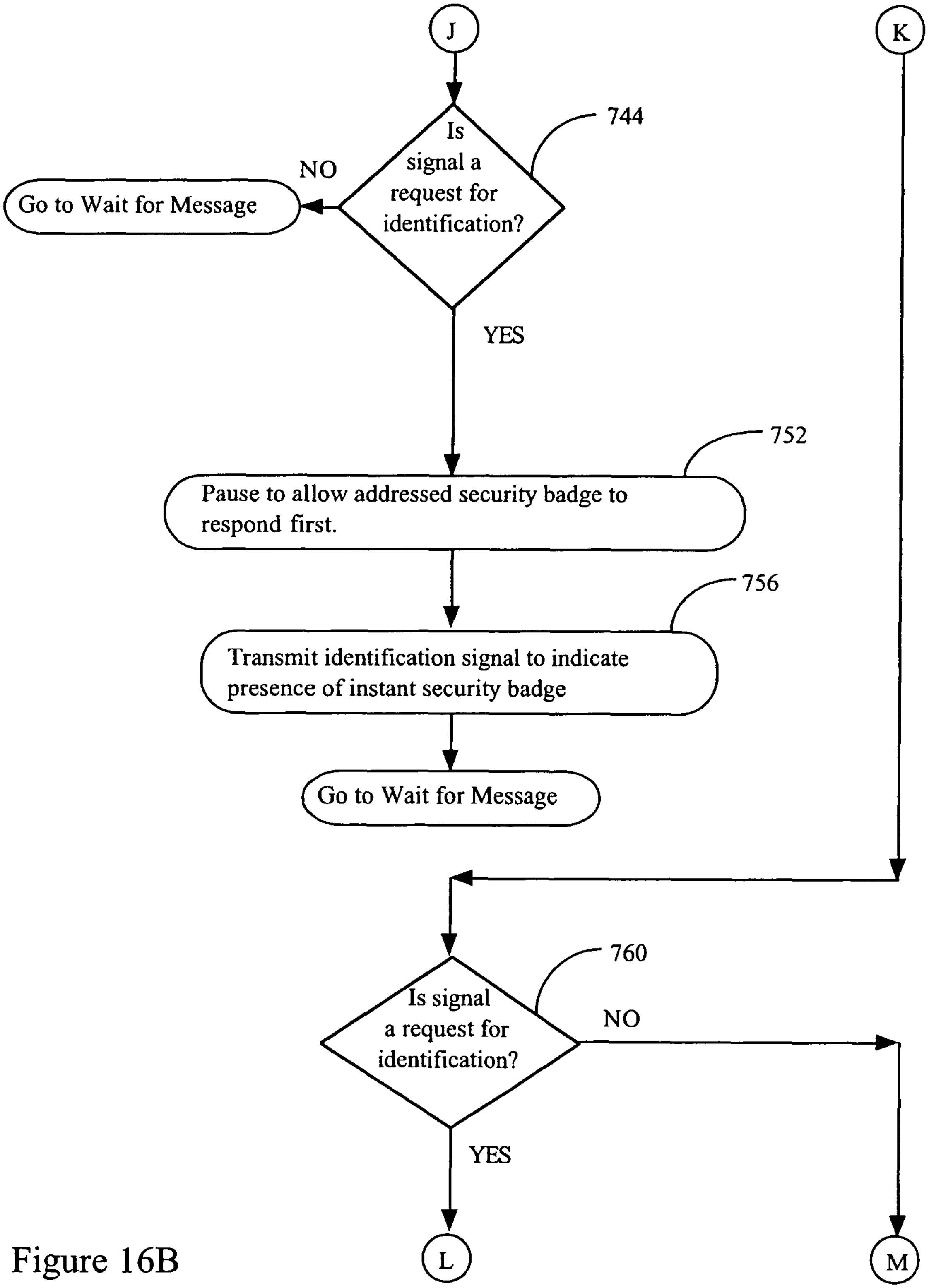
Figure 16C:
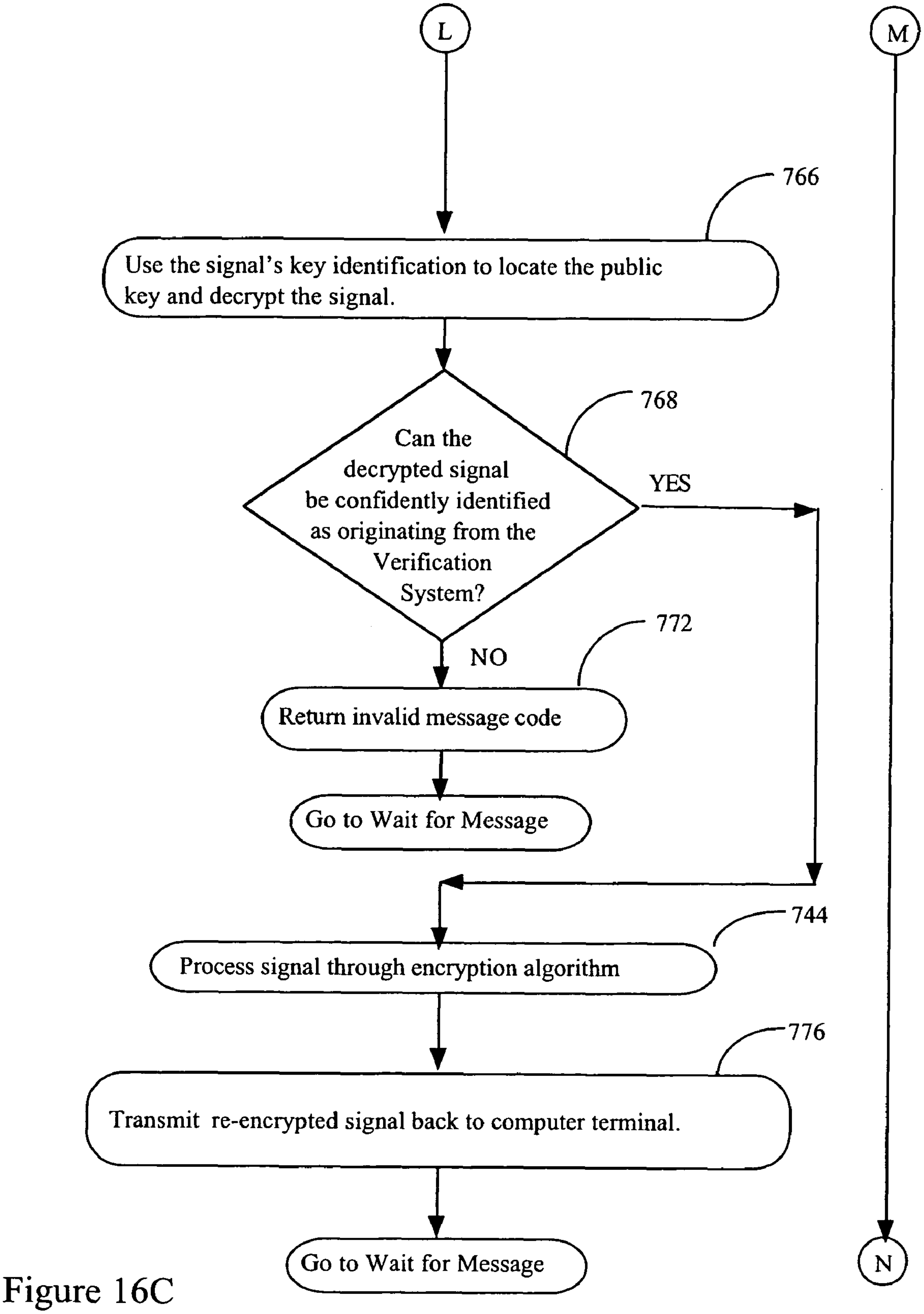
Figure 16D:
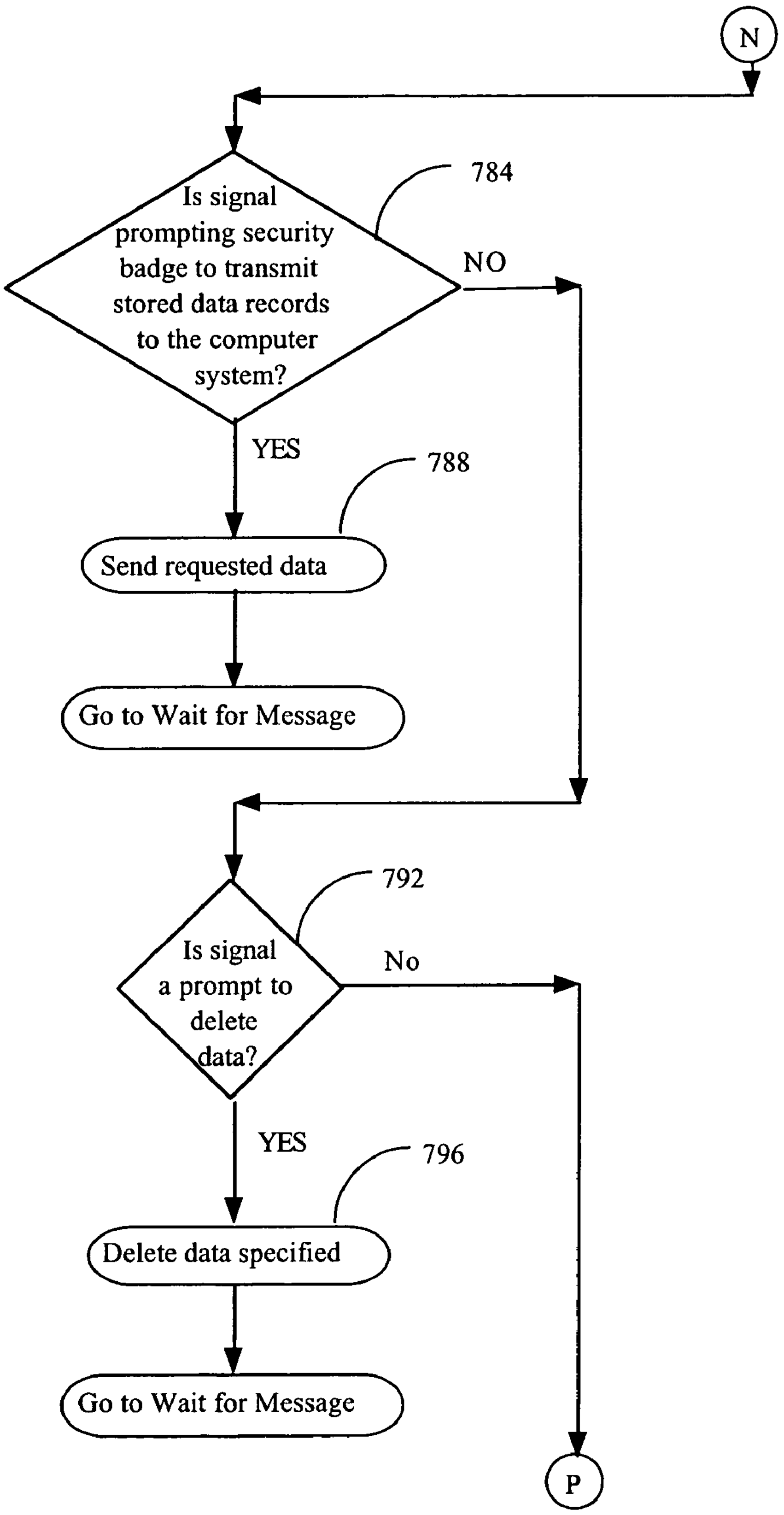
Figure 16E:
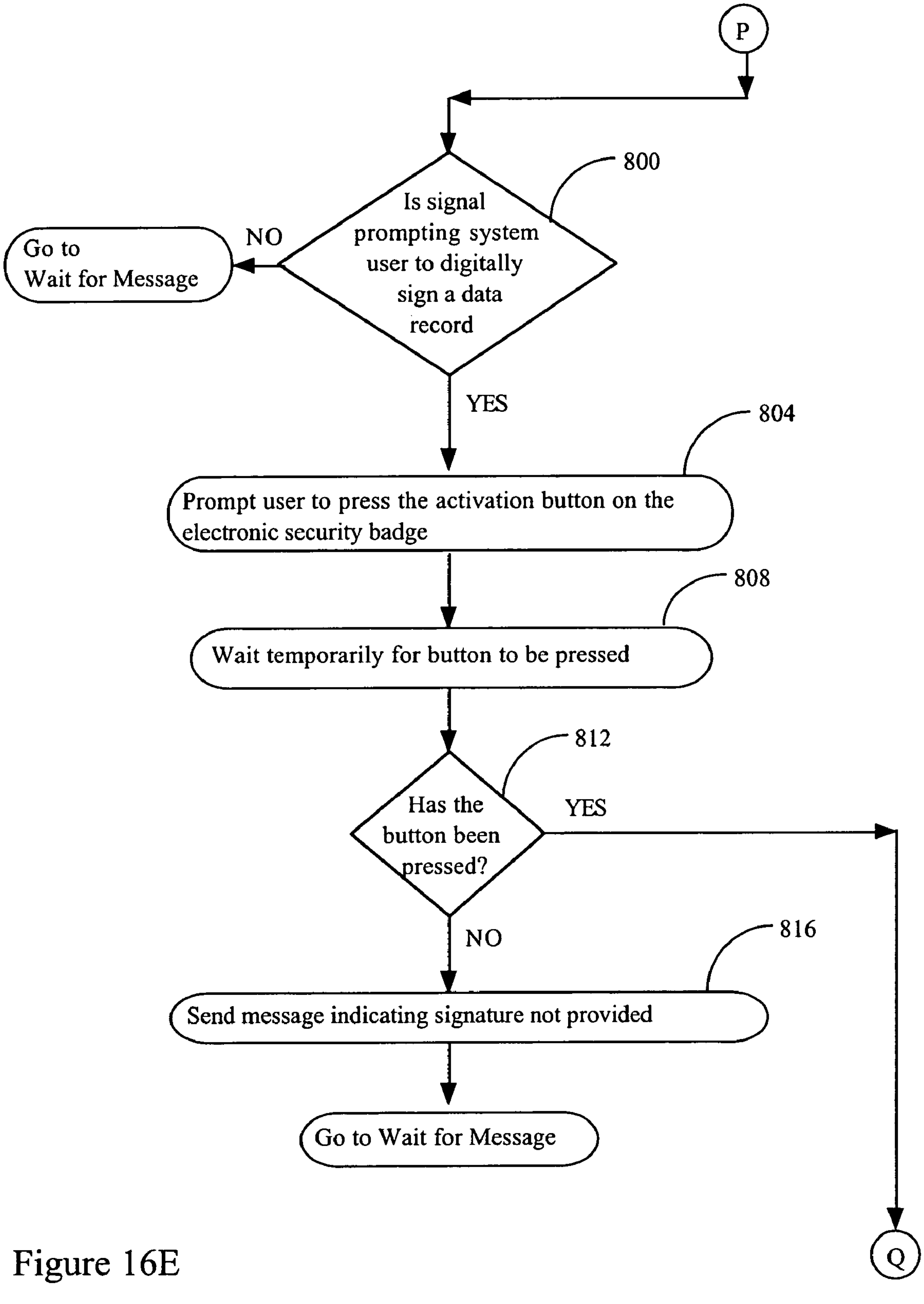
Figure 16F:
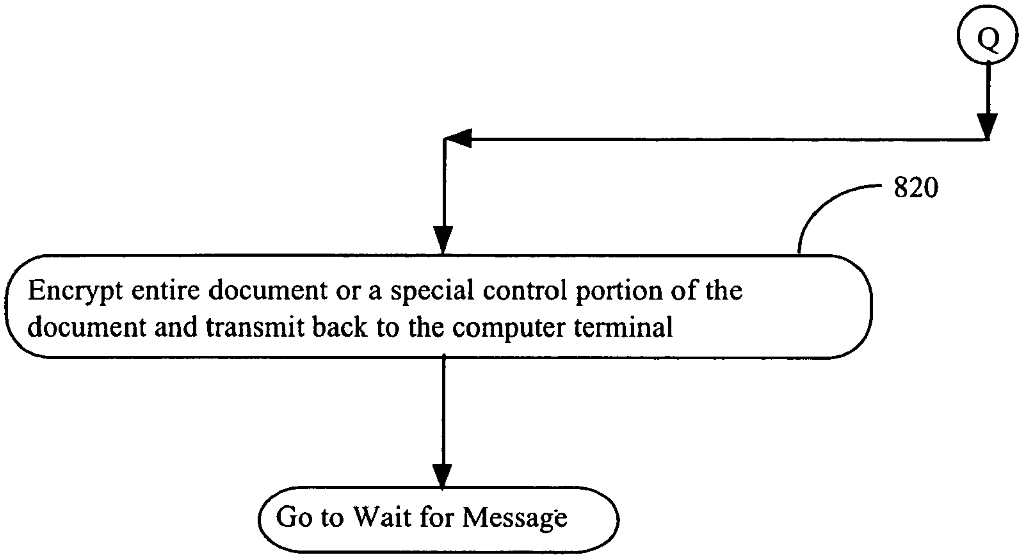

This process of periodic polling is illustrated in steps 656 through 692 of FIGS. 15C-15E. The computer terminal waits for a predetermined interval in step 656, transmits a recommitment signal in step 660, and probes for a response signal in step 664. If there is a recommitment response signal, in step 668 its content is evaluated. If the content of the recommitment response signal is accepted, the operation proceeds to step 696, discussed infra. If either there is no recommitment response signal in step 664, or if the content of the recommitment response signal is rejected in step 668, an idle/invalid link counter (not illustrated) maintained by the security verification system 168 and whose initial value relative to the log on event was zero, is incremented in step 672.

The idle/invalid link counter permits the physician to temporarily turn away from the transceiver device 64 of the computer terminal 60 or to otherwise interfere with the signal path. However, if the computer terminal 60 does not receive a recommitment response signal after several requests, the display of the computer terminal 60 is blanked, input from any keyboard or pointing device may be ignored, and other processing activities may be suspended. The computer terminal 60, however, continues to transmit recommitment signals. Should the physician's ICD 10 respond within a second period of time, the display will be restored to its previous condition and the keyboard, pointing device, and processor will resume normal operation. If the ICD 10, however, does not transmit a correct recommitment response signal during the second period of time, the physician is automatically logged off the computer network 194. When the user is logged off the computer system, a software program may also be used to remove any temporary files that have been stored on disk or in RAM memory, e.g. the cache file used by the network browser program. Furthermore, access by the computer terminal 60 to the computer network 194 may be terminated with the exception of the link between the computer terminal 60 and the security verification system 168, which may be preserved to determine if a new user is attempting to use the computer terminal 60 to log onto the computer network 194. In this manner a physician's access to the computer network 194 is restricted while logged off and enlarged while logged on.

This computer terminal access security operation is described more particularly in steps 676 through 692 of FIGS. 15D-15E. The value of the idle/invalid link counter is compared in step 676 to a predetermined disable I/O limit. If that value does not exceed the disable I/O limit, the periodic polling continues with step 656. If and when the value of the idle/invalid link counter does exceed the disable I/O limit, in step 684, the input and output devices of the computer terminal 60 are disabled, if they have not been previously disabled (step 680). In step 688, the value of the idle/invalid link counter is compared to a predetermined logout limit. Periodic polling is continued in step 656 if the value of the idle/invalid link counter does not exceed the logout limit. If and when this value is exceeded, in step 692 the physician is logged off the computer terminal 60 and information stored in memory or cache on the computer terminal by the user is overwritten.

If the content of the recommitment response signal is valid (step 668), in step 696 the security verification system 168 processes the signal through a verification algorithm, attempting to decrypt the signal with public keys and comparing the decrypted output with the original recommitment signal. If the decrypted output matches the original recommitment signal (step 700), then in step 704 the computer network 194 recognizes that the physician is still using the computer system. The idle/invalid link counter is reset and the display and other input and output functions of the computer terminal 60, if disabled, are restored. If the decrypted output does not match the original recommitment signal (step 700), then in step 708 the computer network 194 recognizes that another physician is nearby. If the value of the idle/invalid link counter exceeds a third limit (step 712), then the original physician is logged off, memory cache and temporary work space utilized by the original physician or applications executed by or through the original physician is deleted and/or overwritten, and the new physician is logged on to the computer terminal. If the value of the idle/invalid link counter has not yet exceeded a third limit (step 712), then the new physician is recognized but not logged onto the terminal, for the original system user has not been logged off for a sufficient period of time.

While the preferred embodiment is described above wherein a terminal initiates an interrogation process, the invention is not meant to be so limited and indeed includes systems wherein an ICD may initiate an interrogation either when an ICD is near a terminal (e.g. in the case where an ICD transmits interrogation signals at regular and frequent intervals) or when an initiation button is pressed on the ICD.

III. Operation of an ICD in Access Control

FIGS. 16A-16F describe the operation of an ICD 10 (FIG. 1) in responding to interrogation and recommitment signals transmitted by a proximately located computer terminal 60 (FIG. 3). In order to conserve power, the ICD 10 is preferably capable of alternating between sleep and wake states. During a sleep state, the ICD 10 is not responsive to signals transmitted by computer terminals 60 and other proximate smart devices, and may be essentially "invisible" to such devices. This alternating sleep/wake cycle is described in steps 724 through 732. In step 724, the ICD 10 maintains a wake state in which it is capable of receiving and transmitting signals through its wireless communication means 14. If in step 728, the time allotted for the wake state has expired and no signal has been received via the wireless communication means 14 of the ICD 10, then in step 732 the ICD is powered down for the allotted duration of its sleep state, before cycling back to the wake state of step 724.

If a signal is received during its wake state, however, the alternating sleep and wake-cycle is suspended in order to process and respond to the signal. In step 736, the ICD 10 processes and identifies the signal. If the signal is identified as a nonspecifically addressed signal (step 740) or as being addressed to the instant ICD 10 processing the signal (step 742), then further evaluation of the signal is performed, beginning with step 760, discussed infra.

A signal that is neither nonspecifically addressed (step 740) nor specifically addressed (step 742) to the instant ICD 10 is regarded as being extrinsically addressed to a second ICD 10. This situation may arise when two system users 68 with two security badges 10 are in the vicinity of the same computer terminal 60, one of them being logged onto the computer terminal 60. In step 744, the extrinsically addressed signal is evaluated to determine whether or not it is of a nature seeking an identification signal from the second ICD 10. If not, the instant ICD 10 ignores the extrinsically addressed signal and retires to wake state 724. If, however, the extrinsically addressed signal is of a nature requesting an identification signal, in step 752 the instant ICD 10 pauses to permit the second ICD 10 to transmit its identification signal. In step 756, the ICD 10 then transmits its own identification signal to the computer terminal 60 to indicate its presence, retiring afterward to wake state 724. This may allow the security verification system 168 to temporarily blank the screen to prevent unauthorized access to data by one physician through the access privileges of another physician. Alternatively, after repeated failures by the computer terminal 60 to receive a response signal from the second ICD 10, the second physician may be logged out and the instant physician logged in.

In the event that the signal was either nonspecifically addressed (step 740) or specifically addressed to the instant ICD 10 (step 742), the operation advances to step 760, where the signal is further evaluated to determine whether it is an interrogation or recommitment signal, in which case it would have been encrypted by a private key of the security verification system 168. If in step 760 it is identified as an interrogation or recommitment signal, then in step 764, a key ID tag appended to the signal is used to locate the public key stored in the memory element 262 (FIG. 6) of the ICD 10, with which it decrypts the signal.

In step 768, the decrypted signal is evaluated for information positively or probabilistically identifying the security verification system 168 as the source of the signal. This step implements the precaution of programming the ICD 10 to detect and reject interrogation signals that are too short or probabilistically non-random. If the decrypted signal is not distinguishable as originating from the security verification system 168, then in step 772, the ICD 10 stores and transmits an invalid message code, retiring to wake state 724. If the decrypted signal is recognized as originating from the security verification system 168 (step 768), then in step 774, the signal or a portion thereof is re-encrypted using the private key of the ICD 10 and transmitted, in step 776, to the computer terminal 60. Following this transmission, the ICD 10 retires to wake state 724.

Turning back to step 760, if the signal is not identified as an interrogation-or recommitment signal, in step 784 the signal is evaluated to determine whether it is prompting the ICD 10 to transmit stored data to the computer terminal 60, in which case in step 788 the data is transmitted before the ICD 10 retires to wake state 724. If the signal was not identified as a prompt for data transfer (step 784), then in step 794 the signal is evaluated to determine whether it is prompting the ICD 10 to delete specified data, in which case in step 796 the specified data is deleted before the ICD 10 retires to wake state 724.

If the signal was not identified as a request to delete specified data (step 792), then in step 800, the signal is evaluated to determine whether it is prompting the ICD 10 to digitally sign a document or data record using its private key. If the signal is not identified as a request to digitally sign a document, the signal is treated as an unspecified command, upon which the ICD 10 takes no action, instead retiring to wake state 724. If the signal is identified as requesting a digital signature (step 800), in step 804 the computer terminal 60 or the ICD 10, by means of its audible alerting device 20, prompts the physician to depress the activation button 18. In step 808 the ICD 10 waits for the physician to respond for a limited time period. In step 812, if the activation button 18 has not been depressed before the expiration of this limited time period, then in step 816 the ICD 10 returns a signal indicating that the signature has not been provided, retiring then to wake state 724. In this manner a digital signature will not be provided without the affirmative agreement and action of the physician. If in step 812, the activation button 18 had been depressed within the limited time period, in step 820 the document, a message digest or an information packet is encrypted in whole or in part and transmitted to the computer terminal 60, the ICD 10 afterward retiring to wake state 724.

Though not illustrated, the activation button 18 may be pressed for several seconds in order to suspend automatic log on access to a computer terminal 60 without being prompted to enter a password. The ICD 10 may emit an audible sound to indicate that automatic log on has been suspended.

In addition, while the preferred embodiment is described above wherein a terminal initiates an interrogation process, it is also possible in other embodiments to initiate an interrogation via the ICD either every time an ICD is proximate a terminal or when an earmarked ICD button is pressed.

IV. Browser Initiation

It is contemplated that the inventive ICD/smart device system will be used with conventional computer terminal hardware which can be employed to run other useful software programs. To this end, when a physician nears a terminal and the terminal and the physician's ICD 10 perform an interrogation, the physician will simply be logged onto the terminal and ICD information packets may or may not be automatically transferred to the terminal, depending on how the terminal is configured. In a preferred embodiment, after a successful interrogation, a terminal automatically queries an ICD 10 to retrieve information packets for display. In another embodiment, after a successful interrogation, a physician is given the option to use any terminal capabilities which the physician is authorized to use. For example, in addition to downloading information from the physician's ICD to the terminal, the physician may wish to use a wordprocessor or a spreadsheet, access the Internet, access e-mail and so on. In this embodiment, upon accessing a terminal, the physician is given the option to select any of several different applications. Instead of automatically querying an ICD 10 for information packets to transmit packets, a physician must press activation button 18 (see FIG. 1) at which point packets are transmitted.

In either of the above embodiments (i.e. automatic and manual packet transfer), when not using a terminal to display packet information, the terminal must be useable for other applications.

Figure 22:
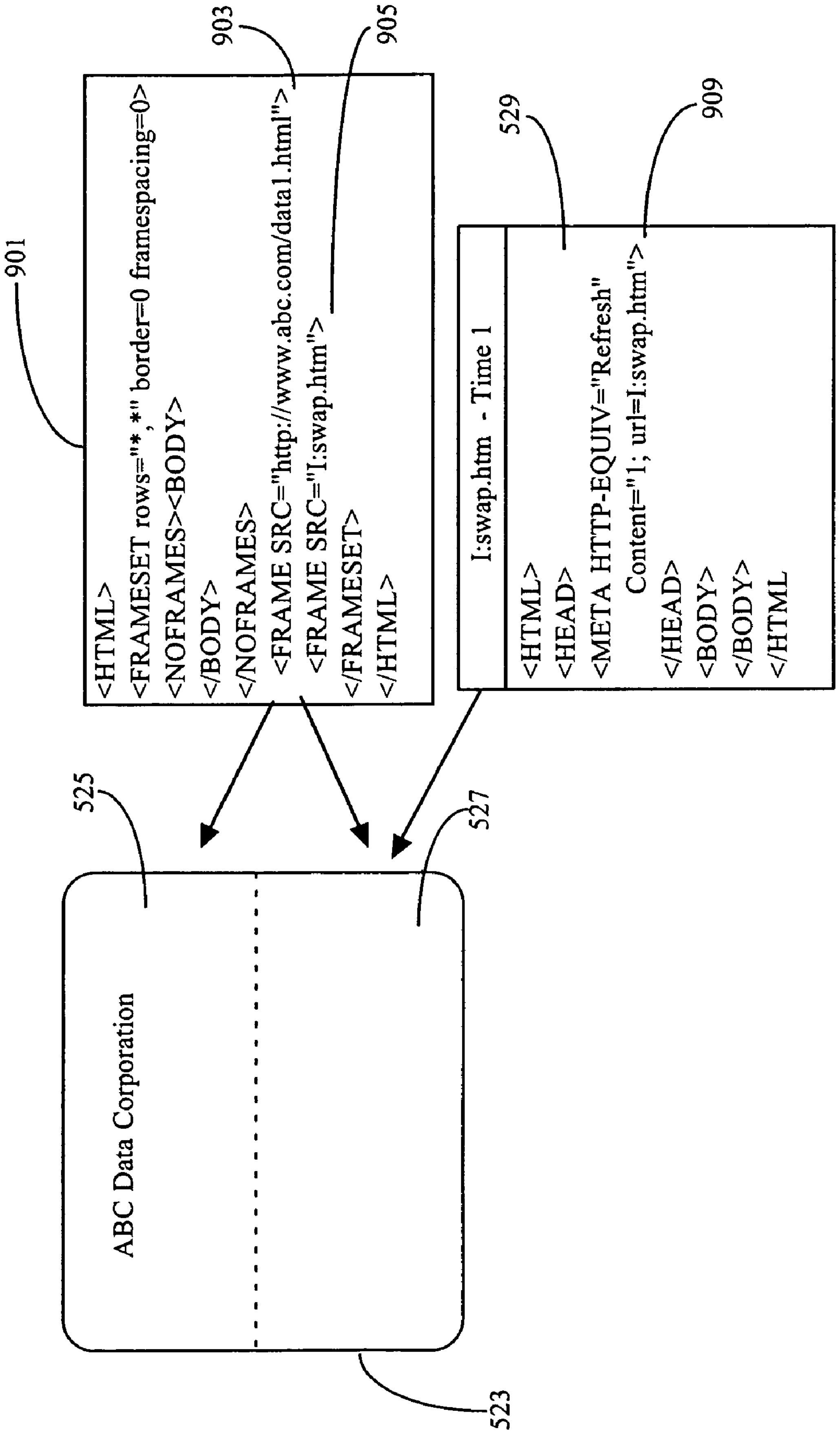
FIG. 22 is an exemplary screen view used to implement the present invention.

To enable a terminal to facilitate various applications and still be ready to receive ICD 10 data, preferably, a split screen is maintained by the terminal. Referring to FIG. 22, an exemplary split screen 523 is illustrated. Screen 523 includes an upper window 525 and a lower window 527. Although illustrated as relatively large, in reality, lower window 527 is extremely small (e.g. a single line) so that a selected application can take essentially full advantage of entire screen area 523. Generally, a selected application (e.g. a word processor) runs in window 525.

Exemplary HTML code for controlling window 525 is indicated in box 901. Lines 903 and 905 indicate that the information from www.abc.com and from address l:swap.htm, respectively, should be displayed in windows 525 and 527, respectively, wherein "l" corresponds to the address location associated with the input device and acts as a device similar to a disk drive. In window 527 code segment 529 is provided at a time 1 prior to information being provided at address l:swap.htm, Segment 529 includes a "Refresh" command 907 and a command "url=l:swap.htm". Refresh command 907 indicates that window 527 should be refreshed periodically (e.g. every 3 seconds) with data stored at address l:swap.htm. Where no data is stored at address l:swap.htm, window 527 remains relatively small (e.g. a single line at the bottom of the screen). However, upon a refresh cycle, when information has been provided at l:swap.htm, window 527 is automatically expanded such that the information can be displayed therein.

When an information packet is received from an ICD 10, either through automatic query or pressing button 18, the packet is stored at l:swap.htm which emulates a disk drive and segment 529 is the code sample in the file.

Thus, after an ICD 10 first establishes communication with a terminal, until information packet transmission to the terminal, a physician can use any of several different terminal applications in window 525. However, once an information packet is received, code line 909 expand and refresh window 527 with a screen which is configured via the received information packets.

For example, assume a physician's ICD 10 includes three patient information packets which the physician is to review via a terminal. Prior to receiving the packets, however, the physician would like to review data on ABC Corporation which is accessible via the Internet. When the physician is proximate a terminal, the terminal and ICD 10 perform an interrogation process and, after a successful interrogation, the terminal allows the physician to access the terminal. In the first embodiment (i.e. automatic packet query), the input device automatically retrieves the ten packets from the ICD 10 and stores the packets on disk address l. The next time (e.g. within 3 seconds) screen 532 is refreshed, the browser displays a screen configured accordingly to the packets stored at address l:swap.htm.

Figure 24:
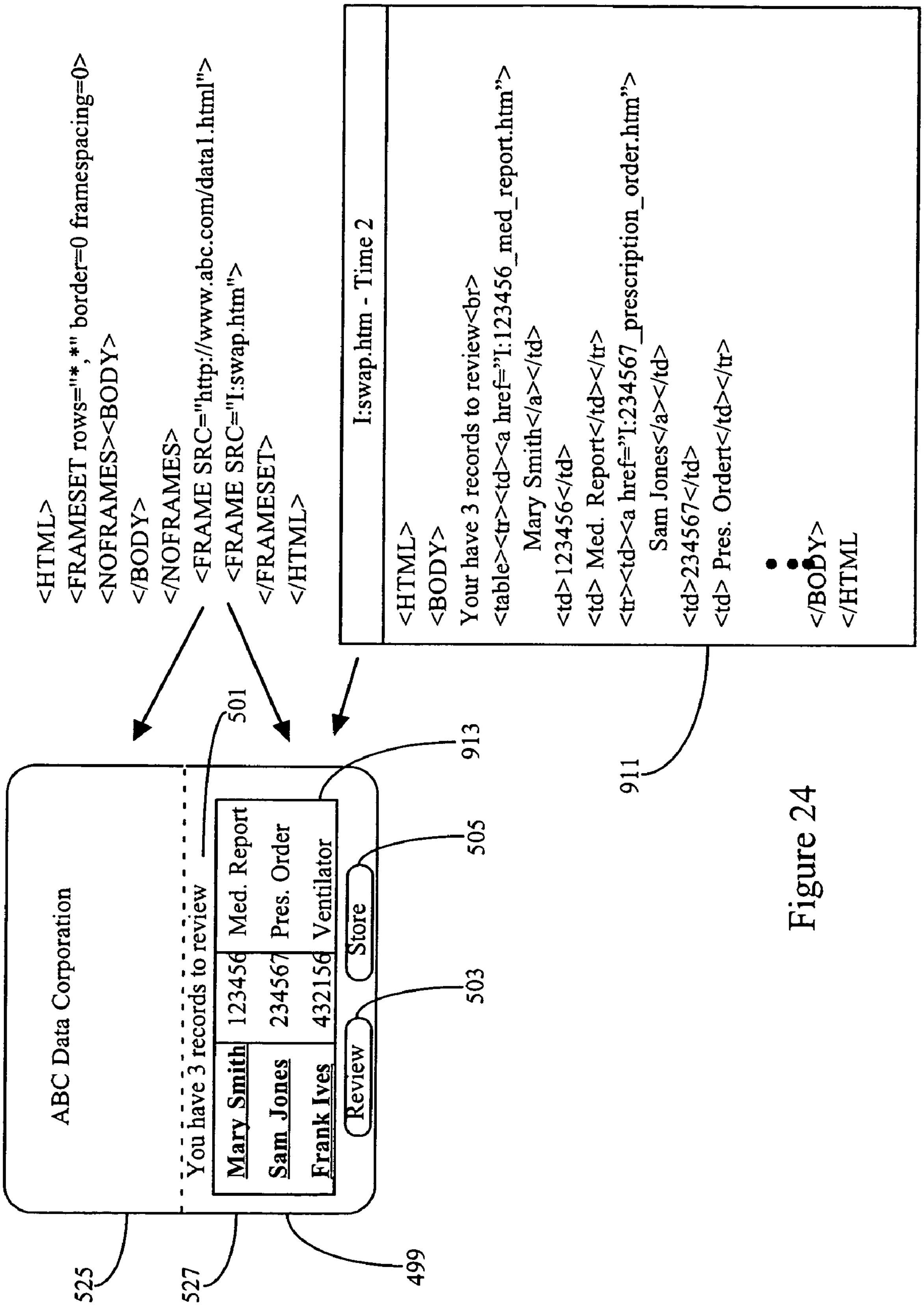
FIG. 24 is a screen view illustrating an initial screen according to the present invention.

Referring to FIG. 24, an exemplary HTML code segment 911 which may be provided at a time 2 to address l:swap.htm via an ICD 10 and a resulting terminal screen 499 are illustrated. Segment 911 expands window 527 and reduces window 525 and provides three different types of information including a summary phrase 501, separate record or information unit summaries in a table 913 and interaction icons 503 and 505. Phrase 501 summarizes table 913 information and in the example indicates there are three records to review. Table 913 presents the records to review in summary form. The interaction icons include REVIEW and STORE icons 503, 505, respectively.

Either of icons 503 or 505 may be selected using a mouse controlled cursor (not illustrated). Because the physician wishes to first use the Internet to access ABC Corporation data, the physician selects STORE icon 505 which stores the packets on a terminal or network memory device for later review. Thereafter, screen 523 (see FIG. 22) is redisplayed, including expanded window 525 and reduced window 527 (see FIG. 22). Window 527 waits for additional packets on drive 1. In window 525 a personal menu of icons representing applications for the accessing physician is provided, one of the selectable icons corresponding to the physician's Internet account. The physician selects the Internet icon, reviews ABC Corporation data and can then return to an application which allows review of the stored packets.

Referring to FIGS. 1 and 22, in the second embodiment where packets are not transmitted until button 10 is pressed, when a physician gains access to a terminal, screen 523 is initially displayed, the physician's personal menu of application icons displayed in window 525. In this case, the physician selects the Internet icon, reviews the ABC Corporation information and then closes the Internet application.

At any time while the physician maintains access to the terminal, the physician may press button 18 to transmit information packets to the terminal. When button 18 is pressed, packets are sequentially stored to and at l:swap.htm and then provided to the terminal. Upon the next refresh cycle (e.g. 3 seconds), an initial screen (see FIG. 23) characterizing the packets and providing options is provided.

V. Interrogating ICD

Figure 23:
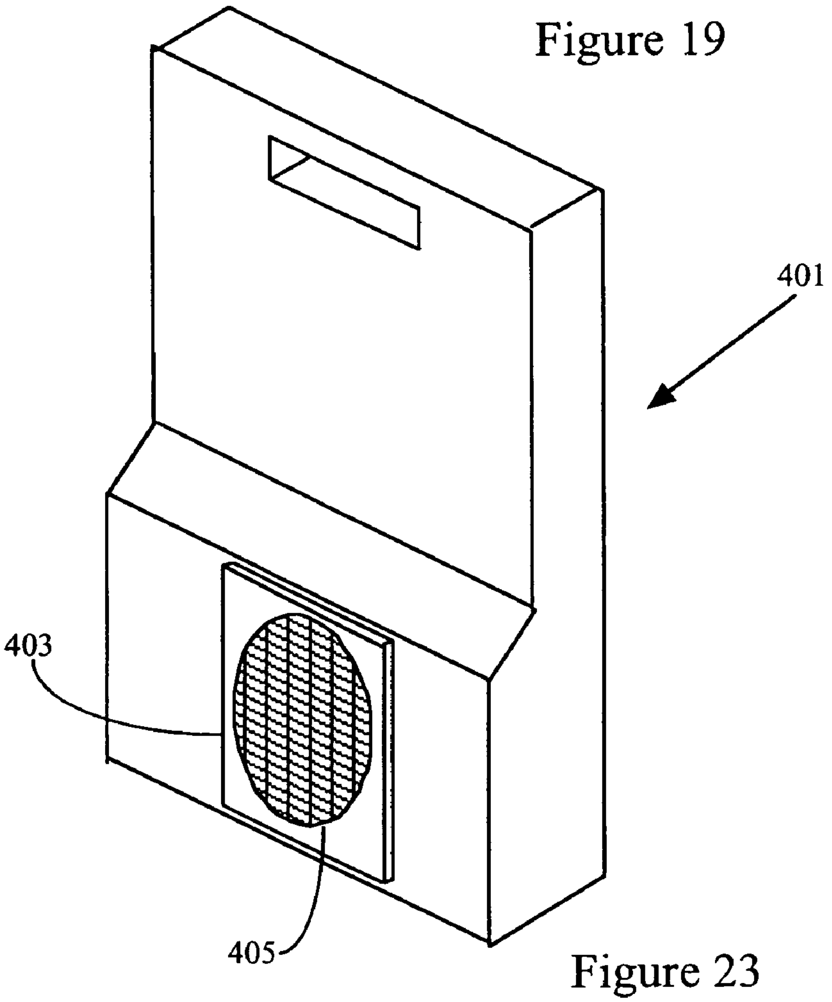
FIG. 23 is a perspective view of a preferred embodiment of the badge illustrated in FIG. 1.

Referring now to FIGS. 1 and 23, a preferred embodiment of the ICD badge 10 is identified as ICD 401. ICD 401 is essentially identical to ICD 10 (FIG. 1) having the same internal components, an alarm indicator, a speaker, an audio digitizer, a transceiver, a visual indicator (e.g. picture, text, etc.) and so on. However, ICD 401 is different than ICD 10 in that the activation mechanism is different.

FIG. 23 is a perspective view of ICD 401 showing, generally, the back side of ICD 401, the front side of ICD 401 appearing as illustrated in FIG. 1. Instead of having a conventional activation button (26 in FIG. 1), ICD 401 includes an interrogating activation button 403 which includes a finger print pad 405 which is approximately the size of a thumb. Pad 405 is capable of discerning the characteristics of a fingerprint when a thumb is pressed thereon. Various systems for discerning fingerprint characteristics have been provided in the prior art and therefore will not be explained here in detail. Suffice it to say that any method for discerning characteristics may be used here which can be implemented in a relatively small electronic package. Pad 405 is linked to the ICD processor (see FIG. 6) and provides print characteristics to the processor for interrogation.

Because each ICD 401 is an identification badge, each ICD 401 is uniquely associated with a single physician. Therefore, when an ICD 401 is initially provided to the physician, the physician commissions the ICD 401 by placing the physicians thumb on pad 405 a first time. During a commissioning protocol, the first time a thumb is placed on pad 405, the ICD processor discerns fingerprint characteristics and stores the discerned characteristics in an ICD memory (see FIG. 6). In addition to storing fingerprint characteristics, the ICD processor is equipped with code for comparing fingerprint characteristics and based on the comparison, for either allowing ICD functions to be performed or disabling ICD 401.

To this end, prior to ICD 401 being used for any information gathering, transmitting, generating or interrogating purposes, a physician must place her thumb on pad 405 pressing button 403. With her thumb on pad 405, the ICD processor again discerns fingerprint characteristics and compares the discerned characteristics with the stored characteristics. Where the discerned and stored characteristics are essentially identical, ICD 401 is enabled. Upon a match ICD 401 may either be programmed to be enabled for one transaction or a certain number (e.g. 10) of transactions or, in the alternative, may be enabled for a specific time period or, where ICD 401 is used to perform a transaction within a specific time window, may remain enabled for a subsequent period.

Where the discerned fingerprint characteristics do no match the stored characteristics, ICD 401 may do any of several different things. First, ICD 401 may simply disable itself until an authorized facility administrator resets the ICD 401 for another identification attempt. Second, ICD 401 may allow several (e.g. 3 or 4) attempts to generate a match and only after several failed attempts disable itself. Moreover, when ICD 401 disables itself, ICD 401 may either cause an audible or a visual signal indicating a mismatch and may continue to cause the signal to alert passersby that an unauthorized person attempted to use the ICD 401.

ICD 401 is uniquely advantageous for a number of reasons. First, ICD 401 ensures that only a specific physician associated with ICD 401 can use ICD 401 for collecting, generating, and transmitting information and for interrogating other smart devices. This is particularly important, as will become clear below, in instances where successful interrogation enables a physician to perform some procedure or to administer some drug. For example, one example explained in more detail below allows a physician to open a drug container (see FIG. 5) only after a successful interrogation is completed between the container and an ICD 401. The interrogation is meant to ensure that the user of ICD 401 is authorized to administer the drug inside the container. While the interrogation provides one level of security, there is no way to ensure that a physician's ICD 401 will not be misplaced or stolen in an attempt to mismedicate a patient. With ICD 401, even if the ICD 401 is stolen, a would be mismedicator could not open a drug container unless the physicians fingerprint could also be duplicated.

Second, while other systems for identifying personnel via fingerprint or other biometric indicia are prevalent in the prior art, many such systems require that users "give up" control of their indicia by providing the indicia to a system administrator. For example, a security system for restricting access to an office building may include a security server and a plurality of fingerprint pads located at building entrances and perhaps at other doors located throughout the building. The security server has access to a memory storage device where fingerprint characteristics corresponding to each person who has authority to access the building are stored. To enter a building, a person places her thumb on a pad, the pad discerns fingerprint characteristics which are provided to the server and the server compares the characteristics to all sets of fingerprint characteristics which correspond to personnel who have authority to access the building through the specific door. Where discerned characteristics match a stored characteristic set, the building allows entry. If the discerned and stored characteristics do not match, the building restricts entry.

Unfortunately, with the system described above, each of the people whose fingerprint characteristics are to be examined during an access attempt must agree to provide their fingerprint characteristics to the security server to enable comparison. While providing such biometric indicia is not difficult, many people object to giving and only grudgingly give, such information as they feel that type of information is private. Clearly, if every building a person entered would have to have personal biometric indicia, peoples biometric information would be virtually everywhere.

Another problem with such a system is that, like a door handle, many (e.g. hundreds and even thousands) people may be placing their thumbs on a single fingerprint thumb pad every day. Such access to the pad not only seems unsanitary but in fact is unsanitary as germs are spread via the pad.

With the inventive ICD 401, all personal biometric indicia remains personal and does not have to be "given up" to some administrative server. This is because ICD 401 and not some amorphous server, performs the interrogation and enables ICD 401 to operate. Thus, personal biometric indicia is never accessible by a device outside a physician's own ICD which the physician controls to at all times.

In addition, with ICD 401 only the physician who "owns" ICD 401 will be placing her thumb on pad 405 unless some mistake is made. Thus, ICD 401 is relatively sanitary.

Another advantage of ICD 401 is that, because ICD 401 is only useable by a single physician, only a single set of fingerprint characteristics have to be stored by the ICD processor and discerned characteristics during an interrogation need only be compared to a single set of stored characteristics. These advantages cut down both on required memory and processor time necessary to complete an interrogation which means that ICD 401 need only have a relatively simple processor.

It might also be noted that while the fingerprint pad activation button has been described in the context of ICD 401, clearly this aspect of the present invention could be used in many other technical areas. For example, in the case of a building entry security system as described above, a smart card may be provided which is similar to ICD 401 except that, upon enablement, the card may only be able to unlock a door. In this case, to open a locked door, first, a user places her thumb on a smart card fingerprint pad similar to pad 405 (see FIG. 23). The pad discerns print characteristics and provides those characteristics to a card processor. The processor compares the characteristics to a stored characteristic set corresponding to the card owner. Only if the stored and discerned characteristics are essentially identical will the card be enabled to unlock the door. When the card is enabled, rather than indicating the fingerprint characteristics to the security server, the card sends out an identification signal to a receiver (e.g. RF or infra-red) which provides the identification signal to the server. The server then compares the identification signal to stored valid identification signals to determine if the received signal corresponds to a person who is authorized to open the door. The door is only opened if a match occurs. In this manner a security system which uses personal biometric indicia can be provided without requiring users to give up control of their indicia.

Moreover, the fingerprint pad activation button could also be used in the context of a credit card to enable or disable a credit card on the basis of a simple fingerprint check as described above with respect to the access card. To this end, to charge a purchase, a user places a thumb on a pad, a comparison is performed and, only when a match occurs is a purchase authorized.

While the inventive pad activation button has been described above in the context of a fingerprint pad, the invention is not meant to be so limited and any other recognizable biometric indicia or uniquely personal biomedical indicia could be used to activate a properly configured activation button. For example, a retinal scanner, voice recognition identifier skin texture identifier, etc., could be used to activate a button and so on.

VI. Operation of an ICD in Collecting Data

Figure 17A:
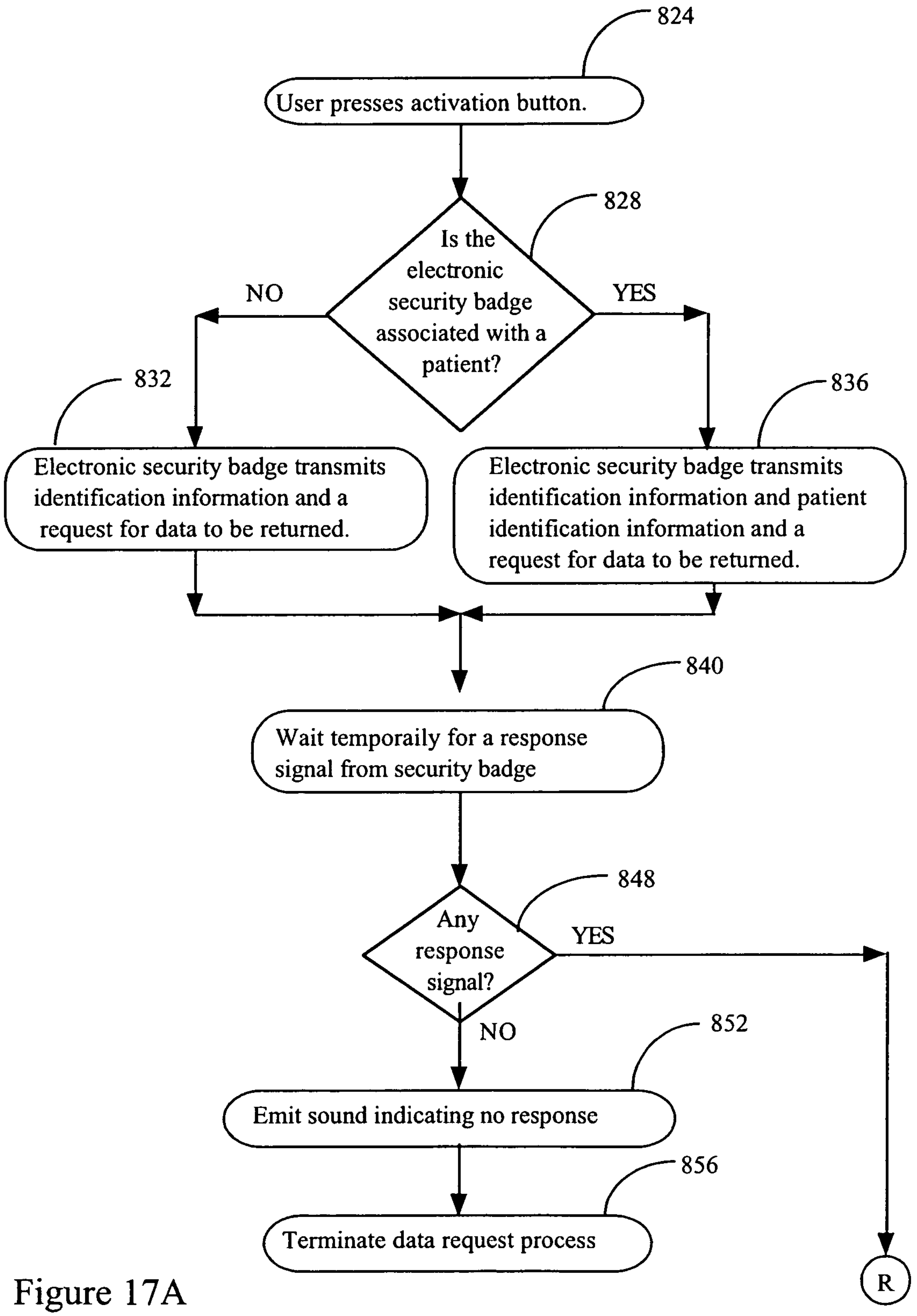
FIGS. 17A-17C are a functional flow chart of the steps a security badge executes in establishing an association with a patient and acquiring data from other computerized devices.
Figure 17B:
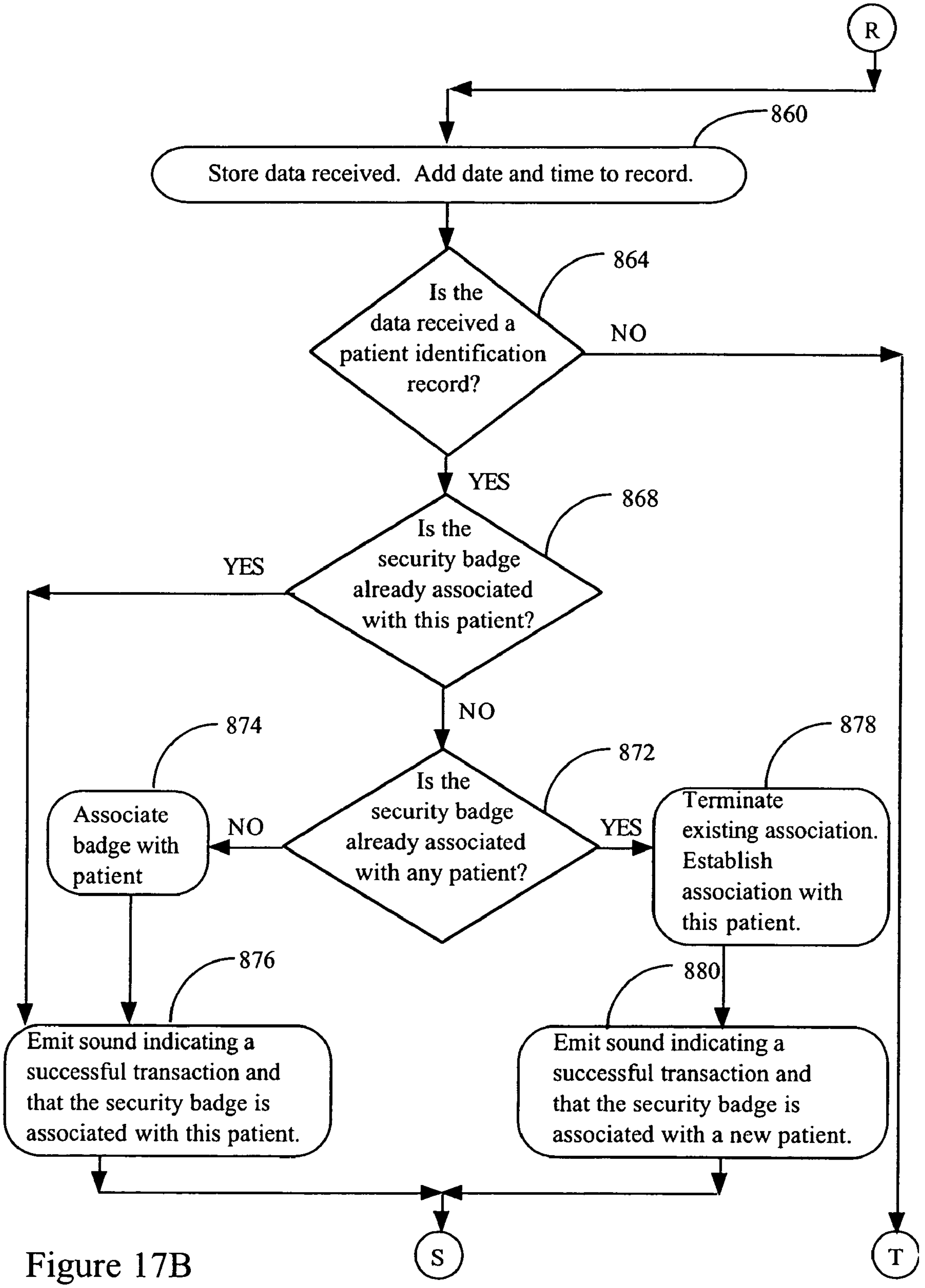
Figure 17C:
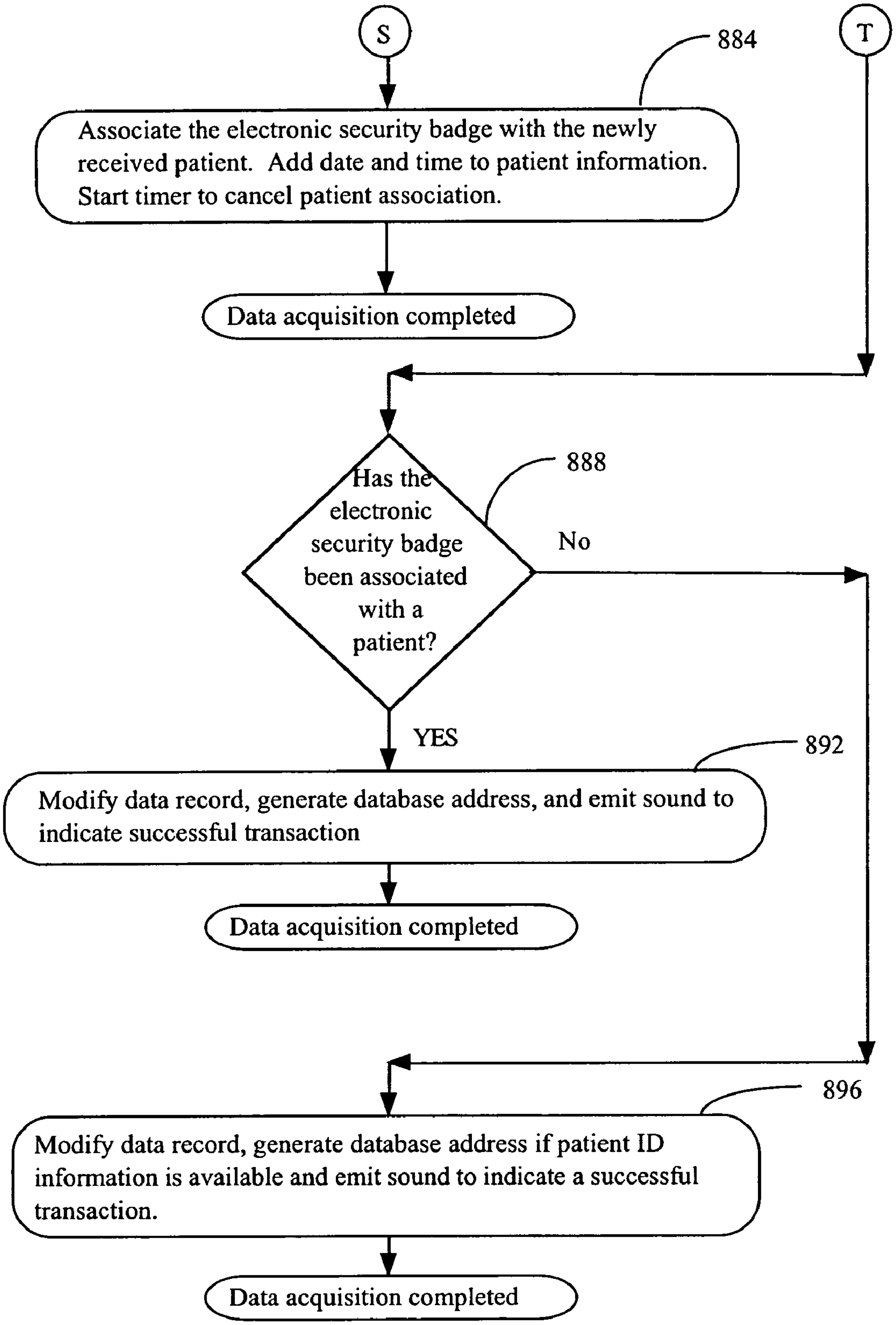

FIGS. 17A through 17C describe the operation of an ICD 10 in gathering and exchanging data with smart devices with which ICD 10 is in communicable range. This operation is described particularly, but not by way of limitation, in the context of a hospital, where the exchange of information between ICD 10 and a plurality of smart devices assigned to various patients and distributed throughout the hospital may be limited by the access privileges corresponding to patients whom or with whom a physician is authorized to diagnose, treat, or interact. Referring again to FIG. 4, a single hospital room 104 (FIG. 4) may include a number of smart devices, including a computer terminal or workstation 60, a patient identification display 100, a bedside communication device 96, a patient treatment device 116', and a patient monitor 80', each of which may communicate with the ICD 10 or, in some circumstances, with each other.

Generally, smart devices like bracelet 40 (see FIG. 2) or container 200 (see FIG. 5) include information about a patient or a medical event and/or generate information about a medical event, the included or generated information being stored as one or more information segments in respective device memories. When a physician decides to collect information from a smart device, the physician establishes communication between the device and the physician's ICD 10 and causes the smart device to transmit stored information segments to ICD 10. For the purpose of this explanation, the term "data record" is used to describe a grouping of information which is to be transferred among system devices and may include a simple information segment or a more complex construct such as an information packet referenced above and described in more detail below.

When ICD 10 receives one or more information segments, ICD 10 recognizes the nature of the segments and stores related segments as an information unit in HTML format. In addition, ICD 10 may also generate other information segments which can be added to received segments to provide enhanced information units. Exemplary additional segments may include a time and date stamp generated by badge processor 250 (see FIG. 6) and physician identifying information (where available).

Moreover, ICD 10 also provides two other types of information. First, ICD 10 includes an address specifier (i.e. the ICD processor) which provides a server target address for each information unit formed. The target address specifies a specific server or database address to which the information unit should be sent for storage or processing on system 194 (see FIG. 7). Second, ICD 10 also provides browser formatting information which indicates how browser 115 should present information in an associated information unit on display 103.

For each information unit browser 10 assembles an information packet which includes the information segments in each unit, an associated server address and relevant configuration information. Importantly, each information packet assembled by an ICD 10 is in HTML format so that the packet can be received by a conventional browser 115 for display.

Subsequently, after a physician has gained access to a terminal 60 (see FIG. 3), the physician causes information packets assembled by the physician's ICD 10 to be transmitted to the terminal 60 via an input device 64. The packets are received and read by browser 115. Browser 115 displays information unit information in the format indicated by the configuration information and stores the relevant server target address.

In addition to indicating how information unit information is to be configured on display 103, configuration information may also provide on-screen tools for modifying some or all of the unit information displayed. For example, where displayed information specifies a medication dose which was supposedly delivered to a patient, while the displayed dose may indicate the dose dispensed by a pharmacy, upon administration, a physician may have elected to modify the dose. In cases where such modifications can be anticipated, the configuration information provides a tool (e.g. a pull down window) for modifying the displayed dose prior to storing the unit information.

Moreover, the configuration information may also facilitate hyper links to additional information which is related to displayed information. For example, again, in the case where a medication is dispensed, displayed information will typically include the dispensing physician's name. In this case, the configuration information highlights the physician's name 464 and provides a hyperlink address "behind" the physician's name to a biography site specifying information about the physician. Similarly, a patient's name or identification number may be linked to a medical history record for the patient via hyperlink 445.

After a physician reviews and perhaps modifies displayed information packet information, the physician approves the information by selecting an approval icon 476 on display 103. When icon 476 is selected, browser 115 causes an "electronic signature" to be attached to the approved information in a manner described in more detail below. Thereafter, browser 115 sends the approved information to the server target address for storage and/or processing.

In the preferred embodiment, data exchange between an ICD 10 and a smart device associated with a particular patient is conditioned upon, and must be preceded by, establishing an "association" between a physician using an ICD 10 and the patient with whom a smart device is associated. Preferably, an association is digitally recorded by the ICD 10 in the form of information uniquely identifying the patient, the smart device and/or the ICD 10 itself, and the time and date of the association. This information may later be appended to information packets exchanged with smart devices and computer terminals 60, providing information packets with a complete audit trail. Further, smart devices and ICDs 10 themselves may also digitally record associations in a similar fashion.

Referring to FIGS. 1 and 17A, at step 824, a physician attempts to initiate a communication link or exchange information with a smart device by placing the physician's ICD 10 proximate a smart device and pressing ICD activation button 18 (FIG. 1). Depending on the sophistication of ICD 10 and the smart device and the sensitivity of the information to be exchanged, the communication established with the smart device may or may not utilize public key cryptography. While link initialization may be automated rather than user-initiated, making the links user-initiated allows ICD 10 to conserve energy and prevents unnecessary link initialization with devices with which a physician is not concerned. Alternatively, the smart devices may be individually and manually enabled to communicate through the use of activation switches incorporated in the smart devices. Provided that the signal path between an ICD 10 and a smart device is substantially unobstructed and short enough that signal transmissions are not excessively attenuated, a communications link is established.

In step 828, ICD 10 evaluates the existence, if any, of an association between the ICD 10 and any patient (not necessarily the particular patient to which the linked smart device is directed). An association exists if ICD 10 has most recently been used with a smart device which is associated with a patient. In this case, ICD 10 stores information specifying a specific patient. For the purposes of this explanation it will be assumed that the identifying information comprises a patient's identification number which, if an association exists, is stored as an identification information segment by ICD 10. Thus, to determine if an association exists, ICD 10 determines if an identification information segment is occupied. If there is no association, in step 832 ICD 10 transmits to the smart device its own identification information and a request for information to be returned. If there is an association, in step 836 ICD 10 transmits its own identification information, patient identification information (of the patient with whom ICD 10 is associated), and a request for data to be returned.

Steps 832 and 836 are each followed by step 840, in which ICD 10 waits for a predetermined time period for a response from the linked smart device. If no response is received within the predetermined time period (step 848), then in step 852 ICD 10 emits a first audible sound to alert the physician that no response was received from the smart device. In step 856 the operation initiated by the physician in step 824 is terminated. If instead a smart device transmits a response in the form of a recognizable information segment which is received before the predetermined time period elapses (step 848), then referring also to FIG. 17B, in step 860 the data record or information segment contained in the response signal is stored. In addition, referring also to FIG. 6, processor 250 identifies the time and date via clock 254 at which the information was received and stores a time stamp as a second information segment, combined with the received information segment, as an information unit.

One type of information segment or data record which may be transmitted to an ICD 10 is a patient identification record. An exemplary record is illustrated in FIG. 9 and includes an identification number, name and distinguishing characteristics. All or only a small part of the information illustrated may be included in a transmitted record but at least the identification number is transmitted.

If the data record or information segment stored in step 860 is a patient identification record (step 864), and if ICD 10 is already associated with the patient indicated by the record (step 868), then in step 876 ICD 10 emits a second audible sound readily distinguishable to the human ear from the first audible sound of step 852, signaling to the physician that ICD 10 is associated with the patient and that the exchange of information was successful.

If the data record or information segment recorded in step 860 is a patient identification record (step 864), but ICD 10 is not associated with any patient (steps 868 and 872), then in step 874 ICD 10 records the patient's identification number in the identification information segment to establish an association and in step 876 emits said second audible sound.

If the information segment recorded in step 860 is a patient identification record (step 864) identifying a first patient, but ICD 10 is associated with a second patient (steps 868 and 872), then in step 878 the association with said second patient is closed and a new association is established by recording the first patient's identification number in the identification information segment. In step 880 ICD 10 emits said second audible sound twice to indicate the closure of a previous association and the initiation of the current association.

If the data record information segment recorded in step 860 is not a patient identification record (step 864) but if ICD 10 is already associated with a patient (step 888), then in step 892 the data record is modified. In this regard, the received information segment is combined with the current identification information segment (i.e. the segment which identifies the patient with which ICD 10 is currently associated) and perhaps other information segments to form an information unit (i.e. an enhanced data record). The other information segments may include a time stamp segment, a physician segment and so on. The information segment received and other information segments which identify both the physician and the patient (i.e. the identifying information previously recorded in establishing the current association between ICD 10 and patient) are combined to form an information unit. Further, the ICD 10 emits said second audible sound to indicate the successful transaction.

If the data record or information segment recorded in step 860 is not a patient identification record (step 864) and if ICD 10 is not currently associated with a patient (step 888), then in step 896 the data record is modified to include identification information attributable to the physician to which ICD 10 is assigned. To this end, the received information segment is combined with a physician information segment which identifies the physician and perhaps other information segments (e.g. a time stamp) to form an information unit. Further, the ICD 10 emits said second audible sound to indicate the successful transaction.

Although not illustrated by flow chart, association of ICD 10 with a patient may be manually terminated by depressing activation button 18 for a few seconds, after which ICD 10 emits an audible sound to indicate that the association has been terminated. An association with a patient may also be automatically terminated after a sufficient period of inactivity with respect to ICD 10.

FIGS. 14A and 14B illustrates an exemplary HTML coded information packet 440 which corresponds to a medication dispensation event and which is provided by an ICD 10. Packet 440 may be provided in any of several different ways.

First, packet 440 may be constructed by ICD 10 as ICD 10 receives certain types of information. In this case, ICD 10 is provided with packet configuring software which recognizes information segment type and thereafter tailors a specific packet for the received segment.

Second, packet 440 may be constructed primarily by some other network device and provided to ICD 10. For example, referring again to FIG. 7, dose dispenser 150 dispenses medication for administration. The type of information generated during administration is often very similar (e.g. time, date, type, dose, patient ID, physician ID, etc.). In this case, dispenser 150 may provide a general packet format to a medication container (see FIG. 5) which is in turn provided to ICD 10 when a drug is administered.

Third, a smart device (e.g. an IV pump) may provide a general packet format including target address along with data provided to an ICD 10.

In FIGS. 14A and 14B, packet 440 includes a target address field 444 which specifies a server address to which packet information is to ultimately be delivered. The exemplary target address includes a hospital name, an event type ("mediation") an event specifier ("given"), a patient identification number ("987654321"), an event date and an event time. Packet 440 also includes a report type indicator 448, a field 452 for indicating that patient ID has been verified and format medication quantity fields and 456 and 460 indicating how much of the dispensed medicines was administered. To this end, fields 456 and 460 are set up so that, initially, each format field 456, 460 causes the medicine dose dispensed to be displayed. In addition, fields 456 and 460 provide interaction tools for modifying the displayed dose to reflect actual administered doses. Thus, field 456, which corresponds to Penicillin dose, allows a physician to modify an initially displayed dose of 2 capsules by selecting either 1.5, 1, 0.5 or none as the actual administered dose. Similarly, field 460, which corresponds to Tylenol dose, allows choices of 1, 0.5 and none to identify administered dose.

Packet 440 also includes a physician identification field 464, and a date and time field 468 indicating time of medication administration. Packet 440 further includes a dispenser identification field 468 indicating the physician who dispensed the specific medication, the date and time of the dispension and so on. Hidden fields 472 which incorporate information to be transmitted along with information to be displayed but concealed from view through the browser display, may also be added. Information appropriately concealed may include initial quantities of medication dispensed, which information may be compared with the amount actually administered. Packet 440 further includes an approve field 476 which specifies configuration of an APPROVAL icon on display 103. The APPROVAL icon allows a physician to approve of information displayed via browser 115. When field 476 is displayed and an associated icon is selected via browser 115, information in packet 440 is transmitted for storage to a database 158 or 162 at the server target address indicated in field 444.

Figure 14C:
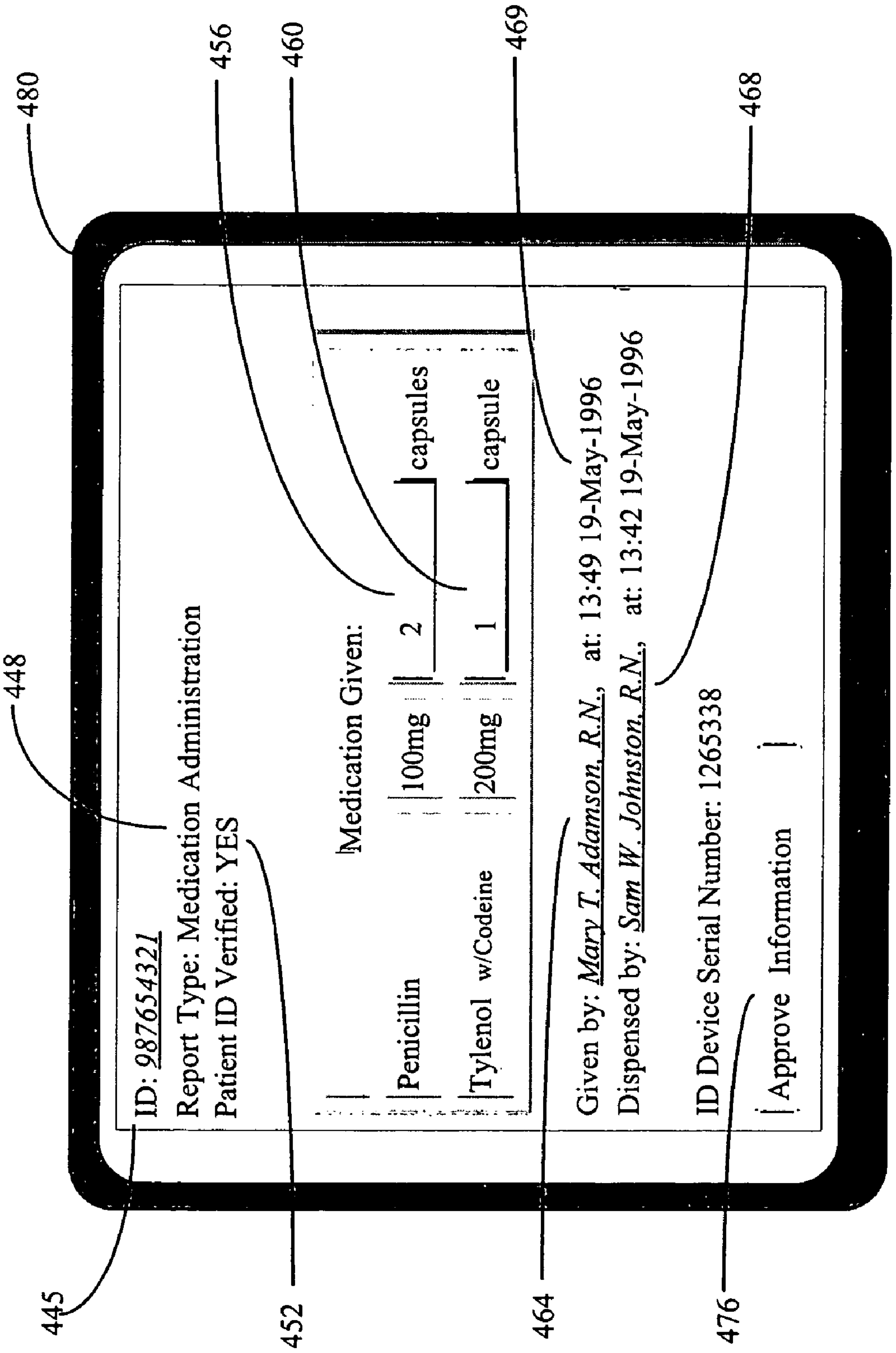
FIG. 14C is a graphical representation of the record of FIGS. 14A and 14B as it would be viewed by a system user through a network browser.

Referring also to FIG. 14C, an exemplary browser screen 480 which corresponds to packet 440 is illustrated. Screen 480 includes a plurality of elements which indicate all information associated with a drug administration event. The elements, which correspond to identically marked fields in packet 440 (see FIGS. 14A and 14B), include an identification element 445, a report type element 448, an ID verification element 453, modifiable dose elements 456 and 460, an administrating physician identification element 464 including date/time 469, a dispensing physician identification element 468, and approval icon 476. When formatted data packet 440 is transmitted to a terminal 60, the ICD 10 may be programmed to emulate a file structure device, wherein the open file command of the browser 480 may be used to request data from the ICD 10.

Thus, generally, ICD 10 formats an information packet (i.e., in the present example, a medication administration record) for delivery to network system 194 via a computer work station 60 which includes three types of information. The three information types include general information (including, perhaps identification information) to be stored, a target server address (i.e. a target address field) at which the general information is to be stored and browser screen configuration information (i.e. format fields) indicating how the general information to be stored should displayed for review, modification and approval by a physician.

Figure 18:
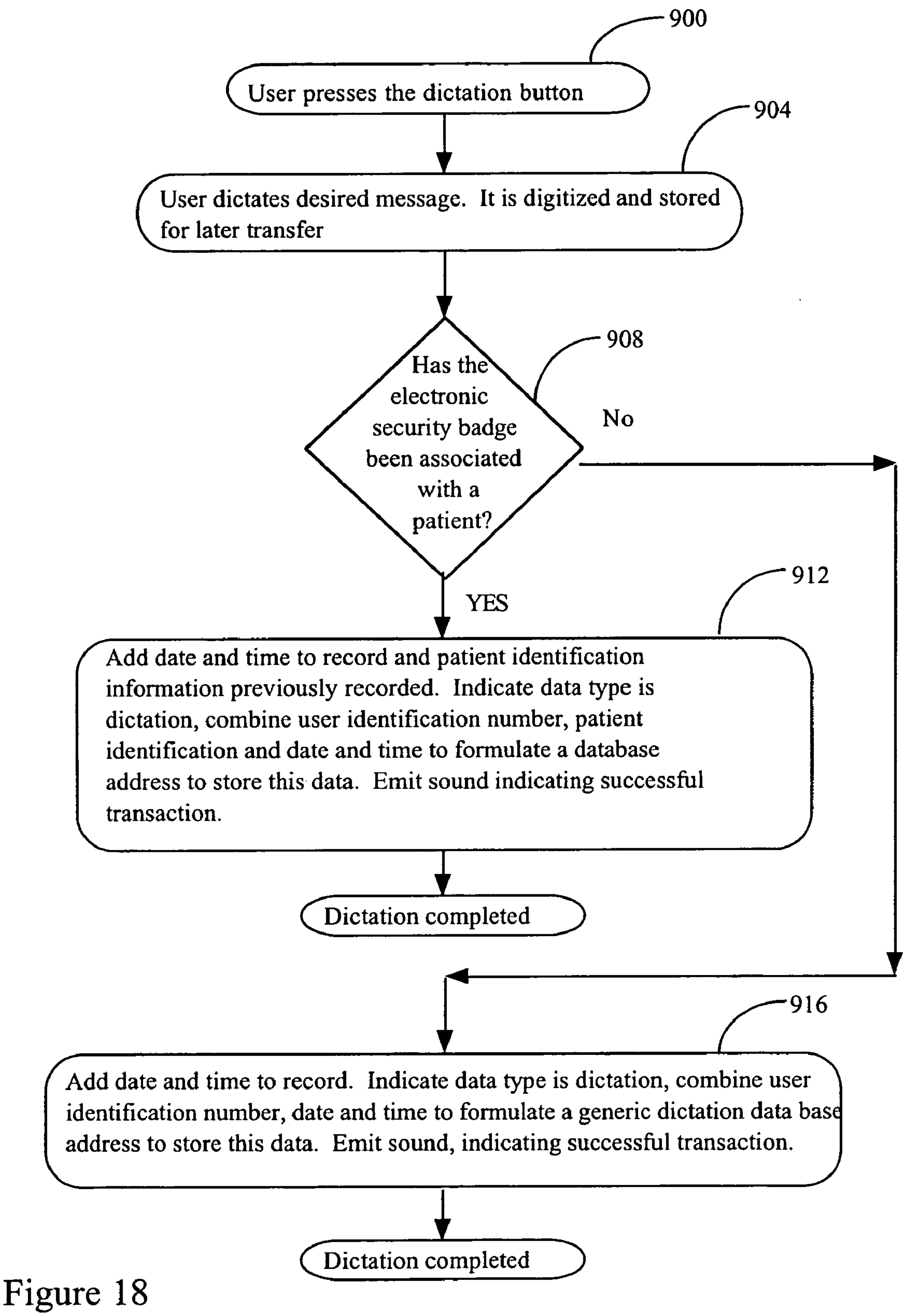
FIG. 18 is a function flow chart of the steps a security badge follows to record and generate addresses for dictated messages.

In addition to receiving information from a smart device, ICD 10 is also capable of receiving dictation for storage in one or more information units for delivery to system 194. Referring to FIGS. 1 and 18, while observing or treating a patient, a physician may, in step 900, press dictation button 26 and dictate messages (step 904) into microphone 22 of ICD 10. Digitizing circuitry incorporated in processing circuitry 260 (FIG. 6) digitizes the message (step 904), which is recorded as a message record or dictation information segment in memory element 262. If ICD 10 is associated with a patient at the time the dictation is recorded (step 908), then in step 912 patient identification information and a time stamp are incorporated into the message record. To this end, ICD 10 combines the identification information segment, the time segment and the dictation information segment into an information unit. Further, in step 912 a database address or server target address is formulated for the information unit using the time stamp, the dictation data type and patient identification information. Further, in step 912 the ICD 10 emits said second audible sound. If the ICD 10 is not associated with a patient at the time the dictation is recorded (step 908), then in step 916 a time stamp segment is added to the dictation information segment to form an information unit. Further, in step 916 the dictation data type and time stamp are combined to form a partial database address for the information unit. Further, in step 916 the ICD 10 emits said second audible sound.

Dictation information is treated like any other gathered information in the sense that ICD 10 formulates an information packet including a segment associated with the collected information. The only difference is that the collected information is digital audio. It is contemplated that when a packet includes a dictation segment, ICD 10 will construct a packet including a field which will provide a "Dictation" icon associated with the dictation segment, the icon being displayed when the packet information is reviewed via browser 115. When the dictation icon is selected, the dictation associated therewith is replayed via terminal 60 for physician review. In addition, other icons for controlling dictation review (i.e. fast forward, reverse, stop, pause, etc.) may be configured via packet configuration information.

In addition, it is contemplated that in many instances both statistical information and audio dictation may be collected during a single patient visit. In this case, ICD 10 may do one of two things. First, ICD 10 may formulate a single message packet which includes all collected information and appropriate browser configuration information. In addition, in this case, if appropriate, ICD 10 may be programmed to, generate more than a single target address for all of the packet information or, different target addresses for the various types of packet information. For example, while a dictation segment should be transmitted to a transcription server for conversion to text (either manually or automatically by voice recognition software), medication administration information should be provided to the pharmacy server for logging and to determine if proper administration occurred. Either all information could be provided to both the transcription and pharmacy servers or only relevant information may be provided to the respective servers.

Second, where more than a single type of information is collected during a single patient visit, ICD 10 could be programmed to formulate two separate information packets for delivery to a terminal 60, a separate packet corresponding to each information type. For instance, in the example above, one packet may be formulated for dictation while a second packet is formulated for statistical information. While various packet schemes are possible, the preferred scheme provides only a single information packet for each patient visit which would include all types of information collected. This scheme has the advantage of maintaining a complete record for each patient visit which can be stored in a patient's historical records to memorialize all aspects of this visit. Then, if specific servers require specific collected information (e.g. dictation, administration, administering physician, etc.), a central server can determine which information should be sent to each specific server.

In addition to generating specific information packets for transmission to browser 115, ICD 10 is preferably programmed to construct an initial screen packet. The initial screen packet, like other information packets is formatted in a conventional language such as HTML so that, when received by browser 115, browser 115 can display packet information as specified. The initial screen packet will typically include information which summarizes other packets to be transmitted to a terminal 60 and configuration information. For example, where ten information packets are to be transmitted to a terminal 60, the summary information may simply indicate "There are 10 patient records to review." The configuration information indicates how the summary information should be displayed, may provide instructions and typically provides icons for physician interaction. Exemplary icons include a "REVIEW" icon and a "STORE" icon. An exemplary initial screen 499 is illustrated in FIG. 24 and includes a prompt phase 501 and icons 503 and 505.

Referring to FIG. 3 when ICD information packets are transmitted to a terminal 60, the initial screen packet is also transmitted. The input device 64 receives all packets, distinguishes the initial screen packet from other packets, stores the other packets in RAM 109 and provides the initial screen packet to browser 115 for display. Browser 115 displays an initial screen (see FIG. 24) corresponding to the initial screen packet providing interaction icons REVIEW 503 and STORE 505.

If REVIEW icon 503 is selected, browser 115 accesses the first packet in RAM 262 and displays associated information as configured by the packet. After review of the first packet browser 115 displays record packet information and so on. If STORE icon 505 is selected, browser 115 stores the initial screen packet along with associated other information packets in RAM 109 (or some other suitable storage location) for later review and approval.

Other aspects, not included in FIGS. 17A through 17C, may be involved in communicating with or between certain smart devices. In one embodiment, the presence of a physician in proximity to a patient enables communication between the patient's wrist bracelet 40 (FIG. 2) and the physician's ICD 10. The communication link may be initiated by pressing the activation button 18 on the ICD 10 and/or an activation button (not illustrated) on the wrist bracelet 40, provided there is a complete signal path between the ICD 10 and the wrist bracelet 40. Once a communication link is established, ICD 10 identifies the patient and records the establishment of an association with that patient. ICD 10 may also request and receive additional information stored by the wrist bracelet 40, providing a beep, vibration or other sensational signal to indicate a successful transmission or to alert a physician. The wrist bracelet 40 may also record in its own memory the staff identification information and current date and time from the ICD 10 to provide an audit trail of the physicians who have associated themselves with the patient. If communication and association is established with another wrist bracelet 40 or, if not, after a preset period of time has elapsed, the ICD 10 regards the association to have terminated and alerts the physician to this fact with another beep, vibration or other sensational means of communication.

In another embodiment, the wireless communication means 52 of wrist bracelet 40 (FIG. 2) may utilize alternate communication means, such as magnetic coupling or low power radio transmission, rather than the preferred infrared means of the ICD 10. Similady, the bedside communication device 96 (FIG. 4) of a patient bed 88 may also utilize alternate communication means. Further, the communication range of wrist bracelets 40 or other smart devices may be limited in order to prevent two devices from receiving the same request. Instead of communicating directly with the ICD 10, the wrist bracelet 40 may communicate with patient identification display 100 directly or indirectly via communication with the communication means of a bedside communication device 96. A patient identification display 100 may also have transceiver device 64 compatible with the communication means 14 of the ICD 10. The smart devices may be arranged and implemented so that the patient identification display retrieves the patient identification information from the wrist bracelet 40 and electronically displays it. The patient identification display 100 may be programmed to cease displaying the patient identification information if the patient bedside device 96 no longer senses the presence of the patient. Patient chairs may be similarly equipped with smart devices to sense the presence of a patient and to convey such information to a patient identification display 100. Further, in order to establish an association with a patient, the ICD 10 may be required to establish a communication link with the patient identification display 100 instead of or in addition to the wrist bracelet 40, which patient identification display 100 would in turn transmit the patient identification information to the ICD 10. This would permit the transfer of patient identification information without the possible necessity of disrupting the patient in order to establish a communication link with the patient's wrist bracelet 40.

Figure 12:
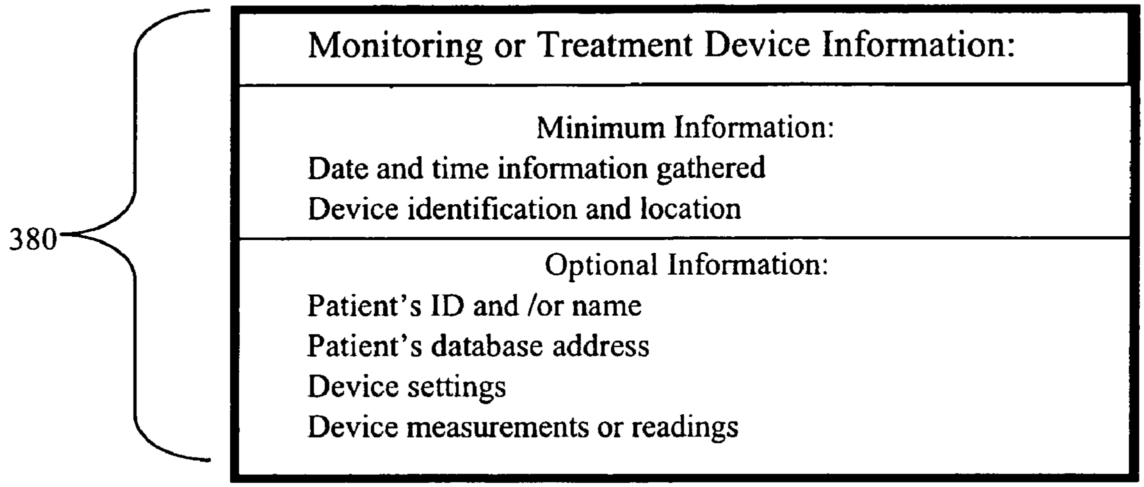
FIG. 12 is a list of information transferred from a patient monitoring or therapeutic device to a security badge.

If a new patient comes to occupy the patient room 104 or the patient bed 80, the patient identification display 100 obtains the new patient identification information from the wrist bracelet 40 worn by the patient and may be structured to transmit that information to the Admit, Discharge and Transfer System 166 (FIG. 7) of the computer network 194. Alternatively, the patient identification display 100 could display a request for input indicating whether or not the new patient is to be marked as having been transferred to the instant patient room 104. A patient monitoring device 80 (FIG. 4) or bedside treatment device 178 (FIG. 7) may reject a data exchange request from an ICD 10 if the physician wearing the ICD 10 is not authorized or cleared to diagnose or administer treatment to the patient. FIG. 12 illustrates the contents of the monitoring or treatment device information 380 that the bedside treatment device or patient monitoring device 80 may transmit to the ICD 10 if the data exchange is authorized. As part of a double-audit function, the monitoring device 80 or the bedside treatment device 178 would itself record any data transaction made with an ICD 10.

VII. Electronic Signature

Hereinafter, while information units and information packets as described above are still contemplated, other types of information such as word processor documents, spread sheets and the like are also contemplated and all such information types will be collectively referred to as documents.

An extremely important aspect of the present invention is that a physician's identity is added to collected information or documents prior to long term storage or transmission to a server for further processing. By adding a physician's identity, the system creates proverbial "ownership" of the document (i.e. information collected).

Taking this "ownership" one step further, according to another aspect of the invention, the information approval process which must be performed prior to long term document storage or transmission to a server requires a physician to take "responsibility" for approved documents. To this end, the present invention contemplates a digital signature procedure whereby, when a physician approves a document, the physician's identity and, also preferably, an indication of the content of the document approved, are added to the approved document. This type of approval system helps ensure that documents are accurate. This is because, if a physician knows approved documents are to be recorded and attributed to the approving physician, the physician will be more careful to ensure document accuracy.

In one embodiment a simple text phrase is provided in a document approval field. For example, upon approval the phrase, "Dr. Smith approved this document on Tuesday, Aug. 25, 1998 at 10:30 AM", may be added to the document.

The physician's identity may be determined in any of several different manners. For example, as a physician's ICD 10 must gain access to a terminal to review document information, the physician's ICD 10 may, during the interrogation process, provide an indicator of the physician's identification. In the alternative, each time an approval icon is selected the terminal may send a message to the physician's ICD 10 requiring a physician's digital signature. When the message is received the ICD 10 transmits the physician's digital signature in encrypted form. In this case, when a terminal receives the encrypted digital signature the terminal deciphers the encryption and correlates a physician with the digital signature.

In another embodiment, when a physician logs onto a terminal in a conventional manner (e.g. entering a password)

via a keyboard), the terminal may identify the physician and subsequently add the physician's identity to each document approved by the physician.

While a simple text phrase indicating approval suffices to convey that a specific individual approved a document at a specific time, such text phrases are relatively impersonal and therefore have relatively little value in terms of creating a "feeling" of responsibility for approved documents. Therefore, preferably, instead of providing an impersonal text phrase to indicate approval, a picture of a physician's actual scripted signature (i.e. a signature picture) may be digitized and stored in an ICD memory, the signature picture provided to the terminal for insertion in the approval field along with the time and date of approval. The signature has traditionally been an indicator of responsibility and therefore indicates the import of the approval process to the approving physicians.

Unfortunately, even where a digital signature picture is provided, it is possible for an unscrupulous physician or some other unscrupulous person who has access to a stored document to effectively electronically modify the approval field by, for example, copying a physician's digital signature picture from one approval field into another. While such copying may be accomplished electronically by cutting a signature picture from one digital document to another, such copying or forgery may also be accomplished after a digital document has been printed out in paper document form. For example, after a digital document is printed, a physician's signature may be clipped out of a first document, taped on a second document and copied via a high quality copier thereby rendering a document which was seemingly signed by the physician.

To ensure authentic signatures on documents, the present invention further includes an electronic "watermarking" procedure. A watermark is a mark which is difficult to reproduce and which is "laid over" some other information generally for the purpose of identification and indicating authenticity of the underlying information. For example, often a watermark will be provided on paper currency, the mark appearing like a water stain across a portion of the paper, hence the term "watermark". Watermarks have also been used to mark copyrighted material, the marks subsequently used to identify any copies of the copyrighted material.

Unlike currency watermarks, electronic watermarks and differences there between often are difficult to perceive via the human eye. Instead, electronic marks include pixels within a displayed picture which have specific and known characteristics. For example, one electronic mark on a screen display may include modified white pixels where every 10th white pixel which appears within the picture is slightly grey. While the specific color is slightly different than other white pixels, the difference is not detectible by the human eye. Instead, a computer is required to identify the pixilated watermark. In this case, if an electronically marked screen is electronically copied, suitable software running on a computer can be used to analyze the copy and detect the electronic watermark (e.g. the unique pixel intensities). In addition, where an electronically marked document is printed out, the watermark should be reproduced as a printed mark which can be used for subsequent authentication. Moreover, where a printed document including a mark is copied using a high quality copier the mark should be reproducible and thereafter useable to authenticate.

In addition to unique pixel shading, electronic marks can be provided by providing different pixel intensities, pixel intensity or shading designs, a uniquely configured pixel bar adjacent a graphic design and so on.

Like a digital picture, a physician's digital signature picture includes perhaps thousands of pixels. Unique signature picture pixel characteristics can be provided which can be used to identify authentic signature pictures. Unfortunately, as with a screen, a copied signature picture will often include the watermark pixels and therefore an authentic signature picture, as opposed to an electronically or manually (i.e. physical cut and tape) copied signature picture, may be difficult to identify.

To overcome the problem of accurately copied watermarked digital signature pictures, the present invention includes a content varying watermark which is generated as a function of the content of a document to which a signature is applied.

Generally, according to the present invention, in addition to storing a physician's signature picture, an ICD memory also stores a standard watermark (SM) which corresponds to the physician and a program for modifying the standard watermark SM as a function of document content (DC). When a document is to be electronically signed, the document is transmitted to the physician's ICD 10. The ICD 10 recognizes the requirement for signature, retrieves the standard mark, mark modifying program and signature picture, isolates document content, modifies the standard mark as a function of the document content, places the modified mark on the scripted signature picture or on the document itself, places the marked signature picture on the document in an approval field and retransmits the "signed" document to the terminal. The modified mark MM can be expressed as:

$$MM=SM+f(DC)$$

wherein f indicates a function. Other equations for identifying the modified mark MM may be used. For example, mark MM may be a function of both the standard mark SM and document content DC (i.e. MM=f(SM, DC)) or may be a function of both standard mark SM and a different function of document content DC (i.e. MM=f'(SM, f(DC))), etc. An example of how this aspect of the invention operates is instructive.

In this example, it will be assumed that a physician is currently logged onto a terminal, has download various documents to the terminal for review and now wishes to approve a document prior to long term storage.

Figure 25:
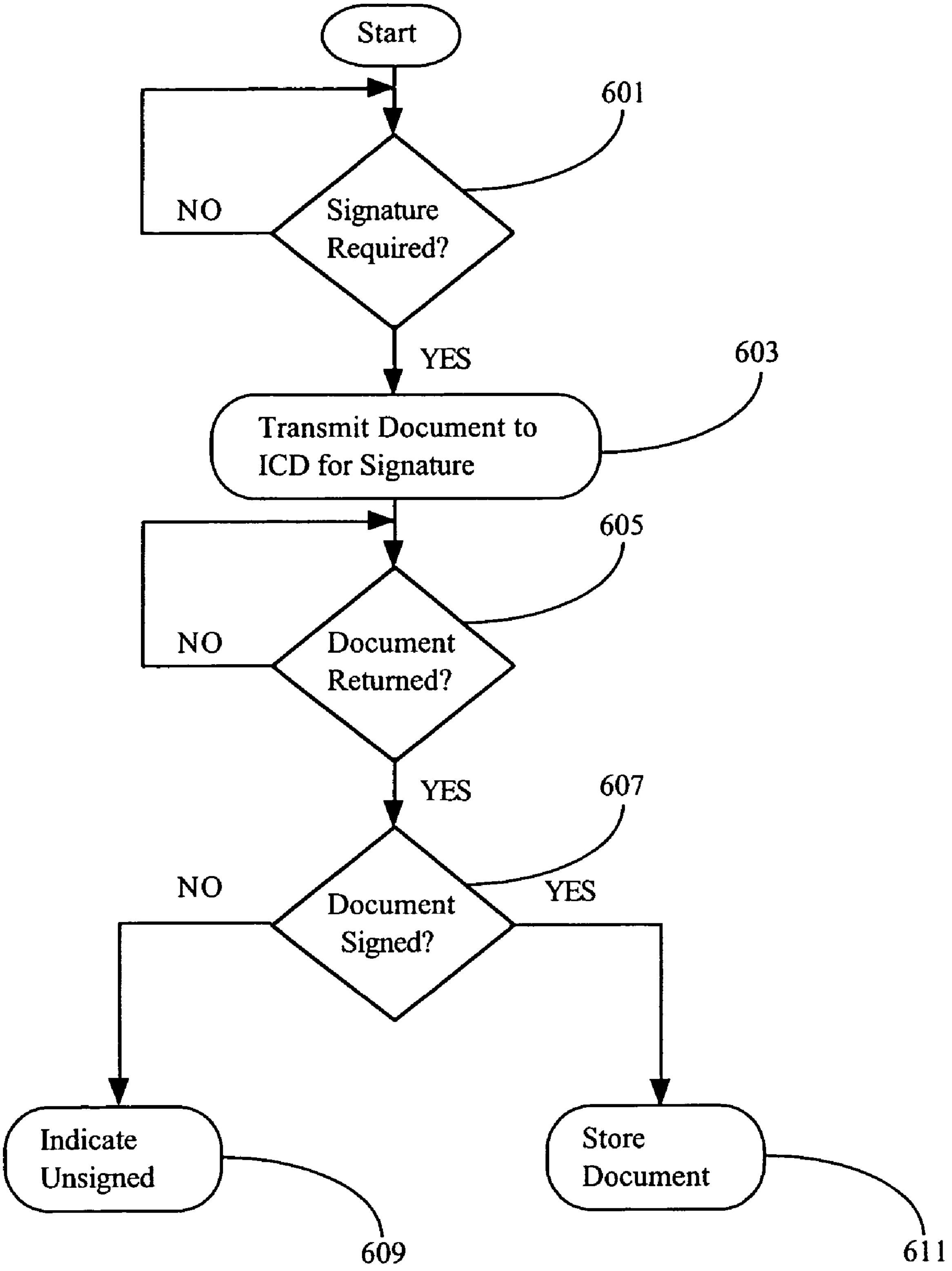
FIG. 25 is a flow chart illustrating a portion of a digital signing process according to the present invention.

Referring specifically to FIG. 25, when a physician selects an approve icon to approve a previously reviewed document, at block 601 the terminal determines if a watermarked signature is required for the document to indicate approval. Where a watermarked signature is required, at block 603 the terminal transmits the content of the document to be "signed" to the physician's ICD 10 along with a simple instruction indicating that a digital signature is required.

Figure 26:
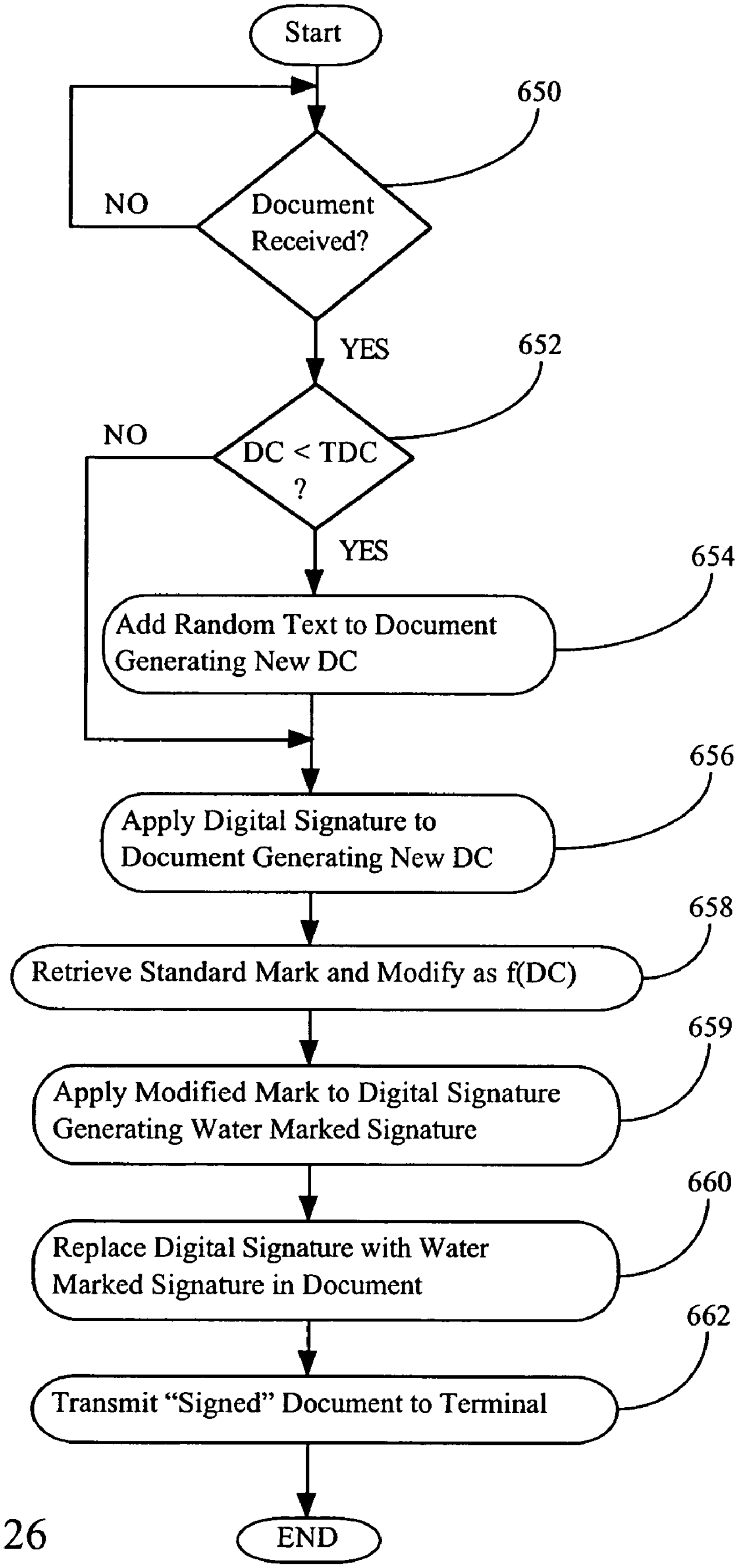
FIG. 26 is a flow chart illustrating a portion of a digital signing process according to the present invention.

Referring also to FIG. 26, when the ICD 10 receives the document and instruction at block 650, ICD 10 recognizes the instruction and ICD control passes to block 652. In some cases a document may include minimal information and therefore it might be difficult to generate a distinct and difficult to decipher watermark MM. Therefore, although not a requirement of the invention, it is contemplated that, in one preferred embodiment, there will be a minimum or threshold document content (TDC) requirement which indicates the minimum amount of content required to generate a mark MM. Where the document content DC is less than the requirement TDC, additional information, either random or meaningful, is added to content DC prior to modifying the standard mark. Meaningful data may include the current time or date.

The additional information is not necessary to understand the meaning of the document. Therefore, it is contemplated that the additional data would typically be added to the document in some non-visual manner. For example, the additional data may be added as some hidden text in a hidden note field or the like. On the other hand, the additional data may be added as a visual bar having varying pixel intensities. The important aspect of the additional data is that the additional data enables a secure content specific watermark to be generated which is not easily subjected to decryption.

Referring again to FIG. 26, at block 652, ICD 10 compares the document content DC with the threshold requirement TDC. The comparison may be as simple as comparing the number of words or characters in the DC to a corresponding threshold number TDC. Where the DC exceeds the TDC, control passes to block 656. Where DC is less than the threshold requirement TDC control passes to block 654.

At block 654 ICD 10 adds additional text or numbers to the DC thereby generating a new document content. As indicated above, the additional data is preferably, although not necessarily, added so that it will not appear on the document when the document is displayed.

At block 656 ICD 10 retrieves the ICD user's scripted digital signature picture and applies the signature picture to an appropriate and designated location (i.e. the approval field) on the document. At block 656 ICD 10 retrieves the standard graphic mark from the ICD memory and modifies the standard mark SM as a function of the document content DC (e.g. the original document plus any additional data added plus the digital signature picture) to generate a modified mark MM. At block 659 ICD 10 applied the modified mark MM to the scripted digital signature picture generating a watermarked signature picture.

At block 660 ICD 10 replaces the digital signature picture on the document with the watermarked signature picture and at block 662 ICD 10 transmits the "signed" document back to the terminal.

Referring again to FIG. 25, after having transmitted a document to an ICD at block 603 the terminal awaits return of a signed document at block 605. When a document is received by the terminal control passes to block 607. At block 607 the terminal determines if the received document was signed. At block 609, where the document has not been signed for some reason, the terminal indicates failure to sign. At block 611, where the document has been signed the terminal stores the signed document. In addition, to facilitate the "feeling" of ownership and responsibility for the signed document, the terminal may display the document with the physician's scripted digital signature picture thereon.

To allow a physician to confirm that approval occurred it is contemplated that, according to at least one embodiment of the invention, after a terminal displays a document including a signature picture, and prior to storing the document to long term storage or transmitting the document to a server for further processing, the terminal may provide a "STORE" icon which, when selected, stores or transmits the document including the signature picture. When the STORE icon is selected the document is transmitted.

When an approved document is accessed at a subsequent time, if there is any doubt that a signature picture is authentic, the physician's ICD 10 which was supposedly used to generate the signature picture can be used during an authentication process to re-generate the suspect document. Then, the suspect and regenerated documents can be compared to determine if the suspect document is authentic. Where the documents are dissimilar, an electronic forgery has been identified and the suspect document is identified as a forgery.

To confirm authentic approval, it is contemplated that, software which allows a physician to retrieve and review stored information units will provide some authentication functions while each physician's ICD will facilitate other required functions. For instance, in one exemplary embodiment the retrieval/review terminal software is capable of scanning in a watermarked scripted signature picture from a hardcopy of a document, scanning in an entire document including a watermarked signature picture, or selecting a signature picture from a document displayed on a screen. In addition, the software can magnify a digital signature and digitize the signature and watermark and can transmit the signature to an ICD along with a command requesting signature authentication. Moreover, the software also enables the terminal to receive a document from an ICD for display. The software may also enable split windows so that a suspect document and a regenerated document can be viewed side-by-side to facilitate visual authentication. Furthermore, the software may be able to perform document comparison to identify document discrepancies.

To authenticate, the ICD is able to receive a watermarked signature from a terminal, remove the standard graphic watermark from the watermarked signature, generate a regenerated document from the remaining marked signature and transmit the regenerated document to the terminal for examination. An example of how a signature is authenticated is instructive.

Figure 27:
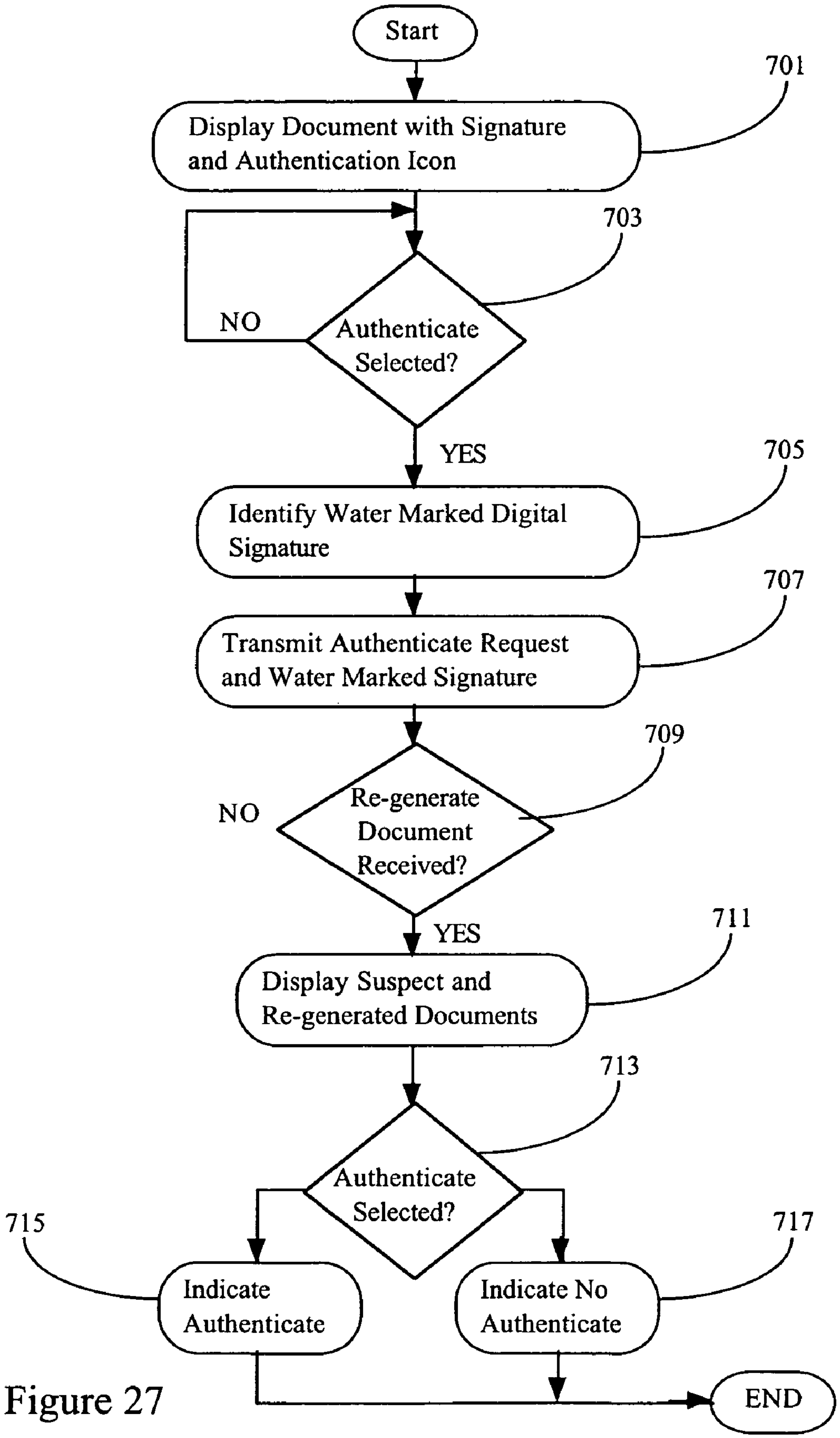
FIG. 27 is a portion of an authentication method according to the present invention.

After a physician gains access to a terminal via an ICD-terminal interrogation, the physician selects a review software application which allows the physician to select and examine one or more documents which were previously approved and stored on a server in the manner described above. After selecting the review application, the physician selects one document (e.g. patient record or check, etc.) to examine and, referring to FIG. 27, at block 701, the software displays the selected document, in HTML format as earlier stored. As part of the stored document, the software displays a digital and watermarked signature picture purportedly representing the signature of the physician who approved the document. The date and time of approval may or may not also be displayed. In addition, the software also provides an "AUTHENTICATE" icon adjacent the digital signature picture. It will be assumed that the reviewing physician is the physician who purportedly originally approved the document being examined and that the physician's scripted signature picture, standard watermark and mark modifying program, all stored on the physician's ICD, remain the same.

While the physician is reviewing the document, the physician notices something which the physician cannot remember approving. For example, while the document may indicate that eight capsules of drug A were administered to a patient the physician may clearly remember that only two capsules of another drug B were administered. While the physician recognizes that she may have made a mistake, the physician nonetheless would like to authenticate the document.

Referring again to FIG. 27, to authenticate the document, at block 703 the physician selects the AUTHENTICATE icon and the software recognizes the selection. At block 705 the software identifies the watermarked digital signature picture and isolates that portion of the displayed document. Next, at block 707 the terminal transmits an authenticate request to the ICD along with the watermarked signature picture. At decision block 709 the terminal waits to receive a re-generated document from the ICD 10.

Figure 28:
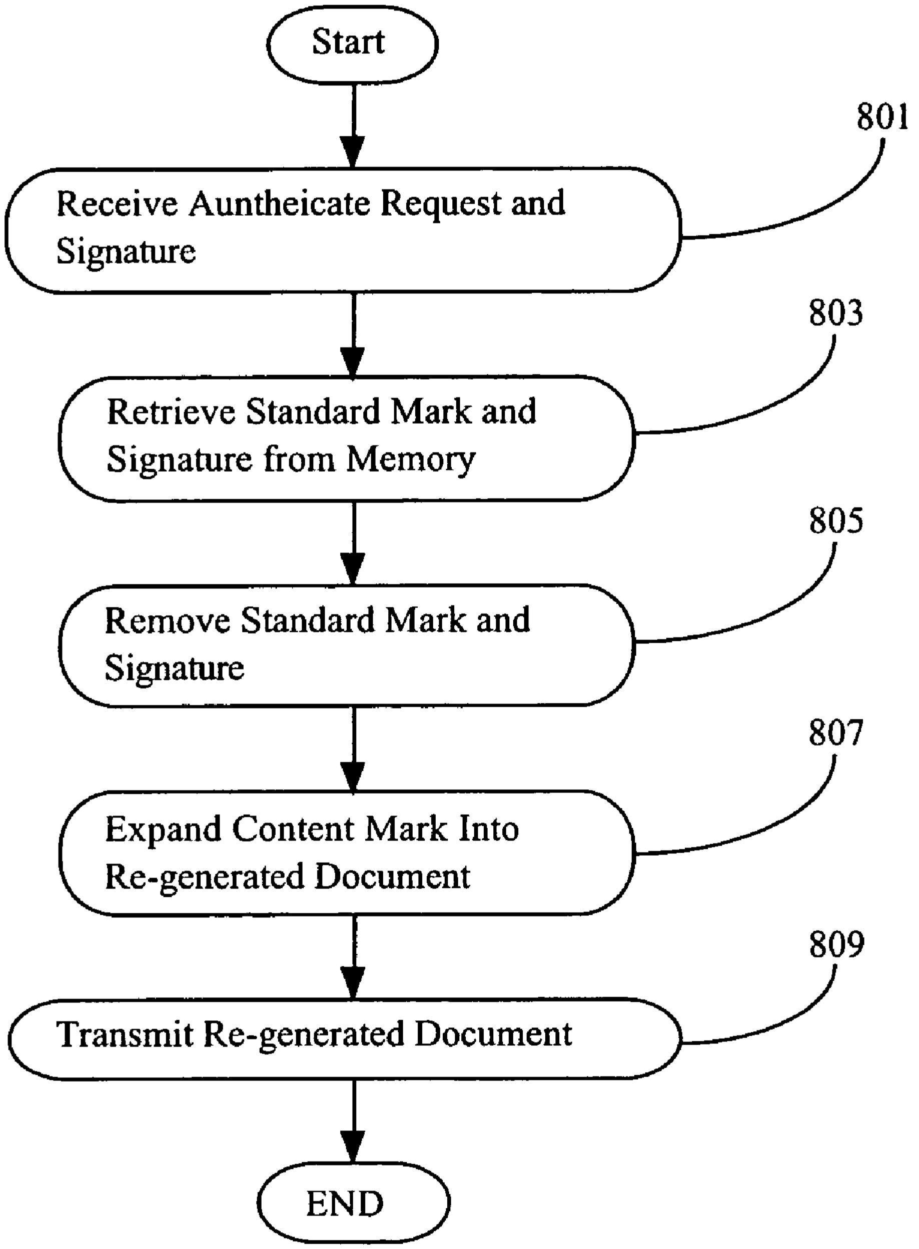
FIG. 28 is a second portion of an authentication method according to the present invention.

Referring also to FIG. 28, at block 801 the ICD receives the authenticate request and the watermarked signature picture. At block 803 the ICD retrieves the standard watermark and the physician's digital signature picture from its memory. At block 805 ICD 10 removes the standard watermark from the watermarked signature picture thereby generating a watermark which specifically corresponds to document content. At block 807 ICD 10 expands the remaining content watermark into a re-generated document. The re-generated document includes the document which was originally approved by the specific instance of the physician's digital signature picture and may include additional data if additional data was added to the approved document during standard watermark modification. At block 809 the ICD transmits the re-generated document to the terminal.

Referring again to FIG. 27, at block 709 when the regenerated document is received, control passes to block 711 where the terminal displays both the suspect and re-generated documents side-by-side for comparison. The physician should then be able to visually compare documents to determine if the documents are identical.

If desired, the terminal software can be equipped to itself compare documents to determine similarity. To this end, at block 713, the software compares the suspect and re-generated documents. In addition to comparing visual document information (e.g. text, graphics, data, etc.), the terminal software can also compare any additional data which was added to an original document to the additional data in the regenerated document. Thus, even hidden or visually meaningless (e.g. a bar having varying pixel intensities) random information can be used to authenticate an associated document.

Clearly, facilitating document comparison via software is advantageous for several reasons. First, as indicated above, random data comparison ensures a more thorough comparison. Second, presumably software comparison would be much faster than visual manual comparison. Third, for long documents such as a mortgage, contract, historical medical record, etc., software could compare every aspect and all document information to identify even a single document change.

Referring again to FIG. 27, where an original and a re-generated document are identical, the terminal indicates authentication at block 715. Where the documents are even slightly different the terminal indicates "no match" at block 717 signaling that the signature on the suspect document was not provided by the physician.

In another embodiment of the invention public key encryption (PKE) may be used with a digitally watermarked signed document to authenticate the document in the absence of a physician's ICD. A conventional PKE system is described in U.S. Pat. No. 5,689,567 (hereinafter "the '562 patent") which has been referenced above and which is incorporated herein by reference. Generally, in a PKE system each system user has both a "secret key" and a "public key" for encryption purposes. To effectively mark a document for authentication purposes a mark (i.e. bar graph or seal, etc) is generated by subjecting document content to the secret key. Thereafter the mark is applied to the document and can be stored or printed out on hard copy. To authenticate a marked document, if the document is a hard copy, the document is scanned into a computer to generate a digital document. After scanning or if the original document to be authenticated is a digital document, the mark is lifted from the digital document and used to regenerate a document corresponding to the mark using the public key of the person who supposedly approved the document via the mark. To this end, in a hospital facility, for example, all physician public keys may be stored on an Intranet and may be accessible for authentication purposes.

After the public key corresponding to the physician who supposedly approved the document is used to expand the mark into a re-generated document, the original and regenerated documents are compared to authenticate. This type of PKE system can clearly be used with the present invention to generate documents from watermarks for authentication purposes.

Also, in accordance with the '567 patent, a hashing method can be used to encrypt, decrypt and authenticate a document. To this end, according to the present invention, after a standard mark (e.g. a signature picture) is added to a document, document content or a representative portion thereof may first be hashed using a hashing code and generating an initial document hash. Thereafter, the initial hash may be encrypted using a private encryption key to generate a watermark which is applied to the document.

In this case, to authenticate, a watermark is identified on a document and is decrypted using a public encryption key to generate a re-generated hash. Next, a private key is used to again hash the document content generating a document hash. The document and re-generated hashes are thereafter compared to authenticate.

It should be appreciated that while the inventive time dependent electronic watermark described herein is extremely advantageous in the medical records area to authenticate an approval indication, clearly, this invention can be used in any application where a digital approval must be provided. For example, where bills are paid by electronic check, a users digital time dependent watermark can be provided on the electronic check, the mark generated in the manner described above. Similarly, a digital time dependent watermark could be provided when a credit card number is used to purchase something over the Internet. In either of these two applications, instead of generating the watermark using an ICD, a terminal itself could be used to generate the mark and apply the mark to a terminal stored digital signature.

Figure 29:
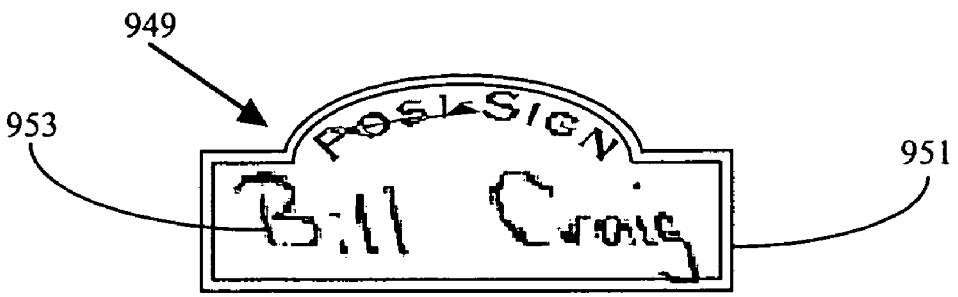
FIG. 29 is a view of an exemplary digital signature picture.

Referring to FIG. 29, an exemplary signature picture 949 is illustrated and includes a scripted signature picture 953 and pre-water marked border 951.

Figure 30:
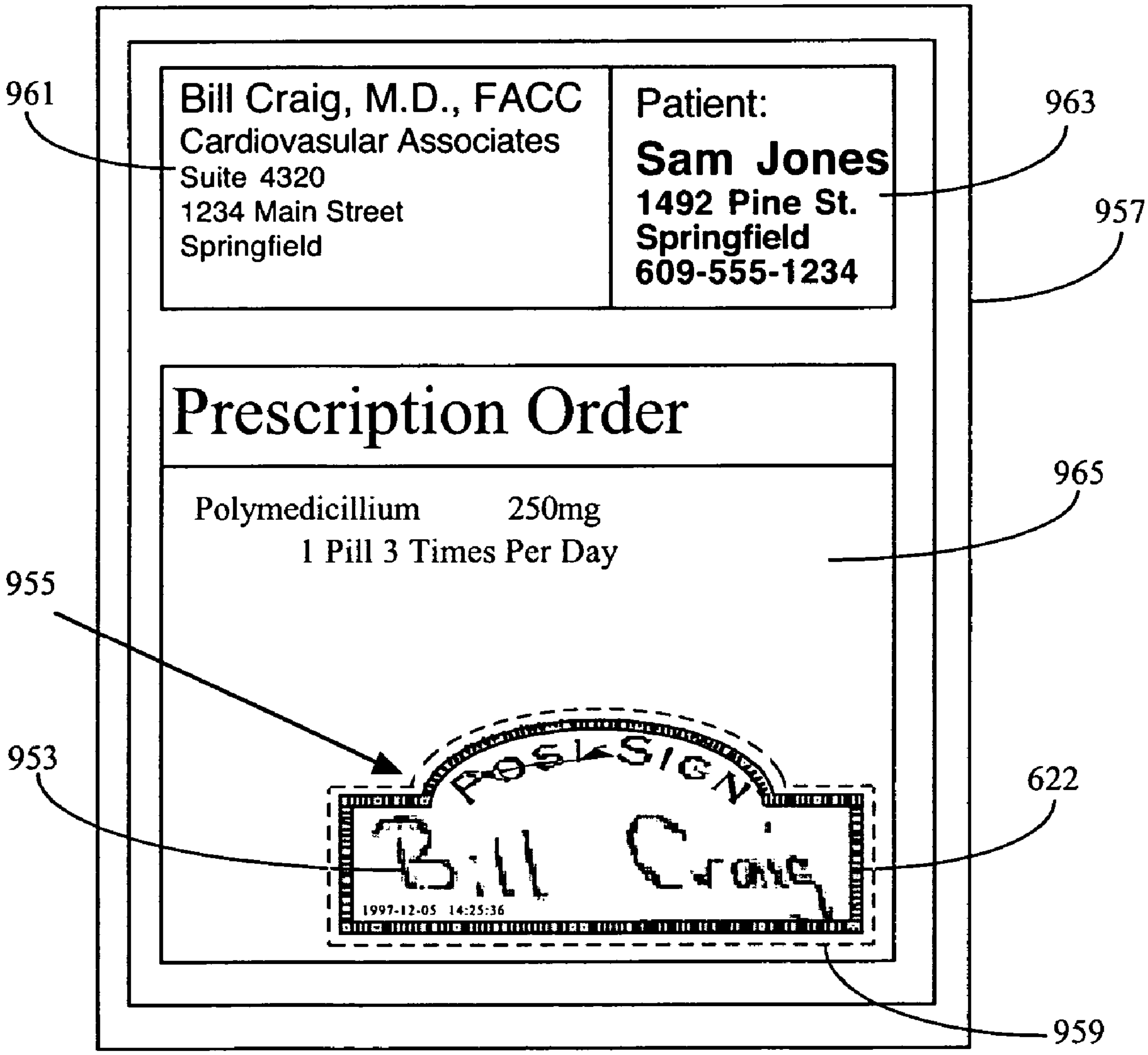
FIG. 30 is a schematic view of an exemplary digitally signed and watermarked document according to the present invention.

Referring also to FIG. 30, a watermarked signature picture 955 applied to an exemplary document 957 in a designated approval field (phantom identified by numeral 959) is illustrated. Picture 955 includes the signature picture 953 inside a watermarked boarder 622 digitally signed document 620 according to the present invention is illustrated. The exemplary document 957 is a digital prescription which includes information which one would expect to find on a prescription. The information includes a prescribing physicians name and address 961, a patient's name and address 963, and a prescription order 965 including medication prescribed, amount and required administration frequency. In this case, using a prescription software program, a physician fills in the information on the document 957 via a terminal. Assuming the information is accurate the physician then request a signature from the physician's ICD 10 at which point the content of document 620 is transmitted to the ICD 10.

Referring again to FIG. 26, when the physician's ICD 10 receives the document, assuming the document content DC is less than the threshold requirement TDC, ICD 10 adds random text/numbers to the DC. Thereafter, at block 656 the physician's digital signature picture is added to the document, at block 658 the modified mark is generated, at blocks 659 and 660 the modified mark is used to modify the digital signature picture and at block 662 the document 957, with the watermarked signature picture, is transmitted back to the terminal for review and if signed properly, for further transmission to other network storage or processing devices.

After digitally "signing" the document 957, the signed document is displayed and then transmitted to a server. Thereafter, when the prescription is filled, the signed document can be electronically returned to the physician stamped "filled".

Then, to authenticate the prescription the authenticate process described above can be performed.

In addition, it should be recognized that while a signature block is very personnel to a user and therefore is preferred in the present invention to convey a feeling of responsibility for the document to which the block is ascribed, any type of personal identifier which can be pictorially represented may be marked using a content dependent electronic watermark. For example, even a single horizontal line could be watermarked. Moreover, other types of information could be marked with time dependent watermarks for authentication purposes. For example, a video clip could be so watermarked, an audio clip could be so watermarked and so on. Furthermore, an electronic watermark can take any of several different forms such as, for instance, providing the background to a signature field or indeed providing the background for an entire document. In the case where the mark comprises the entire document background the entire background would have to be used during authentication to re-generate the document.

Moreover, while the watermarking procedure has been described as one wherein an entire document content is used to generate a mark, in the alternative a document digest may be used instead. For example, referring again to FIG. 29, a digest may simply include information filled in on a check such as issues, date, amount and signature where a digest is used to generate a watermark, comparison to authenticate compares only digest information, not an entire document.

While the approval/authentication concepts of the present invention were described above in the context of an ICD, the invention should not be so limited and is meant to cover other embodiments. The most general aspect of the approval/authentication concepts is that a document which has been approved by someone can be authenticated by using the document content. Other examples of how this general concept can be implemented are helpful to understanding the full import of this invention.

For example, according to another embodiment of the invention, a physician's terminal may be equipped with both a scanner and a printer and, where the terminal is personal to the physician, the terminal may share the physician's private secret encryption key, the physician's public encryption key accessible, via a LAN or the like, to other facility personnel.

In this case, if the physician has a hardcopy paper document which she would like to endorse, the physician may sign the paper document via a pen and a handwritten signature. Then the signed document is scanned into the computer via the scanner. Thereafter, it is envisioned that the computer retrieves the physician's private key, applies the private key to the document content (including the signature) to generate a watermark and then applies the watermark to a digital representation of the document. Thereafter, the digital representation may be printed out including the watermark or, in the alternative, the originally hand signed document may be provided to the printer input and run through the printer to add the watermark to the originally signed document. In effect, the printer would only print out the watermark which would be applied to the signed document.

Subsequently, to authenticate the document the watermark is identified on the document and scanned back into a terminal, the public key corresponding to the physician's signature which appears on the document is retrieved and is used to decrypt the watermark thereby generating a complete copy of the document which could either be examined on a computer display or printed out on hard copy for comparison to the original document.

According to yet another embodiment of the invention, a physician's terminal may be equipped with a digital signature pad for providing a digital signature. Digital signature pads are well-known and have been extensively used in the credit card industry to digitally record purchaser's signatures. A typical pad includes a flat sensing surface which senses the position of a pen tip as the tip is moved along the surface and generates a position signal indicating tip position. The position signal is provided to a computer which thereafter generates a "picture" of the pen tip movement. Where the pen is used to script a signature, the picture generated by the computer is the scripted signature. In this case, it will also be assumed that the physician's private key is stored on a private terminal and public key is generally available.

In this case, assuming a document is displayed on a computer display screen which a physician would like to approve, it is envisioned that the physician selects an approve icon on the display. Thereafter, the computer terminal requests the physician to hand script a signature on the digital pad. As the physician hand scripts the signature on the pad, the computer provides a digital representation of the signature in an approval field on the displayed document.

After the signature is completed, the computer retrieves the physician's private key, encrypts the signed document using the private key and thereby generates a watermark and applies the watermark to the displayed document, the mark remaining with the document when stored or printed out. Authentication in this example is the same as in the previous examples.

VIII. EXAMPLES

A few examples of how the present invention is intended to operate are instructive and aid in an understanding of why the invention is extremely advantageous. In each of the first four examples below, it will be assumed that both Penicillin and Tylenol are to be administered to a single patient within a facility within a specific time period and in specific doses by one of several authorized physicians. The patient is wearing an electronic identification bracelet like bracelet 40 of FIG. 2 which has, in its memory, at least some and perhaps all of the information which is illustrated in FIG. 9.

A. Example 1

In a first example, it will be assumed that a physician's ICD 10 is relatively complex so that the ICD 10 itself is capable of recognizing different types of received information, building a server target address for the received information and providing configuration information for displaying the received information via a browser screen on a display 103. Initially, referring also to FIG. 6, it will be assumed ICD 10 includes a physician identifying segment in memory 262 which identifies the physician associated with the ICD 10.

In this case, initially, it will be assumed that two Penicillin capsules and a single Tylenol capsule are dispensed into a container like container 200 illustrated in FIG. 5. In addition, referring to FIG. 10, a programming device such as dose dispenser 150 (see FIG. 7) provides a dispensation to processing device 75", device 75" storing received information in its memory. Moreover, dose dispenser 150 also generates a dispensation address for storing record 340. An exemplary dispensation record address 400 is illustrated in FIG. 13. Address 400 includes a field indicating the facility at which dispensation occurred (e.g. "St. Mary, Springfield"), a descriptor field (e.g. "medication"), an event field (e.g. "dispensed"), a patient ID field (e.g. "987654321"), a date field (e.g. "May 19, 1996") and a time field (e.g. "13:42"). All of the fields in address 400 are generated by dispenser 150.

As the physician makes her rounds, the physician eventually visits the patient for which the Penicillin and Tylenol were dispensed. After an abbreviated examination, the physician elects to administer half (i.e. 1 capsule) of the dispensed Penicillin and the entire dose of dispensed Tylenol (i.e. 1 capsule) to the patient. To administer the drugs the physician must first gain access to the Penicillin and Tylenol by unlocking container lid 204. In this example, it will be assumed that processing device 75" maintains lid 204 locked until a specific set of information is received by device 75" which matches information stored in the memory of device 75". Specifically, both patient identifying information which matches similar information in FIG. 10 and physician identifying information which matches similar information in FIG. 10 must be received by device 75".

Thus, to gain access to the contents of container 200, the physician places container 200 proximate the patient's bracelet 40 and causes the patient's bracelet to transmit patient identifying information (e.g. the patient identification number) to transceiver 81" on device 75". In this example this is accomplished by pressing an activation button (not illustrated) on device 75' in FIG. 2. A short time thereafter, the physician places container 200 proximate ICD 10 and causes ICD 10 to transmit physician identifying information to transceiver 81" by pressing button 18.

When device 75" receives the patient and physician identifying information, device 75" compares the received information with similar information stored in the memory of device 75". Where the received and stored information is not identical, device 75" maintains lid 204 locked and may indicate a mismatch by generating an audible sound via device 87". However, if the received and stored information is identical, device 75" allows lid 204 to be opened by pressing button 228. Device 87" may generate a different audible sound indicating the match. Audible alerting device 87" may also serve to remind a physician when it is time to administer the enclosed treatment.

In addition to facilitating opening of lid 204, when button 228 is pressed device 75" transmits all of the information illustrated in FIG. 10 as an information segment to ICD 10. This transmission can be in any form which is recognizable by ICD 10. When ICD 10 receives the information segment, ICD 10 does several things. First, referring also to FIG. 6, processor 250 identifies the time at which the information segment was received and hence the time at which lid 204 was opened via clock 254, processor 250 storing the identified time as a time stamp segment. Here, it is assumed that medicine administered to the patient is administered a short time after lid 204 is opened and therefore, administration time is indicated by the time stamp segment. Second, processor 250 recognizes the received information segment as a medication administration record and therefore automatically formats the received information and the time stamp segment as an information packet like the medication administration packet illustrated in FIGS. 14A and 14B.

In addition, ICD 10 uses received information to formulate a target address.

To this end, in FIGS. 14A and 14B, an exemplary target address is identified by numeral 444. Address 444 includes a facility field which indicates the same facility as the dispensing facility (i.e. St. Mary, Springfield, see also FIG. 13A), a descriptor field (i.e. medication), an event field (i.e. "given"), a patient ID field (i.e. "987654321") and date and time fields (i.e. "May 19, 1996" and "13:42", respectively).

After lid 204 is opened, the physician removes a single Penicillin capsule and the Tylenol capsule leaving the second Penicillin capsule in container 200 and administers the removed capsules to the patient. The physician recloses lid 200 which again locks and is routed back to the pharmacy for reinventory. If desired, the physician may make a manual note indicating that only one Penicillin was administered (e.g. via dictation).

After the physician completes her rounds, it will be assumed that the physician's ICD 10 includes ten information packets, each of which is similar to packet 440 in that each packet includes configuration information, a specific target address and some description information which describes a medical event (e.g. patient identifier, physician identifier, medication identifier, administration date/time, medication amount, etc.). In addition to the ten information packets, it is assumed ICD 10 forms an initial screen packet which summarizes ten information packets and provides interaction icons to facilitate physician review of the information packets. Referring to FIGS. 1 and 3, to transfer the initial screen packet and the information packets to system 194, the physician first gains access to a terminal 60 in one of the manners indicated above which is supported by the terminal 60. For example, the physician may position her badge proximate input device 64, at which time device 64 and terminal 60 generally interrogate ICD 10 to determine if the physician associated therewith is authorized to access the terminal 60.

After the physician gains access to terminal 60, the physician again positions ICD 10 proximate input device 64 and causes ICD 10 to transmit all ten information packets to terminal 60 via device 64. When the packets are received, browser 115 initially displays an initial screen which is configured in accordance with the instructions provided in the initial screen packet. To this end, the initial screen indicates the number of information packets received and also displays the interaction icons. The interactive icons are assumed to be REVIEW and STORE icons.

It is contemplated that a first physician might collect information packets via a first ICD 10 and a second physician might access a terminal 60 via a second ICD 10 to review, modify and approve descriptive information in information packets associated with the first ICD 10. Thus, after gaining terminal access via the second ICD 10, the information packets in the first ICD 10 are transmitted to the terminal 60 for review. In this regard, the terminal 60 may, after being accessed and receiving information packets, either allow the second physician to review, modify and approve the packets or may block the second physician from one or all of the review, modifying and/or approval abilities.

In most cases, it does not make sense for a physician who did not perform an examination to review, modify and approve information packets as the second physician likely would not know the specifics of an examination. For example, in the present case where a first physician elected to administer only one of two dispensed Penicillin capsules, the second physician would have no way of knowing that the first physician changed the prescription. Thus, if the second physician approved the information packet which indicates two Penicillin capsules were administered, the stored data would be erroneous.

To determine if a terminal accessing physician is the same physician who acquired information packets, the terminal 60, when accessed stored an accessing physician identifier. Then, when information packets are received from a second physician's ICD 10, terminal 60 identifies the administering physician associated with the packets (e.g. the physician associated with the second ICD) and stores an administering physician identifier. Next, terminal 60 compares the accessing and administering physician identifiers, where the accessing and administering physician identifiers are identical, terminal 60 allows information packet review as described hereinafter.

However, where the accessing and administering physician identifiers are not identical, terminal 60 may do one of several things first. First, terminal 60 may simply indicate that the accessing physician cannot review, modify or approve the information packets and thereafter may terminate access to the terminal 60.

Second, terminal 60 may allow the accessing physician to review the information packets but may not facilitate modification and approval functionality. Restricting the accessing physician in either of these first two way goes a long way to ensure that information transmitted to long term storage truly reflects an associated medical event.

Third, terminal 60 may add the accessing physician identifier to the descriptive information in the information packet and thereafter allow the accessing physician full review, edit and approve abilities. Then, when the descriptive information is stored, the accessing physician identifier is included therewith so that a complete audit trail for each information packet is formed. In addition, if desired, terminal 60 may also maintain an unmodified information packet for storage with each information packet which is modified by an accessing physician who is not an administering physician. In this manner, if modified descriptive information is erroneous, a record of unmodified descriptive information can still be accessed for review.

Continuing, assuming the physician elects to review the descriptive information in the information packets and is authorized to review, modify and approve packets, the physician selects the REVIEW icon. It will be assumed that the initial packet to review is the medication administration packet described above. When the physician selects the packet, browser 115 configures the browser screen as indicated by the configuration information stored in the packet and displays the descriptive information. In addition, browser 115 displays hyperlinks in instances when the configuration information so instructs and displays a hyperlink for the APPROVAL icon which indicates the target address. Thereafter, the physician can modify displayed information and then approve the information by selecting the APPROVAL icon.

In the present example, the physician consults her hand written notes and confirms that only half of the dispensed Penicillin was administered. Because the physician changed the amount of Penicillin administered to the patient from two capsules to one, the physician must modify the penicillin dose which is displayed. To do this the physician selects the dose amount which causes a pull down menu to open up providing the physician with other options (e.g. 1.5 capsules, 1 capsule, etc.) The physician selects one of the other options (i.e. in this case 1) and the menu closes as the dose amount is modified.

When the APPROVAL icon is selected, browser 115 transmits the approved information and associated hidden information to the server target address associated with the APPROVAL icon. After the first packet information has been approved, preferably the browser automatically presents the information in the next consecutive information packet via display 103. Again, the physician can quickly review the information, modify the information if necessary and approve the information for storage.

Thus, it should be appreciated that, using the inventive ICD 10 to collect information, configure browser screens and provide server target addresses for collected information streamlines the information gathering process and also streamlines the process of downloading information from such a device to a terminal for viewing, modification and approval.

In addition, by adding physician identification information to an information packet a record of medical administration information is formed. Moreover, by requiring an authorized physician to approve descriptive information which characterizes a medical event and identifying the approving physician in the descriptive information prior to long term storage, not only is the information review process easier and therefore more likely to be completed, the review process figuratively assumes "ownership" of approved data to the approving physician, thereby adding import to the approval process. In addition, by adding approving physician identification to the descriptive information or by adding a physician's watermarked digital signature to record, a complete audit trail for descriptive information is provided.

B. Example 2

In this second example, it will be assumed that a physician's ICD 10 is relatively simple in that the ICD 10 cannot itself formulate target server addresses or HTML configuration information and cannot generate most descriptive information (e.g. date and time stamp segments). Instead, in this example, address, configuration and most descriptive information is provided to ICD 10 by other system devices.

In this example, like the preceding example, it will be assumed that two Penicillin capsules and a single Tylenol capsule are dispensed into a container like container 200. However, in this case, in addition to providing the information illustrated in FIG. 10, dose dispenser 150 includes a specifier apparatus (see 64 in FIG. 3) which also provides a server target address and browser screen configuration information in HTML code to container device 75" (see FIG. 5). For example, referring again to FIGS. 14A and 14B, in this example, virtually all of the HTML code illustrated, including format field information, would be provided by dispenser 150 except for descriptive portions of some fields. Thus, for example, in field 444, the portion which reads "given" along with the patient identification number, date and time, would not be provided. Similarly, in field 452, verification "YES" would not be provided. Moreover, the administering physician in field 464 would not be provided.

To form the incomplete packet, dispenser 150 may be equipped with special software for generating appropriate HTML code or, in the alternative, dispenser 150 may be linked to a server for generating the HTML code. Referring to FIG. 7, in the present example, it is advantageous if dispenser 150 is linked to pharmacy server 186 for receiving pharmacy information related to ordered prescriptions. In addition, by being linked to the pharmacy server 186, when ICD 10 returns information to server 186 after dispensation and approval, dispenser 150 may access the returned information to confirm dispensation and if dispensation did not occur or a prescription was changed, dispenser 150 may indicate so via an alarm or some form of quality control reporting.

As in the previous example, when Penicillin and Tylenol are placed inside container 200, container 200 is positioned proximate a transceiver associated with dispenser 150 and dispensation information is transmitted to container device 75" via the dispenser specifier apparatus or output device 64 (see FIG. 3). In this case, however, transmitted information includes the entire packet 440, less the descriptive information (e.g. receiving patient i.d., date, time, administering physician, etc.).

Again, it is assumed that when the physician visits the patient for whom the Penicillin and Tylenol were dispensed, the physician elects to administer only one capsule each of Penicillin and Tylenol. Once again, to gain access to the capsules, the physician performs a specific procedure to open lid 204 whereby device 75" receives patient and physician identifying information, compares the information to similar information stored in the memory of device 75" and facilitates unlocking of lid 204 only when there is a precise information match.

In addition, if a precise information match occurs, referring again to FIGS. 14A and 14B, device 75" fills in various blank portions of packet 440 including verification field 452. It is assumed that when lid 204 is unlocked, drugs therein are administered to the patient associated with the patient identification number which was received by device 75". Therefore, device 75" fills in the patient identification number in field 444 further defining the target address. It is also assumed that the physician who opens lid 204 administers the drugs and therefore physician identifying information is filled in field 464.

After lid 204 is unlocked, when a physician presses button 228 to open lid 204, device 75" identifies the current date and time and provides that information both in the target address (in field 444) and in field 468 (i.e. the time stamp). At this point packet 440 is complete as illustrated in FIGS. 14A and 14B.

Assuming device 75" is proximate the physician's ICD 10, once packet 440 is complete, device 75" transmits entire complete packet 440, including HTML code specifying target addresses and screen configuration, to ICD 10. When ICD 10 successfully receives an information packet, ICD 10 may generate an audible signal or a visual signal (e.g. activate an LED to indicate successful reception. ICD 10 simply stores packet 440 until caused to transmit packet 440 to a terminal 60 for review, modification and approval.

The remainder of this example, is similar to the example above. Thus, after her rounds, the physician accesses a terminal and downloads information packets to a browser for review, modification and approval prior to storage.

This second example is advantageous because ICD 10 and other smart devices (e.g. container 200) need not be able to facilitate complex computations and formatting procedures. Instead, ICD 10 and smart devices, at most, must fill in a few descriptive fields and basically act as information storage buffers. In addition, this second example is advantageous because a dispenser 150 can specify a target address for returned information and how information which is returned to a terminal should be configured for review. This should facilitate a more flexible system. Moreover, the ICD 10 and other smart devices are relatively inexpensive as less remote computing power is required.

In addition, in this second example, as indicated above, dispenser 150 can close the information loop by tracking information returned to the pharmacy server 186 via ICD 10 and comparing that information to prescriptions which were to be administered. To this end, in addition to including the components illustrated in FIG. 3, the dispenser processor also includes a clock (not illustrated). In addition to indicating medication to be dispensed each prescription includes a prescribed administration period such as "between 2-3 PM" which is accessed by the dispenser 150 processor for each drug dispensed. When the drug is dispensed, the processor identifies the required administration period. For each prescription, at the end of the administration period or at the end of some predetermined reporting period (e.g. 2 hours) following the end of an administration period, the dispenser processor retrieves any data corresponding to a specific prescription which was returned by an ICD and also recognizes the absence of such data.

Where no data for a specific prescription has been provided by an ICD, the dispenser 150 may do any of several different things. First, the dispenser 150 may indicate via a dispenser display (see 103 in FIG. 3) that administration potentially was not performed. In addition, dispenser 150 may also periodically generate an audible "chirp" via indicator (i.e. alarm) 111. In the alternative, some other indicating mechanism such as an e-mail or pager signal may be generated to inform a physician or attending nurse of a potential mismedication. Still further, the dispenser processor may simply generate a record indicating possible mismedication. Subsequently, if ICD prescription data for the specific prescription is provided the indications may be automatically halted.

At the end of a prescribed administration or reporting period, if data for a specific prescription has been provided the dispenser 150 may retrieve the data and compare the data to the original prescription. In the present case where the administered medication was modified and therefore does not match the prescription exactly, it is contemplated that dispenser 150 generates a prescription/administration (P/A) quality control modification report indicating that the drugs administered were in fact different than those prescribed. In addition the P/A report may also indicate matching prescriptions and administrations.

The dispenser reports may be provided to an attending pharmacist for daily or weekly review or to a physician for review or indeed to an administrator or the like to track administration efficiency and accuracy.

C. Example 3

In this third example, it will be assumed that an ICD 10 is a hybrid of the ICDs in the above examples in that each ICD has less computing ability than the ICDs in the first example and more computing ability than the ICDs in the second example. In this example, it will be assumed that some of the HTML code for configuring a browser and providing browser addresses is provided to ICD 10 and that ICD 10 generates the remainder of required information and at least some of the descriptive information.

Figure 13A:
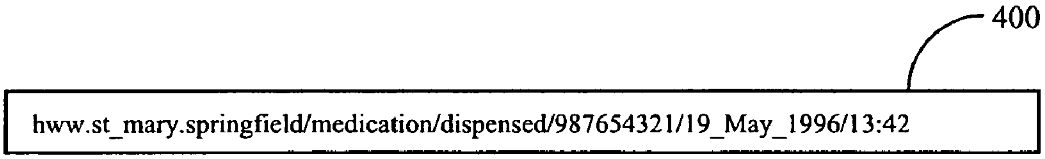
FIG. 13A is a textual representation of a URL address of medical dispensation record formed in part from the patient's identification number and a time stamp.
Figure 13B:
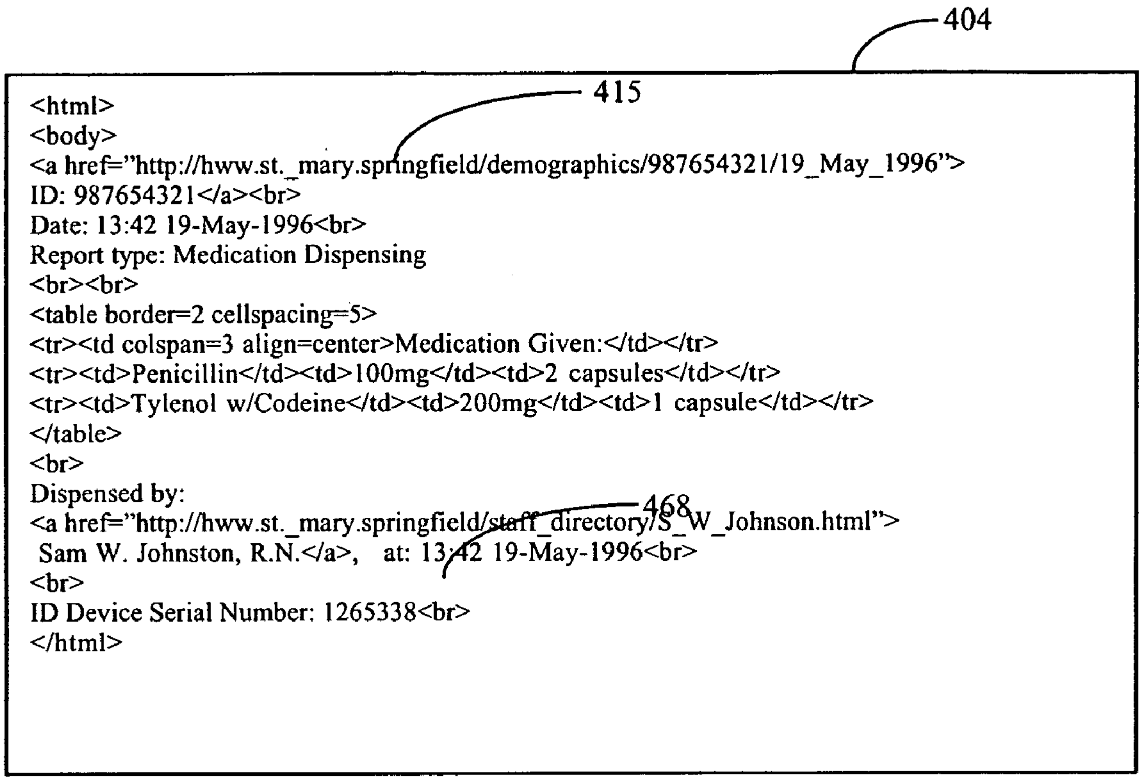
FIG. 13B is a graphical representation of a medical dispensation record with HTML codes for displaying the information in a network browser.
Figure 13C:
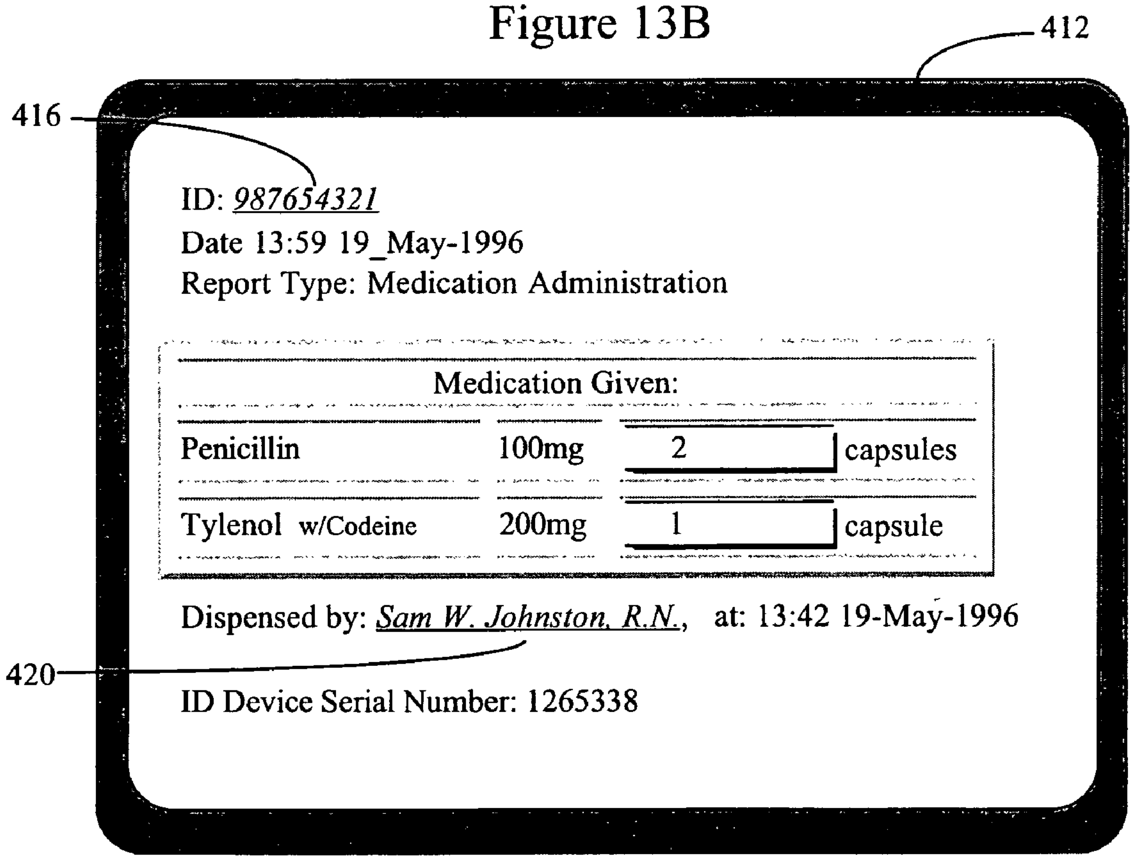
FIG. 13C is a graphical representation of the record of FIG. 13B as it would be viewed by a system user through a network browser.

In this example, like the preceding examples, it is assumed that two Penicillin capsules and a single Tylenol capsule are dispensed into a container like container 200. In this example, dispenser 150 provides an HTML dispensation information packet in HTML to device 75" which includes information for configuring browser 115 screens to indicate dispensation information. To this end, referring to FIG. 13B, an exemplary dispensation information packet 404 is illustrated. Referring also to FIG. 13C, a browser screen 412 which corresponds to packet 404 is illustrated including hypertext links 416 and 420, respectively, to a patient's demographic record and the bibliographic record of the physician who dispensed the medication. Packet 404 is formatted according to HTML and uniform resource locator—(URL) conventions. FIG. 13C illustrates the medication dispensation record 404 as it is displayed by a browser 412, FIG. 13A illustrates the URL 400 generated for the medication dispensation record 404 which identifies the location at which it is or will be stored.

In this example, prior to dispensing a dose to a container 200, a physician reviews dispensation information via screen 412. If dispensation information is correct, the physician approves the information and packet 404 is transmitted to container 200.

Again, it is assumed that when the physician visits the patient for whom the Penicillin and Tylenol were dispensed, the physician elects to administer only one capsule each of Penicillin and Tylenol. Once again, to gain access to the capsules, the physician performs a specific procedure to open lid 204 whereby device 75" receives patient and physician identifying information, compares the information to similar information stored in the memory of device 75" and facilitates unlocking of lid 204 only when there is a precise information match.

As in the first example, when button 18 on ICD 10 is pressed, ICD 10 identifies the time and date and stores that information as an time stamp segment for placement in a subsequently formed information packet.

After lid 204 is unlocked, when a physician presses button 228 to open lid 204, assuming device 75" is proximate the physician's ICD 10, device 75" transmits packet 404 (i.e. the HTML dispensation information packet in FIG. 13B) to ICD 10. When ICD 10 receives packet 404, ICD 10 modifies packet 404 by adding descriptive information, additional browser screen formatting information, formulating a specific target address and providing configuration information for interaction icons as indicated above, thereby generating a completed information packet like exemplary packet 440 in FIGS. 14A and 14B.

The remainder of this example, is similar to the examples above. Thus, after her rounds, the physician accesses a terminal and downloads information packets to a browser for review, modification and approval prior to storage.

D. Example 4

In this fourth example, it will be assumed that all smart devices and the ICD 10 are extremely simple in that none of the devices is capable of formulating or storing complex and complete screen configuration information. Instead, it is assumed that target address and minimal configuration information is provided to the smart devices and ICD 10 by other system devices and that the smart devices and ICD 10 simply provide descriptive information during a patient visit. In this example, to facilitate information review, a simple software package is provided on each terminal 60 which receives the minimal configuration information, correlates the minimal configuration information with a more detailed configuration format, and provides the detailed format for browser configuration control.

In this example, as in the second example above, dose dispenser 150 provides a server target address and browser server configuration information to a smart container device 75" when Penicillin and Tylenol are dispensed into a container 200. However, unlike in the second example where screen configuration information is provided in HTML code, in this example a simple configuration indicator code is provided which can later be expanded into more detailed HTML code for configuration. For example, the simple configuration indicator may be as simple as a single character or number. In this case, assuming there are only ten possible screen configurations for viewing descriptive information packet information, each of the ten possible configurations is associated with a different number indicator 0 through 9. In the present example, it will be assumed that a screen configuration for reviewing descriptive information in a medication administration information packet is identified by number indicator 4. In this case, in addition to receiving a target address upon medicine dispensation, container device 75" also receives indicator 4 which is stored for later transmission to ICD 10.

When lid 204 is unlocked so that the physician can administer the medicine therein, device 75" identifies descriptive information and provides the descriptive information, target address and screen configuration number indicator (i.e. "4") to ICD 10. ICD 10 stores the received information as a packet until caused to transmit the packet to a terminal 60.

In addition to storing the described information packets, it is also assumed ICD 10 also generates a dynamic initial screen indicator to provide dynamic information to browser 115 for display via the initial screen. To this end, it has been recognized that generally the initial screen will often include essentially the same information. For example, a typical initial screen will often only include an indicator to identify the number of files to be reviewed and perhaps a small number of indicators indicating the types of files to be reviewed (e.g. billing, dispersion, monitored information, dictation, etc.). Assuming a simple initial screen which only displays the number of files to review and icons to select review or store options, the dynamic initial screen indicator is simply a number. Assuming 10 files are stored in an ICD after a physician makes her rounds, the screen indicator is 10.

After the physician completes her rounds, the physician gains access to a terminal 60 in the manner described above. After the physician gains access and activates ICD 10 to transmit stored data to a terminal 60, ICD 10 transmits the initial screen indicator (e.g. 10) and the information packets.

When the transmitted information is received, terminal processor 107 performs several functions. First, processor 107 dissects each information packet thereby identifying, with respect to each packet, a target address, descriptive information and the screen configuration number indicator. Processor 107 uses the number indicator to identify a screen configuration for displaying associated descriptive information and forms an HTML packet like 440 (see FIGS. 14A and 14B) for each received packet, filling in descriptive information where appropriate. Each HTML packet is then stored in RAM 109.

Second, processor 107 identifies the initial screen indicator and fills in an appropriate field in an initial screen configuration. Then the initial screen is configured to enable a physician to review the descriptive information packet information. In the present example, because the initial screen indicator is 10 (e.g. there are 10 files to be reviewed), the initial screen indicates "There are 10 files to review" and provides REVIEW and STORE icons.

The remainder of this example is similar to the examples above. Thus, the physician can review, modify and approve information in each file stored in RAM 109.

This embodiment is advantageous in that most of the formatting capability can be provided in a terminal 60 as opposed to an ICD 10 as other smart devices. This is advantageous as it is contemplated that, in a typical facility, there will be many more ICDs and smart devices than there will be terminals 60. Nevertheless, consistent with the present invention, this embodiment still has the advantage of specifying target addresses via an ICD 10, instead of a server and specifying browser screen configuration albeit in an abbreviated format.

E. Example 5

In this fifth example, instead of interacting with a smart container 200, referring to FIGS. 1 and 4, it will be assumed that a smart IV treatment device 116' which, in addition to including an IV pump and proper patient linkage hardware, includes the hardware illustrated in FIG. 19, is provided in a patient's room 104. In addition, it will be assumed that the patient has been linked to the IV pump for several days and that a physician visits the patient's room to monitor patient condition and generate a report every 4 hours. Thus, a new patient record is generated every four hours.

In this example, as in the second example above, it will be assumed that ICD 10 is relatively simple in that most data is collected from IV device 116', and not generated. To this end, in addition to providing a dispensation information segment record indicating medicine dispersion since the most recent data acquisition (e.g. four hours earlier), device 116' also generates a target address for the dispensation record and browser screen configuration information indicating how a browser screen should be configured for data review. The dispensation information segment and address are assembled into an HTML information packet which includes several incomplete descriptive fields including a patient ID field, a time and date field and a physician ID field.

When a physician visits the patient linked to device 116', the physician establishes a patient association with ICD 10 as indicated above, the patient association stored as a packet identification segment. After the patient association has been established, the physician causes device 116' to transmit the incomplete packet to ICD 10.

When the incomplete information packet is received, if the time is not already identified in the received information, ICD 10 identifies the time and date of reception. ICD 10 places the time and date of reception, patient identifying information indicating the patient who received the IV medication (i.e. patient identified in the patient identification segment) and physician identifying information indicating the physician with whom ICD 10 is associated, in appropriate information packet fields thereby completing an HTML packet similar to packet 440 illustrated in FIGS. 14A and 14B.

A typical IV packet might include a period indicator which indicates the monitored time period (e.g. previous four hours) which corresponds to the dynamic data in the packet and a delivery rate field which indicates the rate of medicine delivered by IV device 116'. Where the delivery rate changed over the most recently monitored time period, the delivery rate field may include several medicine rate indicators which are each correlated with a delivery period over which the specific rate was provided. In the alternative, the rates may be provided in other forms such as a graph of rate versus time. In addition, the IV packet will also include a medication field indicating the medication dispensed via the IV, the physician who authorized the medication, the patient name and so on. Further more, the IV packet will also include a physician identifying field indicating the physician who acquired the IV packet.

As in the previous examples, when a physician completes her rounds, the physician gains access to a terminal 60 and transfers information packets, including the IV packet, to the terminal browser 115. Once again, the receiving browser identifies initial screen configuration information indicating the number of files transmitted to terminal 60 and displays the initial screen, including REVIEW and STORE icons.

Assuming the physician selects the REVIEW icon, terminal 60 displays the first information packet in the associated configuration format. As above, the IV information is displayed for review, in a format which is specially configured to display IV information. Although editing tools for modifying displayed IV information may be provided, such tools probably would not be provided as the IV information simply reports actual medicine administration and could not have been modified by a physician arriving for a visit after administration occurred. An APPROVAL icon allows the physician to approve the IV information for storage at the target address.

While this smart IV example is relatively simple, this example illustrates that the invention may be used with any type of smart device to remotely collect data and generate an ultimate target address and screen configuration data. The important aspect of a smart device is that the device can monitor some quantifiable information which is associated with a patient and which is advantageous to collect and store for later retrieval.

F. Example 6

Referring again to FIG. 1, in this sixth example of how the present invention might operate it will be assumed that a physician's ICD 10 is equipped to receive audio information (e.g. voice) via digitizer 22 when dictation button 26 is pressed. Thus, during a patient visit, a physician may use ICD 10 to take audio notes.

To this end, at the beginning of a patient visit, a physician's ICD 10 identifies the patient by communicating with the patient's bracelet 40 (see FIG. 2) and, after forming a patient association, stores patient identifying information as a patient identification segment. In addition, ICD 10 also stores a physician identification segment indicating the physician associated with the ICD. When the physician wants to form an audio note, the physician presses button 26 and thereafter speaks in the vicinity of digitizer 22.

When button 26 is pressed, ICD 10 recognizes that audio information is to be received and performs several different functions. First, ICD 10 automatically generates a target address for audio information to be received. The target address specifies a server used by a facility transcription pool. The transcription pool server is where all digital dictation is stored which is then transcribed either manually by facility personnel or automatically by transcription software. For the purpose of the present invention it will be assumed that transcription is manual.

In addition to generating the target address, ICD 10 identifies the time and date which are stored together as a time stamp segment. Moreover, ICD 10 automatically generates an incomplete audio information packet including browser screen configuration information and time, patient identifying and physician identifying fields and fills in the time and identifying fields with information from the time stamp, patient identifying and physician identifying segments. The only field which is not completed in this example is an audio dictation field which is to receive the digital audio information upon reception. In addition to generating the packet described above, the ICD 10 may also generate browser formatting information to formulate specific types of templates to be filled in by a member of the transcription pool. For example, the templates could include a template for a typical patient visit, a template for a prescription to be filled and so on. After the audio information packet is formed, ICD 10 stands ready to receive audio information via digitizer 22.

With button 26 pressed, when the physician speaks within the vicinity of digitizer 22, digitizer 22 receives the dictation, digitizes the dictation and stores the digitized information in the audio dictation field. At the end of the dictation, the physician stops pressing button 26. In the example, if, prior to ICD 10 forming a new patient association, the physician again presses button 26 to dictate again, the subsequent dictation is stored in sequence at the end of the audio dictation field. Once a new patient association is formed, when button 26 is pressed, a new audio information packet is generated.

In the case of an audio information packet, among other things, the configuration information will configure a browser screen which identifies time and date of dictation, dictating physician and patient visited. In addition, the configuration information may also provide interaction icons to allow a reviewing physician to play back and perhaps edit dictation. For example, interaction icons may include "PLAY", "STOP", "REWIND", "ERASE", "FAST FORWARD" and so on.

After a physician completes her rounds, as in the previous examples the physician gains access to a terminal 60 and transmits an initial screen configuration packet and other information packets, including the audio information packet described above, to the terminal 60. Browser 115 receives all the packets, stores the information packets and configures the initial browser screen as instructed by the initial screen configuration packet.

As the physician reviews the information packets, eventually the physician selects the above audio information packet for review. When the audio information packet is selected, browser 115 displays the descriptive information in the audio information packet including the interaction icons. The physician can review the audio information packet via the icons and, if necessary, may correct the dictation via some suitable means (not illustrated).

Figure 20:
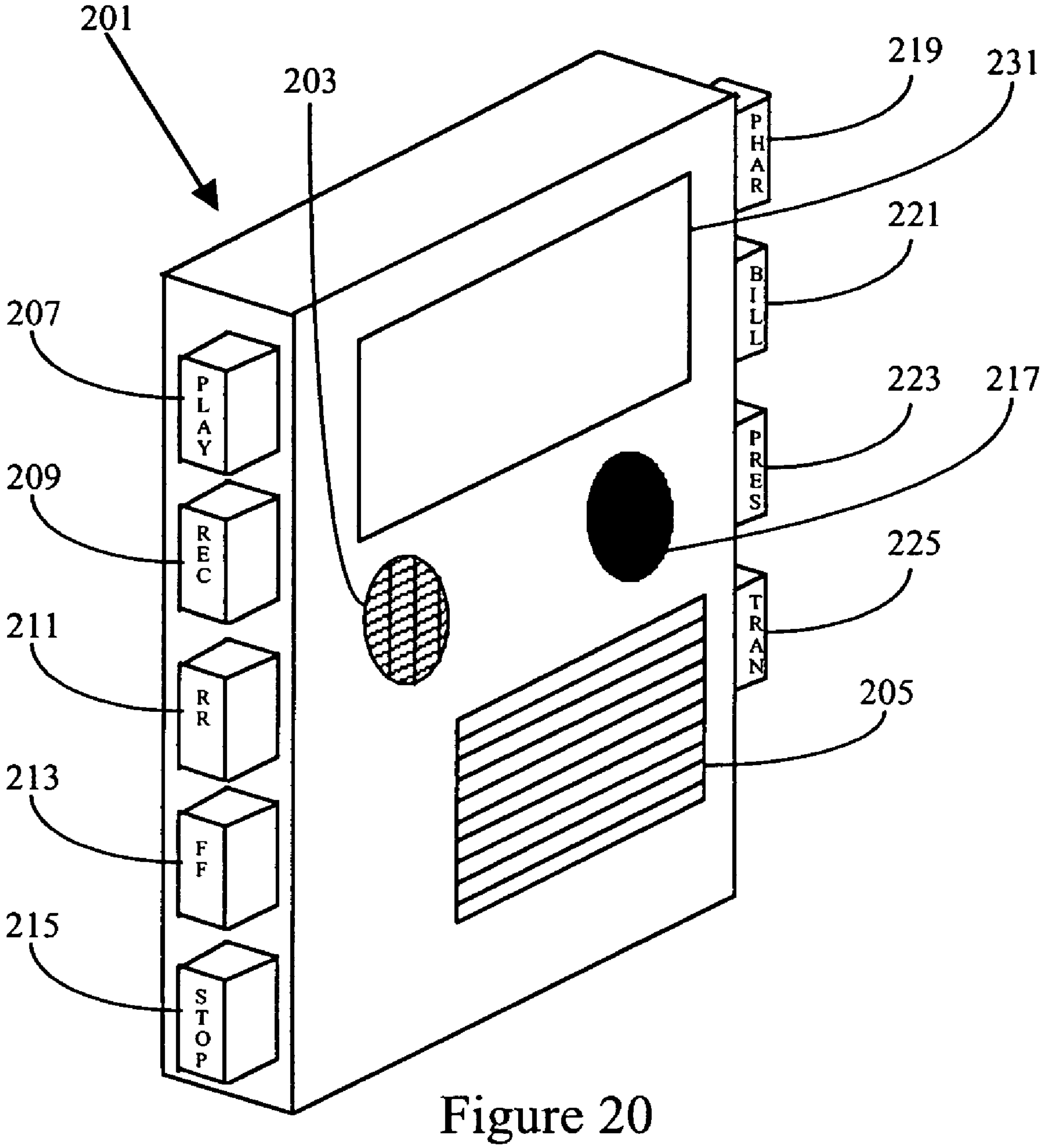
FIG. 20 is a perspective view of another embodiment of an ICD according to the present invention.

A second dictation facilitating ICD 201 is illustrated in FIG. 20. ICD 201 is similar to a conventional digital dictaphone in that ICD 201 is a hand held device including an audio digitizer 203, a speaker 205 and conventional editing buttons, "Play" 207, "Record" 209, "Reverse" 211, "Fast Forward" 213 and "Stop" 215. In addition, however, ICD 201 includes a transceiver 217, target address specifying or indicating buttons "Pharmacy" 219, "Billing" 221, "Personal" 223 and "Transcription" 225, a processor 250 (see FIG. 6) which is capable of configuring target addresses and screen configuration information and is capable of generating some descriptive information (e.g. physician identifying information, time and date, etc.). An optional screen 231 for viewing either collected data or a target address may also be provided.

With an ICD like ICD 201, it is envisioned that, by selecting one of the specifying buttons 219, 221223 or 225, a physician can generally select the target address for subsequent dictation. In addition, as with a conventional dictation device, by providing editing buttons on ICD 201, a physician can correct dictation immediately if desired.

When a physician stops to visit a patient during her rounds and would like to dictate a note which should be provided to a specific facility department, the physician first selects an appropriate department for receiving the note. For example, if the note is for the pharmacy to prescribe a specific medicine for a patient at a specific time, the physician presses button 219. When button 219 is pressed, ICD 201 generates an incomplete audio information packet which specifies, in appropriate fields, a visited patient, a visiting physician, time and date and a target address which specifies the pharmacy server. Once again, the only field which is not filled is the audio information field. Thereafter, the physician uses editing buttons 207, 204, 211 and 215 to dictate an intended note which is digitally recorded in the audio information field.

After her rounds, the physician accesses a terminal, transmits information packets and edits and approves the packets. With respect to the audio information packet targeting the pharmacy server address, when the audio information is approved, instead of going to the transcription pool, the information is transmitted to the pharmacy server.

In the alternative, ICD 10 may be configured such that more than a single server address can be selected by consecutively pressing more than one button 219, 221, 223 or 225 or, so that all dictation, in addition to being provided to the selected server, is also provided to the transcription pool server (or some other server for that matter).

G. Example 7

Figure 21:
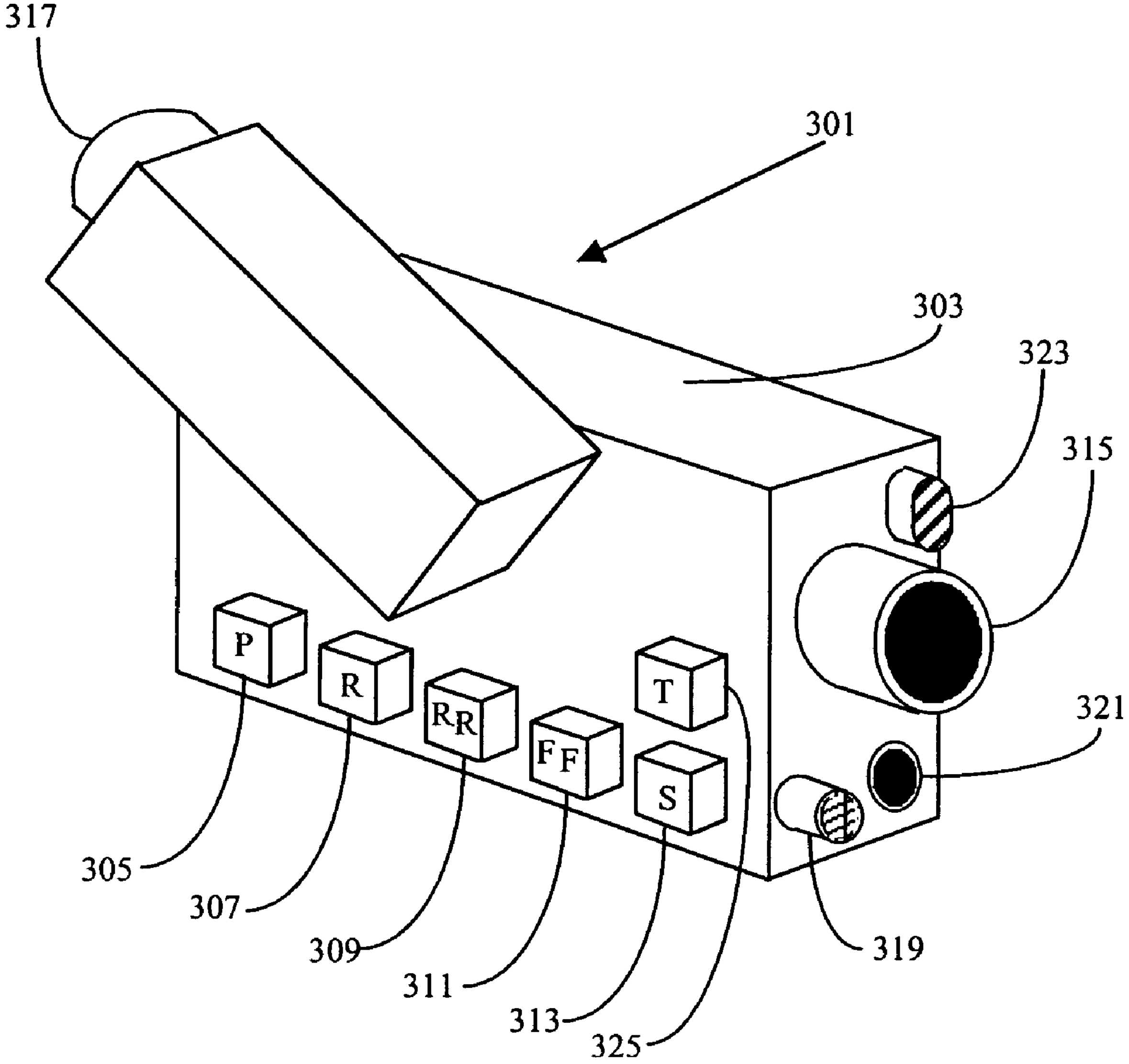
FIG. 21 is a perspective view of a video capable ICD according to the present invention.

In this seventh embodiment of the present invention, in addition to collecting audio information and other information which is provided by other smart devices (e.g. patient ID number, dispensed drug type and amount, etc.) an ICD is equipped to collect video information. To this end, referring to FIG. 21, an exemplary video equipped ICD 301 includes a main body housing 303 in which a processor and other already described hardware (see FIG. 6) is housed. Most importantly, the other hardware includes a clock and a memory (both audio, video and other information) in which user identification information is stored. In addition, ICD 301 includes conventional video editing buttons "Play" 305, "Record" 307, "Reverse" 309, "Fast Forward" 311 and "Stop" 313 which are linked to the ICD processor to facilitate recording, reviewing and erasing of video and audio information.

Moreover, ICD 301 also includes a video lens 315, a video viewer 317 which is pivotally attached to housing 303 and an audio digitizer (e.g. digital microphone) 319 for detecting audio signals. As with all ICDs described herein, ICD 301 also includes a transceiver 321 which can both receive information from smart devices and transmit information to smart devices and to a terminal. In addition, other data collecting devices may be provided such as a bar code reader 323.

Furthermore, ICD 301 also includes a toggle button 325. It is envisioned that, as with the audio ICD illustrated in and described with reference to FIG. 20, ICD 301 may be used to select a specific facility department to which collected data (e.g. video and audio) should be provided. In this example, the capabilities of viewer 317 are used in conjunction with toggle button 325 to select specific target facility departments. To this end, it is envisioned that where no other server is selected, a facility video archive department and associated server are selected as a default target for the purposes of generating a target address for collected information. Thus, if a user does not select a different target server, ICD 301 generates a target address specifying the archive server.

To select a different target server, a user looks into viewer 317. At the bottom of a displayed screen, a server indicator is displayed, the currently selected target server specified thereat. Thus, initially the server indicator indicates "Archive Server". To select a different target server, the user depresses button 325 once which causes the target server to change and causes the server indicator to also change accordingly. For example, pressing button 325 once may change the server indicator from "Archive Server" to "Pharmacy Server". By pressing button 325 a second time the server indicator observable through viewer 317 again changes to indicate another possible target server (e.g. "Billing Server"). Where there are five possible servers, any of the five servers can be selected by releasing button 325 once the desired server is indicated by the server indicator. To return to the initial default "Archive Server", the user simply scrolls through the server choices and, after the last choice has been displayed, the next time button 325 is pressed, the default server is again selected.

In addition, it is envisioned that, in addition to enabling selection of a specific target server, one choice provided by toggle switch 325 should be "No server" so that while information can be collected, no server has to be selected during data collection. Then, if the user desires, the user may, while reviewing a video clip via viewer 317, select any portion of the clip for delivery to a specific server.

Two examples of how ICD 301 might operate are provided hereinafter. In a first example, in a medical facility, when a physician makes her rounds and visits a patient, ICD 301 can be used as described above with respect to the preceding examples to establish an association with a specific patient through any of several different interrogation protocols. After association has been established, ICD 301 begins to build a conventional target server address using the physician's ID information, patient ID information, time and date (from the ICD clock, not illustrated). In addition, if IV information or drug dispensing information is collected, that information is automatically formatted for subsequent delivery to a terminal for viewing and further delivery to an appropriate server address indicated by the target address.

Assuming some peculiar visible symptoms are observed, the physician can use ICD 301 to record video of the symptoms for archiving and subsequent diagnosis. For example, if a physician observes a rash about a patient's elbow which the physician does not recognize as a symptom of the patient's known condition, the physician can collect a video clip to illustrate the rash. While collecting the clip, the physician can dictate an audio note explaining the rash.

Prior to collecting the clip, the physician uses toggle button 325 to scroll through target server choices. Initially it will be assumed the physician simply selects "No server" using button 325 and the server indicator.

After the physician completes the examination, the physician may review the video clip via viewer 317. If the physician determines that the clip may be useful, the physician may, prior to reviewing the clip again, use button 324 to select a target server. It will be assumed the physician selects a personal archive server as the target server so that the physician can review the clipping later with the aid of medical references in her office. Then, with a target server selected, it is envisioned that any video reviewed will be earmarked for building a target server address. Thus, if a clip is 10 seconds long, the physician may only review a 4 second clip, thereby selecting the 4 second clip for delivery to the target server.

In addition, if desired, by selecting another server via button 325 and reviewing the clip again, the physician can select a second server for building yet another target address for the clip.

After her rounds, the physician accesses a terminal, transmits information packets, including or not including video, depending on what the physician selected, and edits and approves the packets. In this regard, in addition to including the typical HTML formatting information indicated above with respect to the other examples, the packets including video clips provide icons and a viewing window to enable the physician to observe and perhaps edit earmarked video clips prior to storage to a server.

In a second example of how video capable ICD 301 might operate, instead of being used in a medical facility, it will be assumed ICD 301 is used in a jet and maintenance facility for a major airline. In this example, the ICD user is a maintenance technician. It will also be assumed that many jet components include unique bar codes for identifying component parts. For example, a right wing rudder may include a bar code identifying the rudder as a right wing rudder. In addition, the code for a particular jet's right wing rudder may indicate the specific rudder components instead of simply a right wing rudder. For example, the code may indicate "right wing rudder #8821475" so that the specific rudder and its history can be tracked.

In addition, each jet will typically be equipped with a jet specific bar code. While the bar codes may be provided on separate jet components, more typically, a maintenance technician will have a bar code binder or notebook which, for a particular jet, lists all components and the component specific bar codes. Thus, the binder would include an entry "right wind rudder #8821475" which corresponds to the specific jet. During routine maintenance check-ups, the technician is required to carry ICD 301 to collect information for a maintenance report.

During a check-up the technician would first use ICD 301 to establish an association between the jet being examined and the ICD 301. To this end, initially the technician uses ICD 301 to read the jet specifying bar code for the jet or the jet specific binder via reader 323. When the code is read, ICD 301 stores the code and identifies the time and date. At this point ICD can already formulate a good portion of a target server address for the technicians report. As the technician examines the jet, the technician can use ICD 301 to take dictation and identify other specific components via corresponding bar codes from the binder.

When the technician observes the right rudder, it will be assumed that the technician observes a small puncture in the outside skin of the rudder. To document the puncture and subsequently order maintenance services, the technician establishes an association between the right rudder and ICD 301. To this end, the technician locates the right rudder in the binder and uses reader 323 to read the code. The right rudder code is then stored by ICD 301. Next, assuming the puncture is particularly dangerous the technical immediately orders maintenance to repair or replace the rudder. In addition, the technician will want to generate a video clip for archiving so that the puncture is documented for subsequent review and for use by the person who will repair/replace the rudder.

To this end, the technician can use button 325 to scroll through the possible target servers. It is assumed ICD 301 provides a "Maintenance Server" choice. The technician selects the maintenance server as the target server and then collects a video clip of the punctured rudder skin. The maintenance server selection causes ICD 301 to generate a target address specifying the maintenance server for the video clip. Audio information may be provided by the technician during the video clip. In addition, date, time, rudder information, jet identification and technician identification information is added to the video clip for identifying a target address and populating fields in an information packet.

After the examination, the technician accesses a terminal and downloads all information packets for observation. After examining the packet corresponding to the rudder puncture (including the clip), the technician approves the packet information and transmits the information to the maintenance server. Another maintenance technician reviews the video clip and other information provided therewith. Thereafter, the puncture is repaired or the rudder is replaced.

Where maintenance is required prior to flight, in addition to sending the clip to maintenance, the clip and associated information may also be earmarked for a clearance server, personnel associated therewith grounding all jets which require maintenance. In addition, all data collected may be achieved in an archive server regardless of whether or not the archive server is selected by the technician. In yet another example which is related to the previous example, an ICD similar to ICD 301 may be equipped with a lens 315 attached to a technician's head piece or helmet so that everything which is viewed by a technical is captured on video. Thereafter or, during an examination, the technician could earmark certain video clips (e.g. 5-10 seconds) for delivery to specific target server addresses while the entire video is archived on an archive server.

Importantly, it should be noted that preferably content is provided within generated addresses in the present invention. For example, where several facilities share servers, a portion of each server may be earmarked for each facility and therefore all information units or documents for a specific facility should be stored in the corresponding earmarked locations. A portion of each address preferably identifies the facility from which an associated information unit originated. Thus, the address is content specific.

Similarly, for every patient at a facility, preferably, information associated with the patient, is stored at a specific location within the portion of a server earmarked for the facility. As indicated above patient information is also provided in an address. Similar address fields are provided for physician information, type of record, time, date, etc so that virtually an entire address can specify content.

This type of content specifying address is not only intuitive but also very useful in that it makes it relatively easy to retrieve data and information units from storage. In addition, this type of addressing reduces the overall size of an information packet and information units as important content information can be stored in the address.

While a particular embodiment of the invention has been illustrated and described, it will be obvious to those skilled in the art that various changes and modifications may be made without sacrificing the advantages provided by the principle of construction disclosed herein. For example, while the invention is generally described in the context of HTML, clearly the invention is meant to be used with other conventional markup languages or with JAVA or JAVA script program codes. In addition, while the invention is described as being used with a browser, the invention could be used with any terminal which includes software which receives formatting codes and can display information as a function of such codes. Moreover, while it is preferred that full target addresses be provided by an ICD 10, clearly minimal addresses such as a coded address could be provided to a browser wherein the browser would expand the coded minimal address into a full fledged address, the advantage being that the ICD specifies where data is to be stored, not a browser or associated server.

Additional User Authentication Embodiments

In one preferred embodiment of the present invention ICD badge 10 can be configured to only act as an electronic identification and security device and henceforth referred to as security device 10. While it may have the data collection capabilities previously described, they are not required. As before, security device 10 can be in the form security badge or a cell p hone or PDA or other convenient shape that is typically worn or held by an employee of an enterprise, henceforth referred to as computer user. It includes identification text 12 and a photograph of the user and is used to identify the employee to others and to computer resources. Device 10 includes a processor 250 linked to memory 262, activation button 18, indicator 20 (e.g. a LED or speaker), wireless communication transceiver 14, power source (e.g. a battery, photocell, or fuel cell or magnetic field induced power source), and an optional biometric indicia sensor 405 (e.g. a fingerprint sensor placed on the back of device 10). In some cases a small key pad (e.g. buttons 207, 209, 211, 213, and 215 or others) is also provided and display 258 can be provided as a graphic display, e.g. a LCD.

Figure 31:
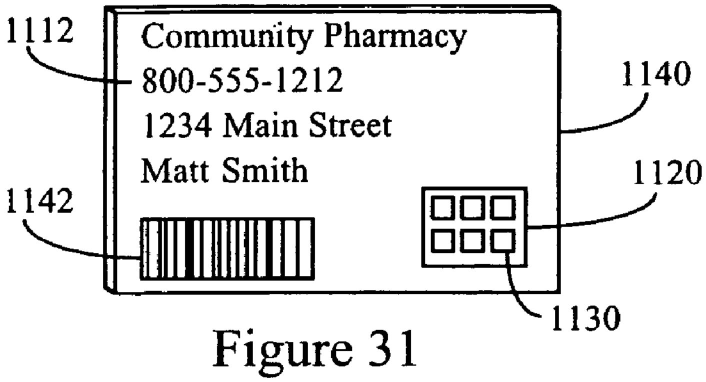
FIG. 31 is a perspective view of an alternate embodiment of the electronic security device now in the form of a smart card.
Figure 32:
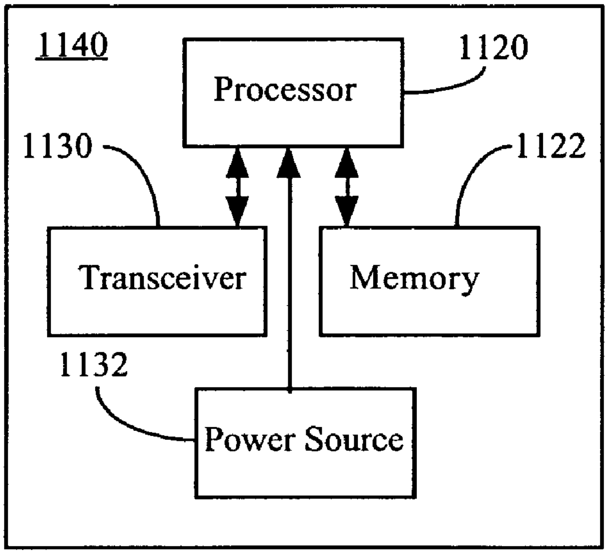
FIG. 32 is an electronic schematic of a smart card.

An alternate embodiment of security device is shown in FIGS. 31 and 32 as smart card 1140, which includes identification text 1112, processor 1120, memory 1122, and transceiver 1130, which may be arranged as a series of electrical contacts or as an RFID tag type antenna. Generally speaking, card 1140 is powered by an external power source 1132 via electrical contacts or by a received energy field such as magnetic, radio, or capacitive coupling. However card 1140 may also include a power source 1132 internal to card 1140 such as a battery. Bar code 1142 can also be used to identify the employee.

It should be noted that while electronic device 10 is shown as an identification badge or smart card it can take a number of forms, such as a portable digital assistant (PDA) or a cellular phone. Generally the invention will refer to device 10, but it is to be understood that card 1140 may be substituted for device 10 in most embodiments.

Figure 33:
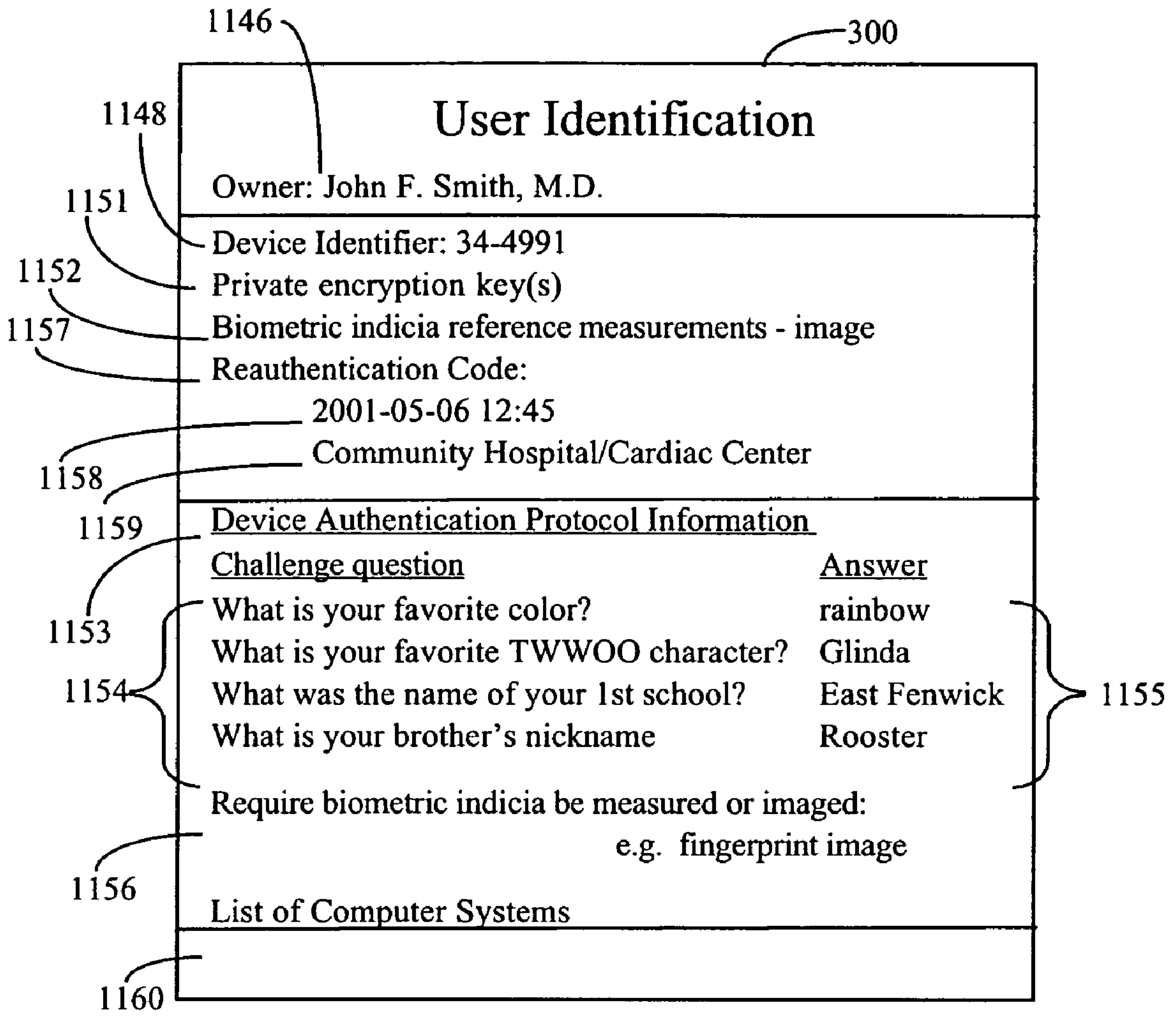
FIG. 33 is a list of the user identification information stored in the electronic security device.

FIG. 33 shows the preferred contents of memory 256 for this embodiment of electronic device 10, now showing information 300 with new detail and expanded fields. As shown, information 300 now includes user identifier 1146 (e.g. his name or an ID number), the security device identifier 1148 (e.g. a serial number or user's name 1146), private keys(s) 1151 used for encrypting or digitally signing information, optional biometric reference information such as biometric indicia characteristics, reference measurements or images 1152 (e.g. fingerprint image), device authentication protocol information 1153 used to authenticate a user to device 10, and reauthorization code 1157. Authentication protocol 1153 can take a number of forms including one or more of challenge question 1154 and answers 1155, but it may also take other forms such as flag 1156 specifying that a biometric indicia be measured or both a challenge question 1154 and a biometric indicia measurement flag 1156.

Typically challenge questions 1154 and corresponding answers 1155 are defined by the user, using questions whose answers will be obvious to the user, but unknown to anyone else who attempts to use device 10. However, question 1154 may simply request a password and the answer 1155 will be a password known to the user.

Reauthorization code 1157 is shown comprised of time component 1158 with optional neighborhood component 1159. It should be noted that additional components can be added as desired. In some cases reauthorization code 1157 is stored at server 168, as will be explained later.

Figure 34:
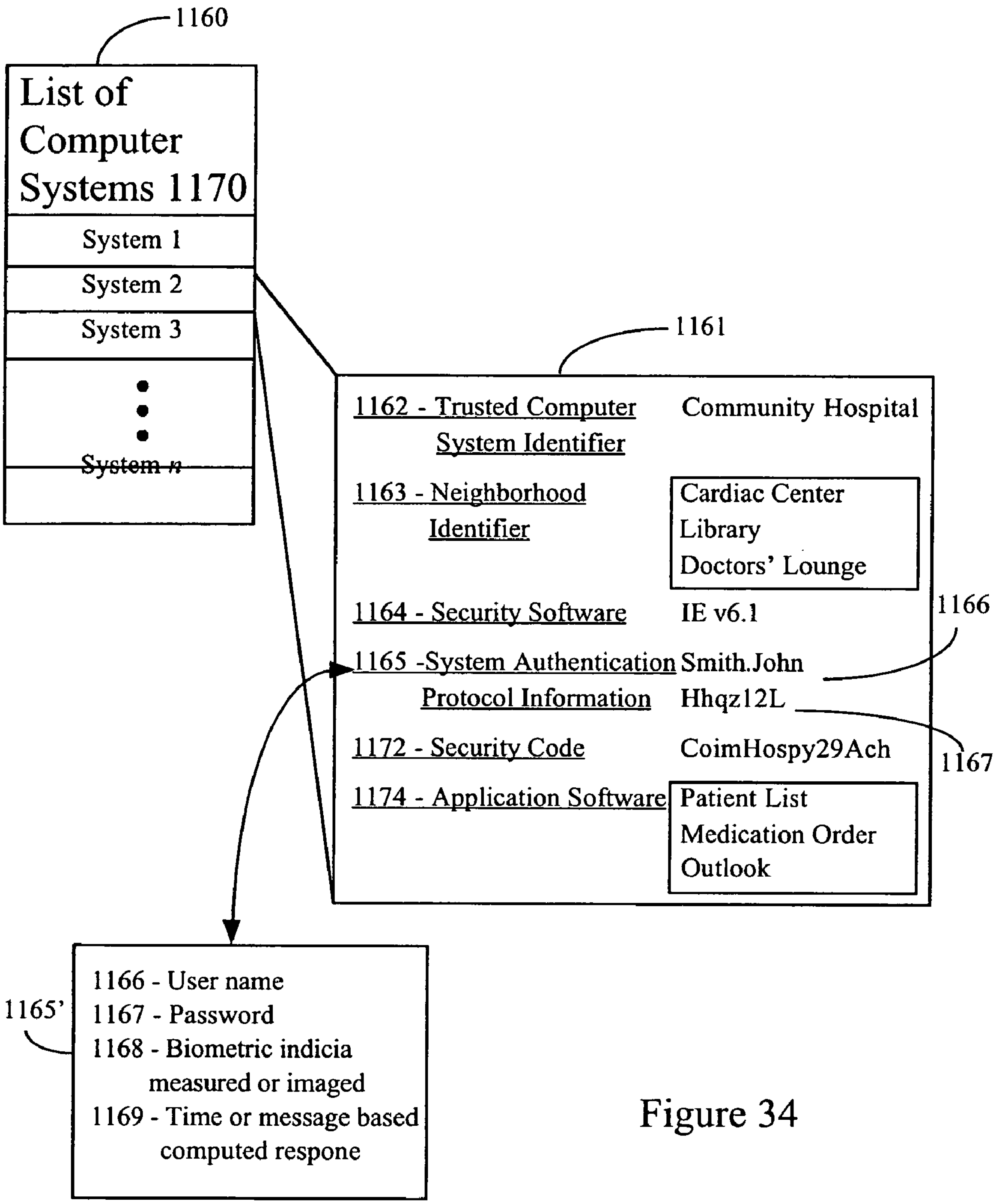
FIG. 34 is a list of the computer system information stored in the electronic security device.

FIG. 34 shows the expanded list of trusted or registered computer system information 1160 stored in memory 262 of device 10. For each electronic or computer system 194 the user is to access, security information 1161 is provided including trusted computer system identifier 1162 that electronic device 10 has been programmed to recognize or trust and may be in the form of a name, a URL address, an internet protocol (IP) address, or other method of identifying a computer system. For each trusted computer system identifier 1162, an optional field indicates the neighborhoods 1163 for each computer system identifier 1162 the user can use to access system 194. Neighborhood 1163 may be all the computer terminals 60 in computer system 194 (referred to by identifier 1162), a group of terminals 60 within a specific physical location (e.g. the library) or terminals that may be spread across the computer system 194 that are associated with a common department or function (e.g. accounting). Neighborhood 1163 can be referred by name, codes, or addresses and a user may have access rights to several neighborhoods.

Information 1160 can include a field that specifies security software identifier 1164 that device 10 will interact with (i.e. trust). This field can specify a software identifier such as a version number, a checksum, or a verifiable software signature that is transmitted to device 10 by software in terminal 60 and/or server 168 prior to it interacting with the software in terminal 60 or computer system 194. This prevents device 10 from providing challenge questions or biometric indicia images or measurements to non-trusted or compromised software.

For each trusted computer system identifier 1162 there can also be stored authentication protocol 1165. As shown computer authentication protocol information 1165 may consist of a user name 1166 and a password 1167. However, protocol 1165 may take a number of forms, such as the requirement that a biometric indicia be measured or imaged 1168 and provided to computer system 1162 or an algorithm 1169 that computes a code or response based on the time or based on a received message and then sends the code to computer system 194 or security device identifier 1148 or combinations of the above. Authentication protocol information may also include portions of user identification 300, e.g. device identifier 1148. Where device authentication protocol information 1153 is used to authenticate a user to security device 10, system authentication protocol 1165 is used to authenticate security device (and therefore its user or owner) to computer system 194.

System authentication protocol information 1165 can consist of a user name 1166 and password 1167 (as may be requested to be provided to most log on software), an indication 1168 that a biometric indicia be measured or imaged, and/or an indication 1169 that the results of a time or message based computation be provided to computer system 194.

For each trusted computer system identifier 1162 there may be list of specific application programs 1174 or functions the user needs or is allowed to use on computer system 194. Program(s) 1174 can be automatically started when the user is authenticated to a computer system 194 or they can be presented as selectable icons.

For each trusted computer system identifier 1162 there may be security code 1172 used to protect neighborhood identifier 1163, software 1164, system authentication information 1165, and any other information stored with identifier 1162. The security code 1174 can take the form of a password, an encrypted code that device 10 can decrypt, or a device identifier 1148 of another device 10 belonging to a trusted computer security staff member. Trusted computer administrative security staff typically provides security code 1174 when information about their system is provided to device 10. Thereafter security code 1174 must be provided to device 10 prior to reviewing or changing system identifier 1162, neighborhood identifier 1163 (when provided), or protocol information 1165. By using multiple security codes 1174 for each trusted computer system 1162, the computer security staff members of one computer system 194 can be assured that no one can review or make changes to the settings he made. This allows device 10 to be used across multiple computer systems 194, where each one has separate and secured settings. In some cases the user of device 10 will not have access to security codes 1172, while in other cases they may.

Figure 35:
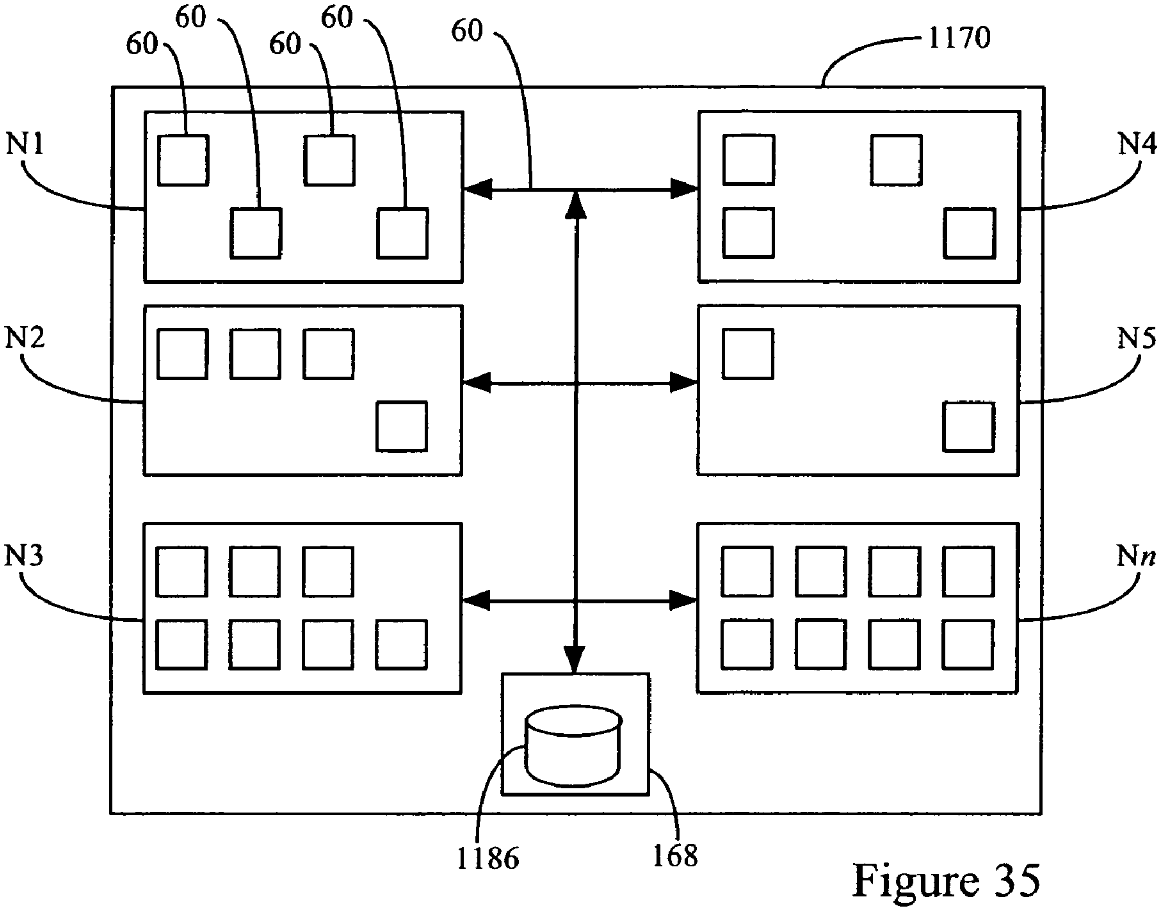
FIG. 35 is a schematic view of the computing network for an enterprise.
Figure 36:
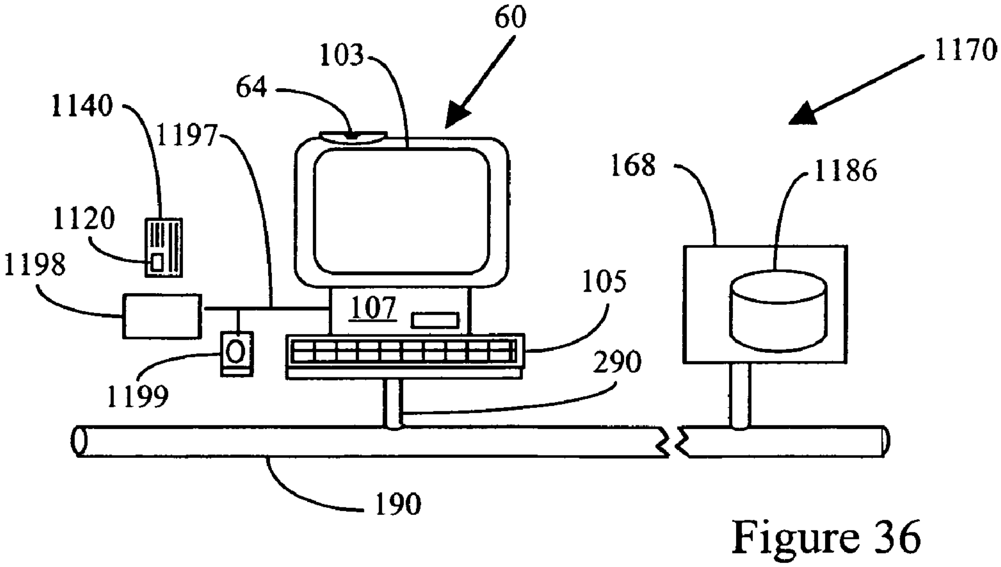
FIG. 36 is a schematic view of a computer terminal attached to computer network.
Figure 37:
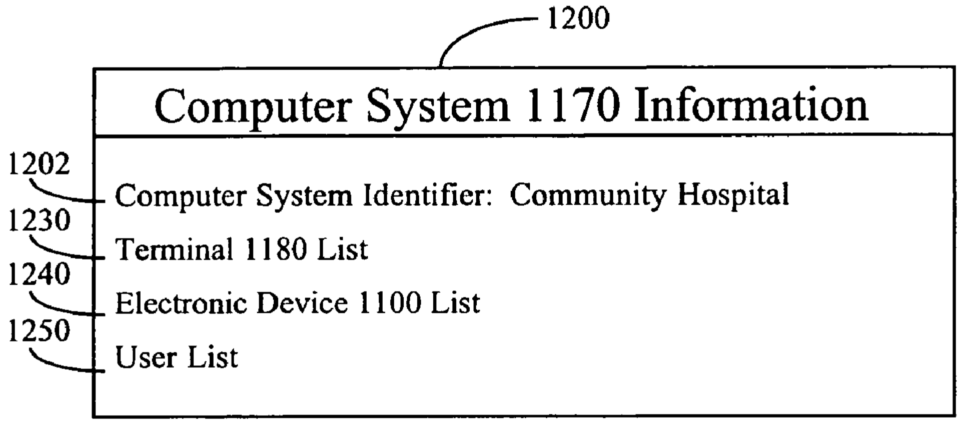
FIG. 37 is a list of information about a computer system stored in a security server.
Figure 38:
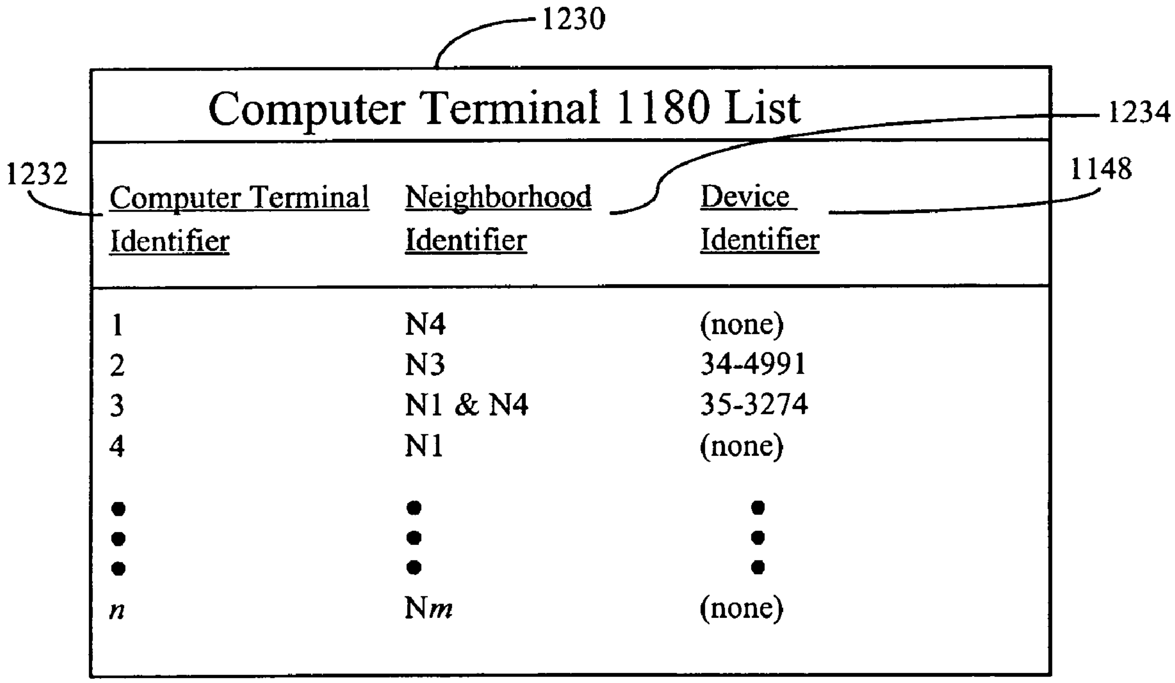
FIG. 38 is a list of terminals that are part of the computer network.
Figure 39:
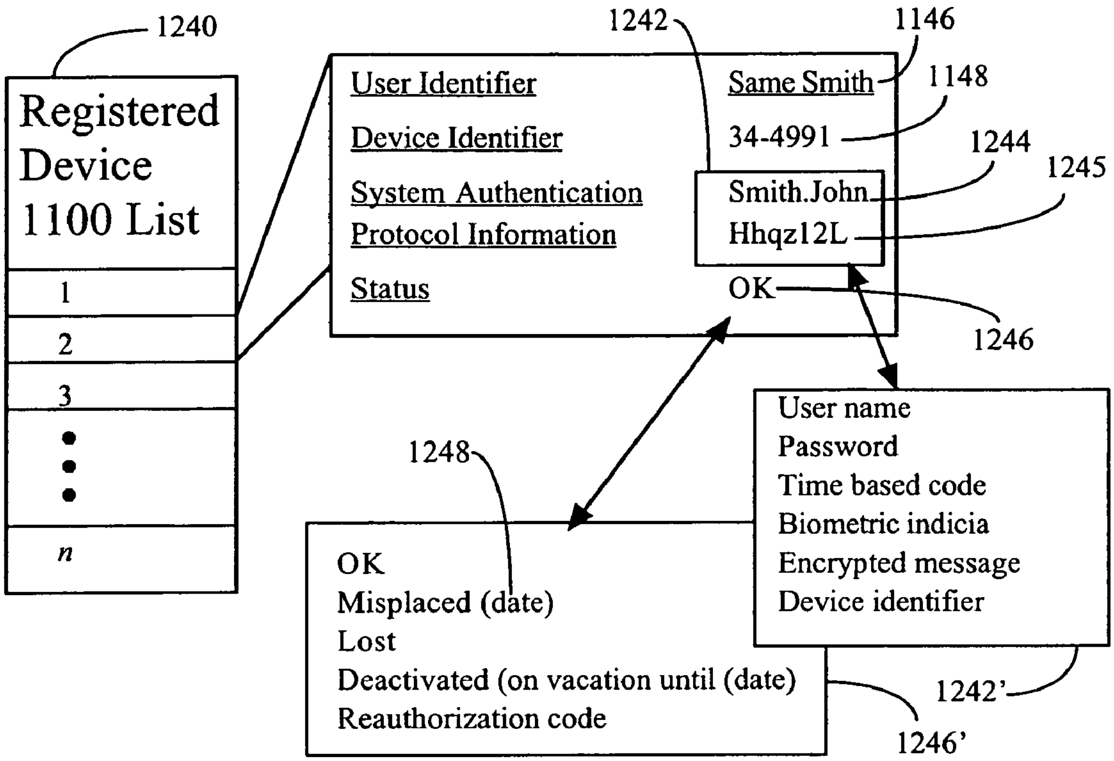
FIG. 39 is a list of electronic security devices that are registered with the computer network.
Figure 40:
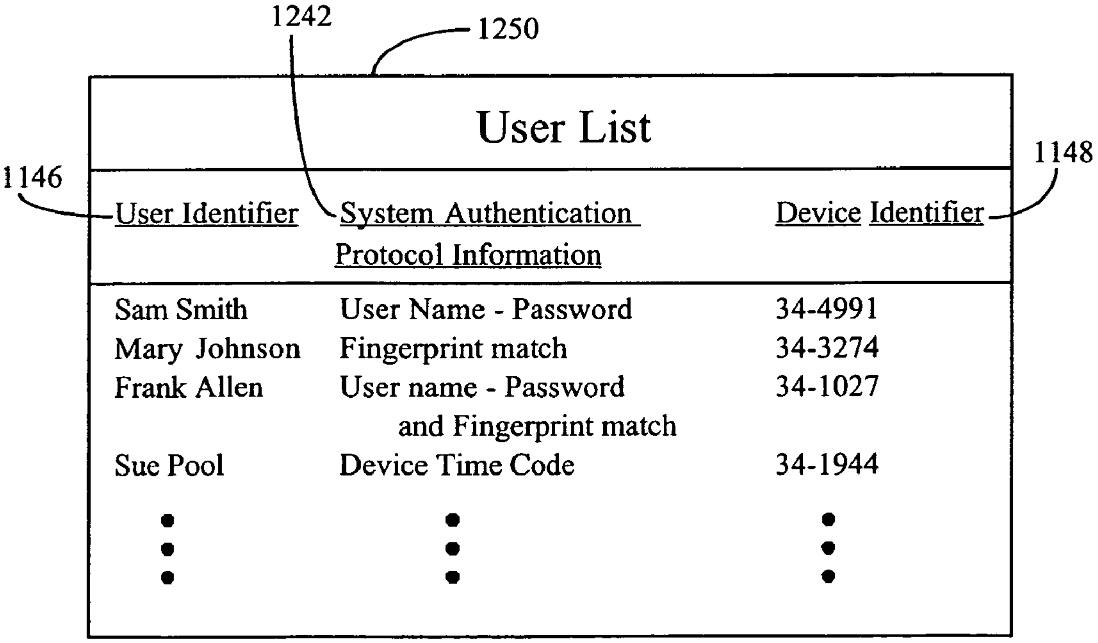
FIG. 40 is a list of users that are registered in a computer system.

FIGS. 35 and 36 shows computer system 194 comprised of computer terminals 60 linked by network 190 to security server 168 and database 1186. Network servers (not shown) and computer resources can be added to network as needed. Terminals 60 are arranged into neighborhoods N1, N2, . . . Nn. As mentioned previously each neighborhood N may be defined by a specific physical grouping, departmental grouping, or other design choice and referred to by neighborhood identifier 1163. A terminal 60 can be a member of two or more neighborhoods N when that definition is convenient to the users. While computer system 194 is shown comprised of several neighborhoods N, it may consist of a just a single neighborhood.

As shown in FIGS. 3 and 36 terminal 60 consists of processor 107 and memory 109 linked to interactive device 105 (e.g. a keyboard, mouse, or voice recognizer), display 103, and transceiver 64, which is designed to communicate with transceiver 14 of device 10. When device 10 is card 1140 and transceiver 14 is a series of electrical contacts, cable 1197 can be used to link processor 107 to smart card interface 1198. When desired processor 107 can be linked to biometric indicia sensor 1199 (e.g. a fingerprint scanner, palm scanner, voice imager).

As shown in FIGS. 37 to 40 it is expected that database 1186 includes information 1200 consisting of computer system identifier 1202, computer terminal list 1230, security device list 1240, and user list 1250 of all users registered to use the all or part of the resources of computer system 194. While shown as separate lists they may be combined in a single database.

Terminal list 1230 is a list of computer terminal identifiers 1232 that are attached to network 190. These are terminals 60 that are trusted by or known to server 168. Identifiers 1232 can be an IP address, and/or a processor serial number, and/or a unique number stored in transceiver 64. For each terminal identifier 1232 there may also be one or more neighborhood identifiers 1163 associated with it. When desired, device identifier 1148 of security device 10 can also be stored for each terminal identifier 1232 when the user corresponding to device 10 is using the terminal 60. When no user is using computer terminal 60 no device identifier 1148 is stored.

Device list 1240 (see FIG. 39) consists of a list of all security devices 10 that have been registered with or trusted by computer system 194. For each device 10 the list includes user identifier 1146, device identifier 1148, and system authentication protocol information 1242 (e.g. a specific user name 1244 and password 1255) that must be provided for to computer system 194 in order to authenticate a user. However an expanded list of authentication protocol information 1242' is also shown from which may include the use of a time varying algorithm, a biometric indicia reference measurement or image, encrypted response message, device identifier, or any of the above or others in any combination that is (are) used by security server 168 to authenticate a user.

For each device identifier 1148 there may also be stored device status 1246. Status 1246 can be used to indicate that device 10 is in normal operation ("OK") and may be trusted or recognized when information 1242 is presented. Expanded list 1246' shows other potential status conditions such as device 10 has been reported by the user as having been misplaced (e.g. thought to be left at home) and may include date 1248 when it was reported missing. Presumably if device 10 is not located and reported found within a period of time as being found, it will be marked as lost. Devices 10 that are reported or marked as lost may cause an alert to be presented if they are attempted to be used with computer system 194. Device 10 can be marked as deactivated for a period of time (e.g. during a vacation) or while waiting for an event to occur (e.g. reassignment to a new user). Other status conditions are contemplated, e.g. device can only be used between 8:00 am and 6:00 pm.

User list 1250 (see FIG. 40) is a list of users that have been registered with computer system 194. List 1250 includes user identifier 1146, authentication protocol 1242 that describes what information the user must provide in order to be authenticated by system 1200, and device identifier 1148 of electronic device 10 used by that user. In some cases list 1250 will be incorporated into list 1240 or visa versa. It is generally assumed that for each register device 10 there is a corresponding user identified by identifier 1146 in user list 1250.

Figure 41:
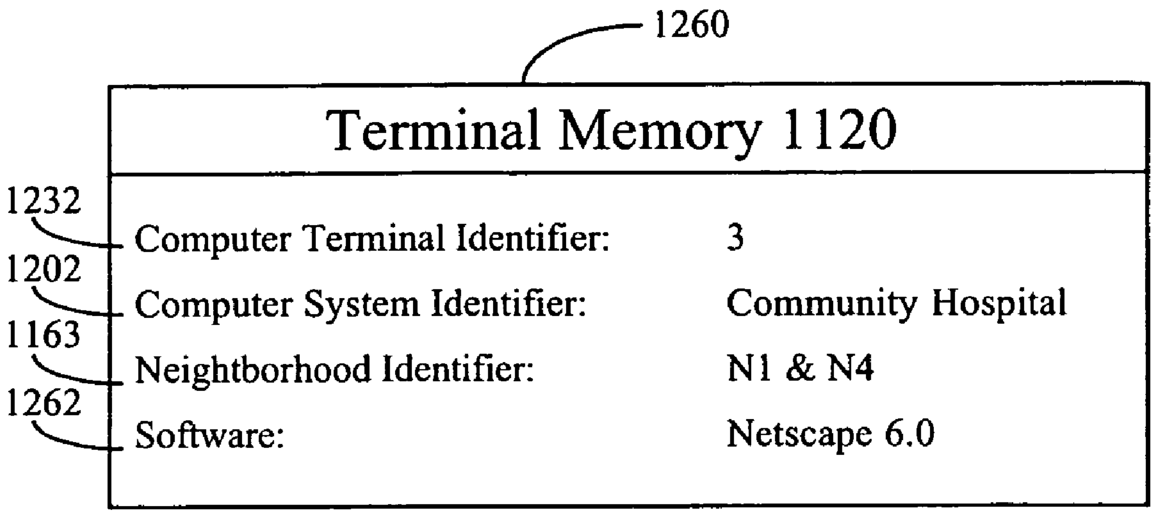
FIG. 41 is a list of information stored in a computer terminal.

Memory 109 of terminal 60 stores computer terminal information 1260 (see FIG. 41), which includes computer terminal identifier 1232, and optionally computer system identifier 1162, neighborhood identifier 1234 (which differs from neighborhood identifier 1163 which is the neighborhoods that's device 10 will interact with), and when desired software identifier 1262 such as a version number, a checksum, or a verifiable software signature (which also differs from security software 1164 that device 10 is intended to interact with). It is anticipated that information 1260 may be stored in transceiver 64 or another device, should storage there be more impervious to hacking or software manipulation. Depending on the software needs of device 10 and terminal 60, information 1260 may not need to be shared with terminal 60. Instead portions of information 1260 can be stored in database 1186 or transceiver 64 and database 1186.

Figure 42:
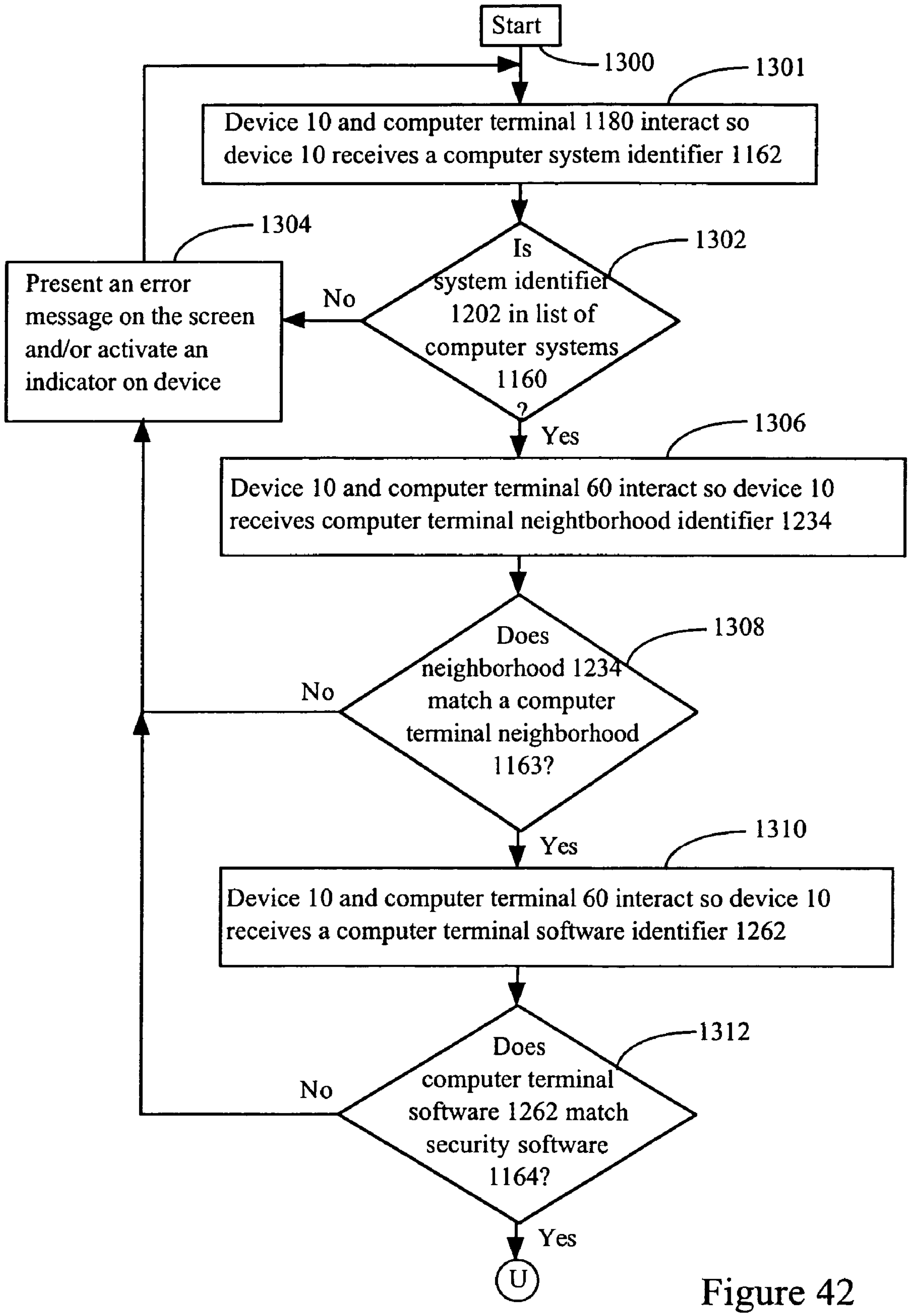
FIG. 42 is a flow chart showing how an electronic security device can verify that a computer system is recognized.

Using of Device 10 to Identify a Trusted Computer System—(FIG. 42)

One use of electronic device 10 is to assist users to verify that computer system 194 and/or computer terminal 60 are trusted or known to electronic device 10.

Transceiver 14 can be under control of processor 250 to repeatedly broadcast device identifier 1148 (or other message) when it is not in communication with a specific terminal 60. This can also be instigated by pressing activation button 18. When the user with device 10 approaches within communication range (e.g. 3 m) of terminal 60, transceiver 64 will receive identifier 1148. Provided terminal 60 is not already communicating with another device 10, it will start communicating with device 10 by transmitting computer system identifier 1162 to device 10 (Step 1301).

Before terminal 60 transmits identifier 1202, it can send a message to security server 168 to check that device identifier 1148 has been registered with computer system 194. If it is not registered or its status 1246 is marked as not approved for use, no further interaction between device 10 and terminal 60 is allowed, an error message can be displayed on display 103, and other staff in the vicinity of terminal 60 can be notified via e-mail, pager, or phone call to assist the person at terminal 60 and to possibly confiscate device 10 as necessary.

While device 10 is described as being powered on all the time, several other steps can be used to establish communication between device 10 and terminal 60. For example, device 10 may require activation button 18 be depressed to place device 10 in an active mode, e.g. to transmit identifier 1148 is transmitted. Device 10 then stays alert waiting several seconds for a reply (e.g. trusted computer system identifier 1202).

In other cases transceiver 64 will repeatedly broadcast a "are any devices present" status message and when device 10 comes within communication range of terminal 60, transceiver 14 will receive the message and processor 250 will respond by transmitting device identifier 1148. As before activation button 18 may need to be pressed for device 10 to receive the message from transceiver 64. After receiving the message device 100 in turn transmits device identifier 1148 and receives computer system identifier 1202. When device 10 is card 1140, it is placed in interface 1198 allowing transceiver 14 to receive system identifier 1202.

In each case the processes described above device 10 and computer terminal 60 interact so device 10 receives computer system identifier 1202. Other communicated messages can be sent and received by device 10. Identifier 1202 can be sent to device 10 first allowing device 10 to validate that system identifier 1202 matches a trusted computer system identifier 1162 in list of computer systems 1160.

Device 10 compares computer system identifier 1202 against the list of trusted computer system identifiers 1162 stored in memory 262 (Step 1302). If there is no match device 10 will no longer communicate with terminal 60 and indicator 20 can be activated or an error message can be sent from device 10 to processor 107, which will present it on screen 103 (Step 1304).

When there is a match terminal neighborhood identifier 1234 may be sent to device 10 (e.g. it may have been included with computer system identifier 1202) (Step 1306), which compares it to system neighborhood 1163 (Step 1308). If there is no match device will no longer communicate with device 10 and indicator 20 can be activated or an error message can be sent from device 10 to processor 107, which will present it on screen 103 (Step 1304). When there is a match the user and device can proceed to a next step.

When there is a match software identifier 1262 may be sent to device 10 (e.g. it may have been included with computer system identifier 1202) (Step 1310). IT is compared to software identifier 1164 (Step 1312). If there is no match device will no longer communicate with device 10 and indicator 20 can be activated or an error message can be sent from device 10 to processor 107, which will present it on screen 103 (Step 1304). When there is a match the user and device can proceed to a next step.

It should be noted that although neighborhoods are described as a subset of computer systems, it is possible to define systems or neighborhoods only, where each system consists of a single neighborhood or where each neighborhood consists of its own system.

Figure 43:
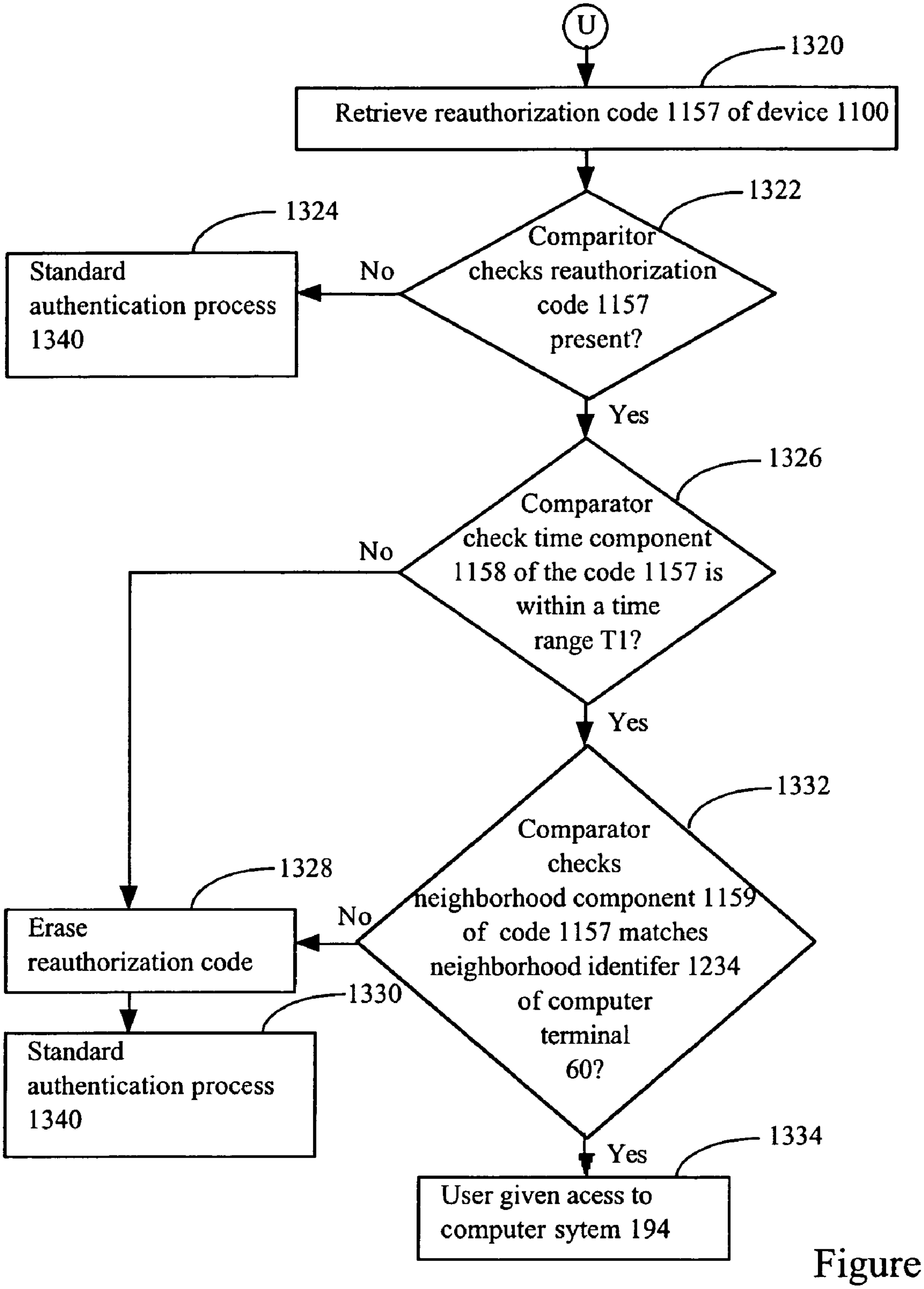
FIG. 43 is a flow chart showing how a reauthentication code can be used to authenticate a user to a computer terminal.

Using Device 10 to Determine if the User Needs to be Authenticated—(FIG. 43)

To determine if the user must authenticate himself, reauthentication code 1157 is retrieved (Step 1320). A check is made to determine if code 1157 is present (Step 1322). If code 1157 is not present, e.g. the first time the users uses computer system 194 in a day, the user must log onto computer system 194 using the standard authentication process 1340 (Step 1324). When reauthentication code 1157 is present, time component 1158 is compared to the current time to see if is within a time range T1 retrieved (Step 1326), for example within 4 hours. Time component 1158 is based on a time relative to a previous successful standard authentication process, e.g. it may be the time of the authentication was performed or the time the user left any terminal 60. When time component 1158 is not with range T1, reauthentication code 1157 is erased (Step 1328) and the user must log onto computer system 1162 using the standard authentication process 1340 retrieved (Step 1330).

When time component 1158 is within range T1, computer system-neighborhood component 1159 is compared against computer system 1202 and neighborhood identifier 1163 of terminal 60 (Step 1332). When component 1159 does not match computer system identifier 1202 or terminal neighborhood identifier 1163, reauthentication code 1157 is erased (Step 1328) and the user must log onto computer system 1162 using the standard authentication process 1340 retrieved (Step 1330), which may be part of a system security function. In some cases an error message may be presented on display 103. When component 1159 is matched the user is given access it computer system 194 without further authentication being necessary (step 1334).

Other component tests can be performed to determine that both device 10 and computer system 194 recognize or trust each other, e.g. by using a third party certificate verification service.

While device 10 was described as performing the above comparisons, security server 168 or terminal 60 may perform the comparisons regarding reauthentication code 1157 and code 1157 instead of being stored in device 10 can instead be stored in database security server 168 as part of user list 1250.

Figure 44:
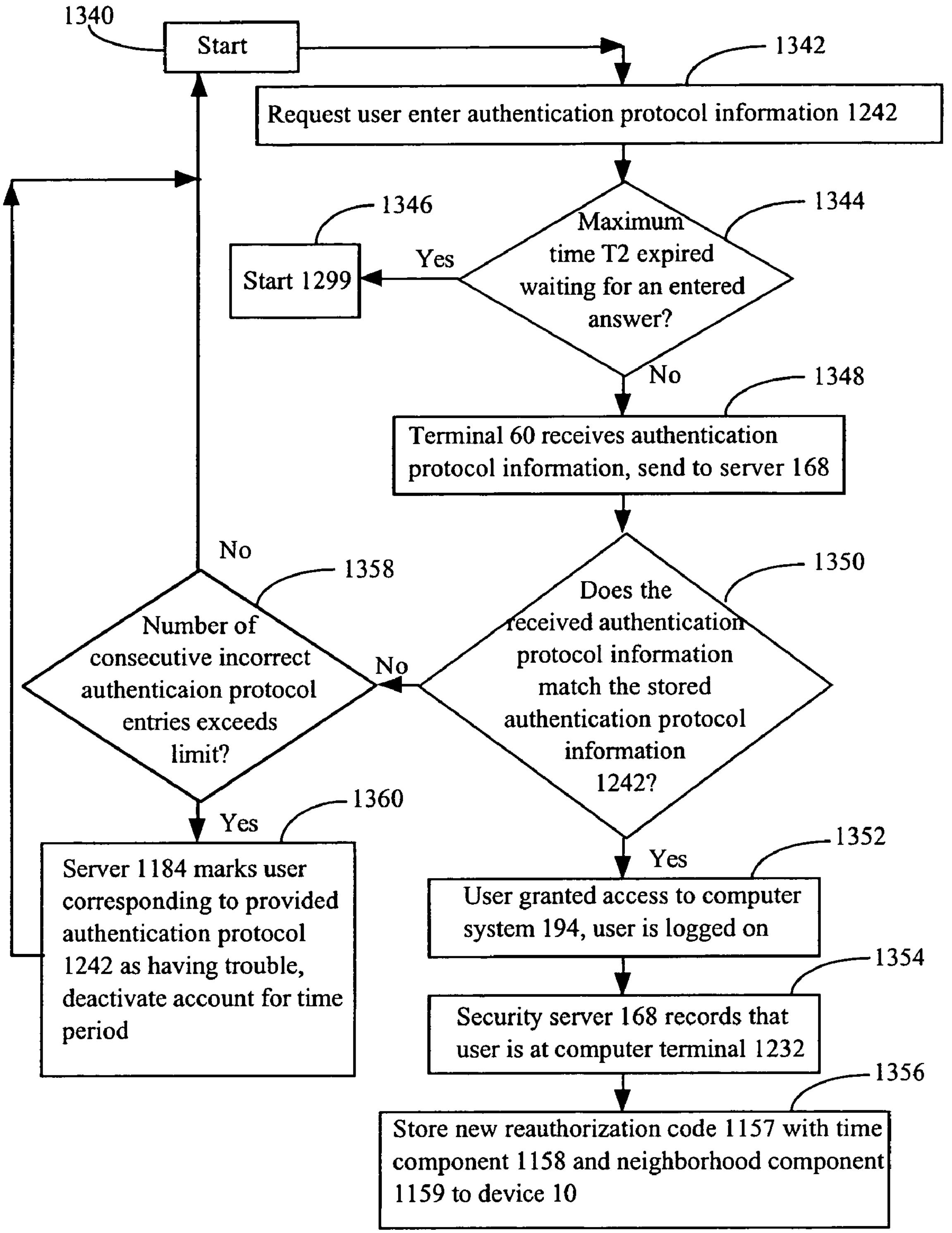
FIG. 44 is a flow chart showing how a user authenticates himself to a security server.

The Standard Authentication Process 1340—(FIG. 44)

To authenticate a user in the standard process may consist of the user entering system authentication protocol information 1242 (Step 1342), e.g. user name 1244 and password 1245 via interactive device 105 or for device 10 to provide system authentication protocol information 1165 for a specific computer system 194. If this is not provided within a time limit T2 (Step 1344) the entire process is restarted (Step 1346). When authentication protocol is provided it is transmitted to security server 168 (Step 1348), which searches database 1186 for matching system authentication protocol information 1242. This may be assisted by using the entered user name and searching database 1186 for a matching user name 1244 and then comparing the corresponding password 1245 stored in database 1186 against the entered password (Step 1350) (see authentication protocol 1242).

If there is a match the user is authenticated and logged on (Step 1352), security server 168 records that user 1146 is using computer terminal 60 associated with terminal identifier 1232 (Step 1354), and an appropriate reauthorization code 1157 is created and transmitted to device 10 for storage in memory 262 (step 1356) or for storage in status 1246.

Standard authentication process 1340 may also include requesting the user allow biometric indicia sensor 405 or 1199 to measure or image a user biometric indicia. The sensed measurements or image can be compared against all other biometric indicia measurements defined in system authentication protocol information 1242 stored in database 1186 of security server 168, or the comparisons can be limited to those of a single user identified by an entered user name or by user identifier 1146 provided by device 10. If there is a match the user is authenticated to computer system 194 and logged on.

Security server 168 records that the user corresponding to user name 1166 or user identify 1146 is now using terminal 60 corresponding to terminal identifier 1232.

If there is no match between entered authentication information and system authentication protocol information 1242 a count is maintained of the number of times this occurs and a is compared against a limit (Step 1358). If it is less than the limit (e.g. 5 tries) the user is requested again to enter authentication protocol information 1242 (step 1342). If the limit is exceeded, a message is sent to security server 168 that the user corresponding to user identifier 1146 or user name 1166 is having trouble authenticating himself (Step 1360), which may be part of a system security function. Server may deactivate the user's account for a period of time and present an error message for presentation on display 103. When appropriate the manager of computer system 194 may specify that a security device 10 security function be performed to the memory 262, e.g. erasing some or all of information 300, especially that related to computer system 194 (see Step 1490). The authentication process recommences at Step 1300.

As previously described, the log on process can be conditioned by requiring that computer system 194 matches one stored in list 1160, that the neighborhood corresponds to one defined in 1163 (when provides) and that the security software 1262 of terminal 60 matches security software 1164.

Figure 45:
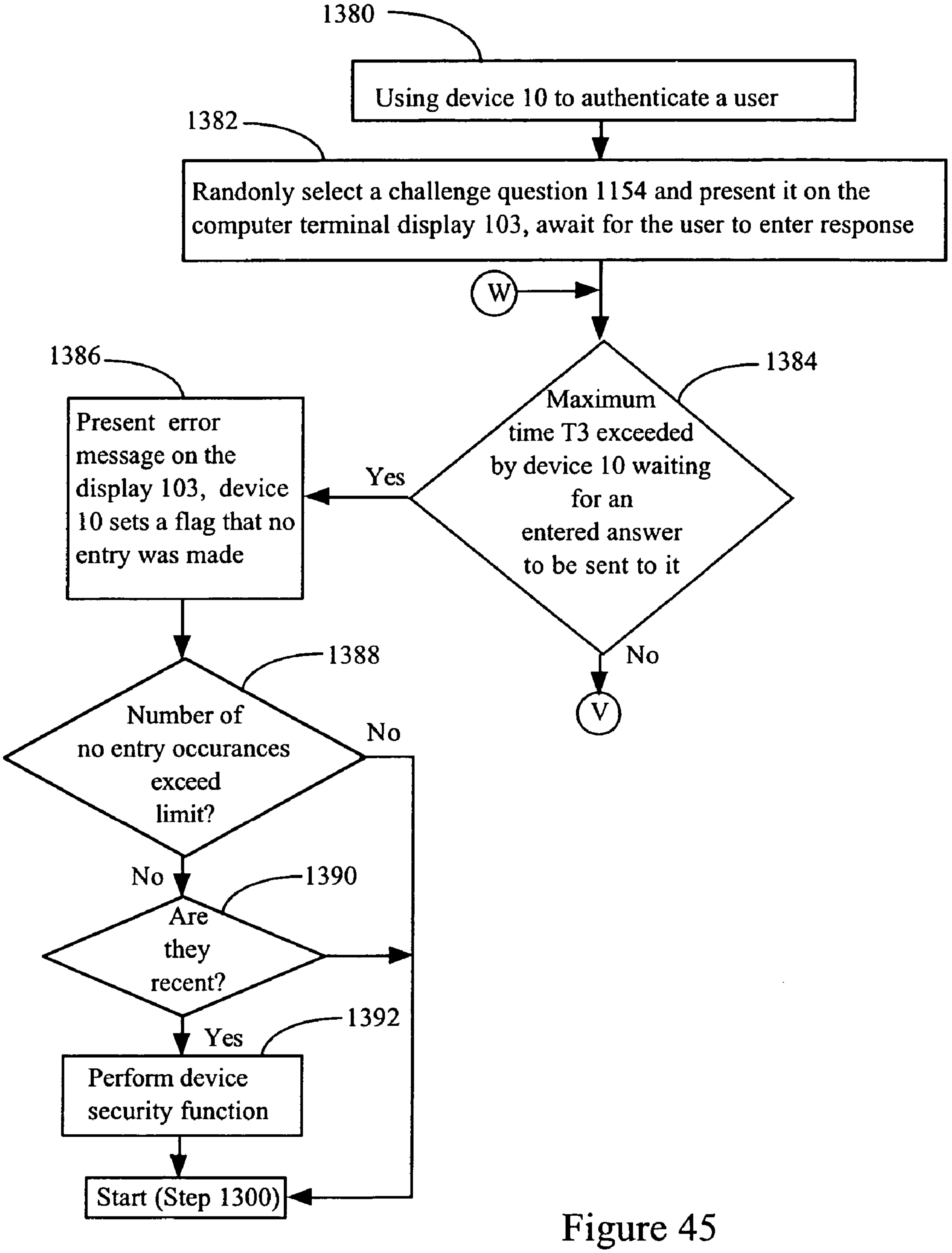
FIG. 45 is a flow chart showing how an electronic security device can be used to authenticate a user.
Figure 46:
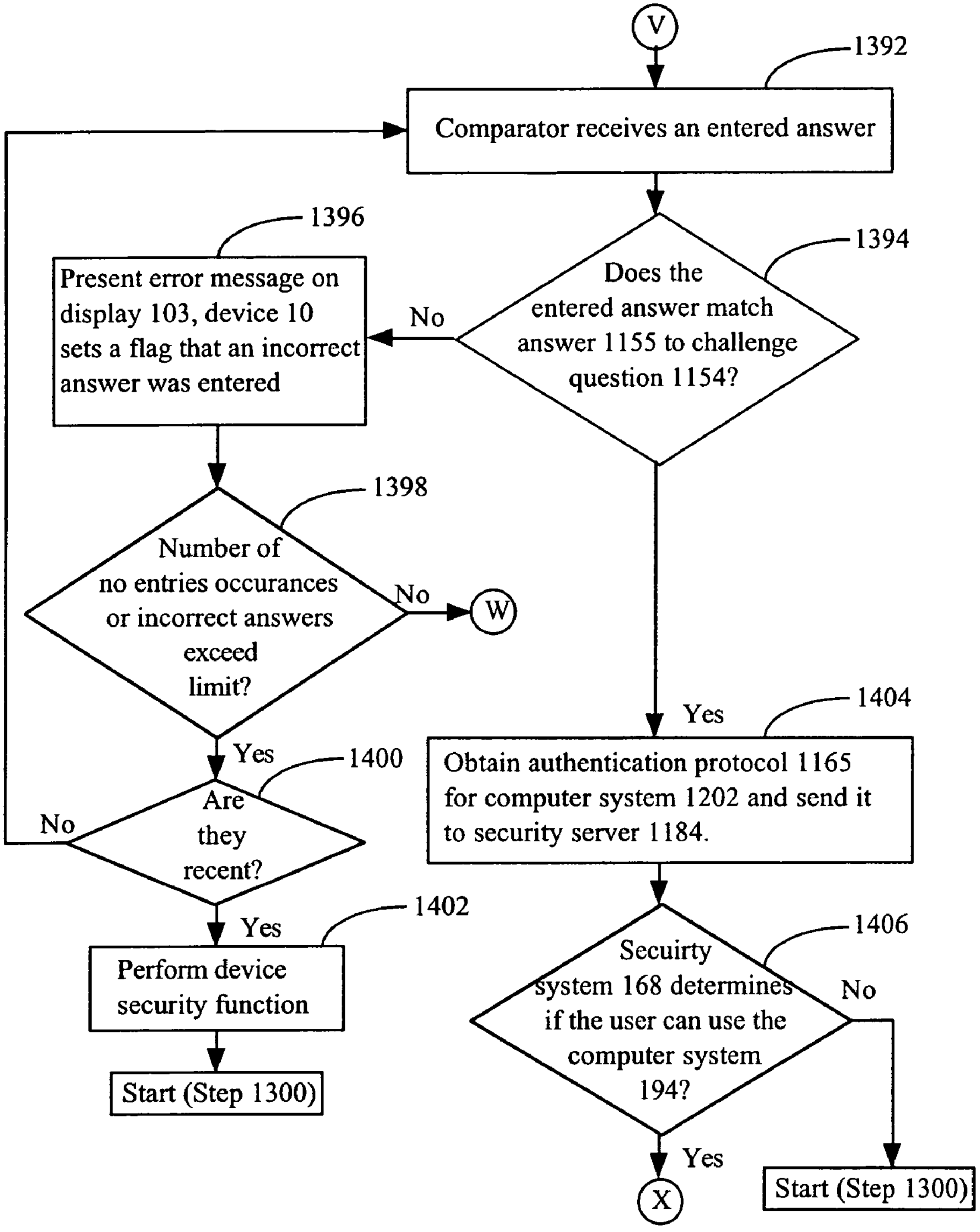
FIG. 46 is a flow chart further showing how an electronic security device can be used to authenticate a user.
Figure 47:
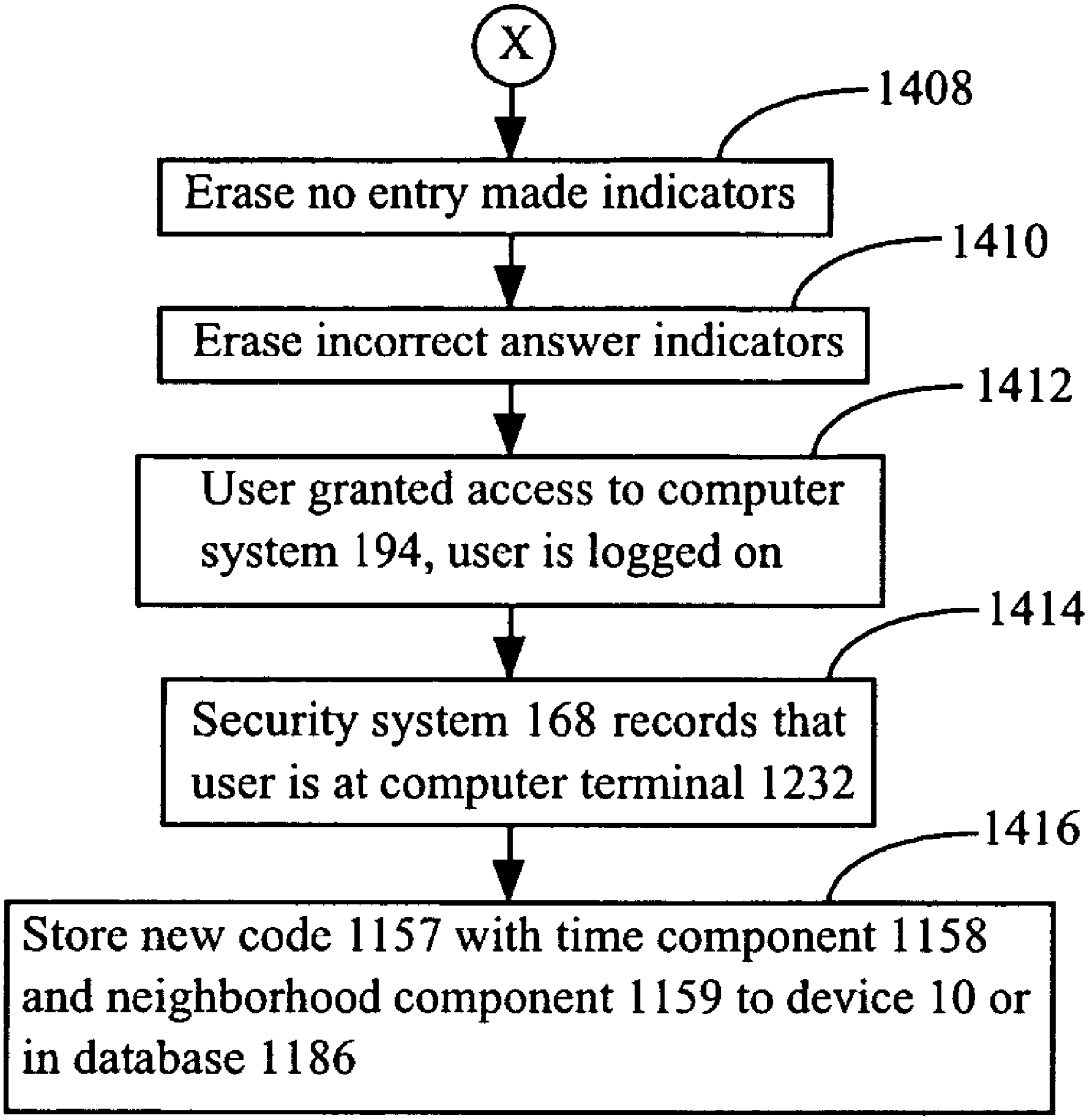
FIG. 47 is a flow chart further showing how an electronic security device can be used to authenticate a user.

Using Device 10 to Authenticate a User—(FIGS. 45 to 47)

To improve the authentication process, the user may need to authenticate himself to security device 10 in order for device 10 to provide system authentication protocol information 1165 to security server 168, which in turn authenticates the user 1380. The user must initially provide device authentication protocol information 1153, which may be in the form of a number of challenge questions 1154 and corresponding answers 1155, to device 10. To authenticate himself to device 10 challenge question 1154 can be randomly retrieved and transmitted by device 10 to terminal 60 for presentation on display 103 (step 1382). In some cases the challenge question is presented on display 16 of security device 10. The answer to the challenge question can be entered using an input device such as activation button 18, a small key pad or touch screen (not shown) on security device 10. Using a security device input device for entering the answer prevents any software in terminal 60 from secretly recording the answer. However, question 1154 (e.g. a request for a password) can be sent to terminal 60 for presentation on display 103 and the answer (e.g. a password) can be entered using input device 105.

If there is no response within time limit T3 (e.g. 30 seconds) to the request for an answer (Step 1384), device 10 can present an error indication by sending a message to terminal 60 for presentation on display 103 or by activating indicator 20. This event is added to a list device 10 maintains of requests to provide a challenge question without an answer being provided in time T3 (Step 1386). When a significant number of these events occur (Step 1388), especially if they tend to be recent (although timing need not be a criteria) (Step 1390) it can be evidence of an attempt to hack, guess, or otherwise defeat the authentication of the user to device 10 and a device security function is performed (e.g. see Step 1490) (Step 1392). Following the security function the authentication process recommences at Step 1300.

When the user enters an answer via interactive device 105 (step 1393) device 10 or computer terminal 60 is provided with the corresponding answer 1155, which is compared against the user entered answer (Step 1394). If they do not match an error message can be presented by display 103. The message is generated by terminal 60 when processor 107 performs the comparison and is sent to terminal 60 when processor 250 performs the comparison. Next a flag is stored in memory 262 indicating this error event (step 1396). A determination by device 10 (or by terminal 60) is made to determine if there the number of these events has exceeded a limit (Step 1398) especially if they tend to be recent (although timing need not be a criteria) (Step 1400). This can be evidence of an attempt to hack, guess, or otherwise defeat the user authenticating himself to device 10 and a device security function is performed (e.g. see Step 1490) (Step 1402). Following the security function the authentication process recommences at Step 1300.

It should be noted that it is preferable, but not required, that answer 1155 is not provided to terminal 60 in order to maximize the security of this information.

If there is a match, user is authenticated to device 10, which then retrieves stored system authentication protocol information 1165 (e.g. user name 1166 and password 1167, a time varying algorithm to compute a time based response code, or other user unique code, or a measured biometric indicia) corresponding to the computer system 194 as in list 1170. The authentication protocol information 1165 is then sent to server 168 (Step 1404) for comparison with system authentication protocol information 1242 (Step 1406) for the user identified by device 10. If there is a match the user is authenticated to computer system 194 and logged on.

Authenticating a user to device 10 using device authentication protocol information 1153 can include presenting a biometric indicia to sensor 405, which measures or images the indicia. Processor 250 then compares it to biometric reference information, measurements, or images 1152 stored in memory 262. When there is a match the user is authenticated to device 10, which then retrieves stored authentication protocol 1165 (e.g. user name 1166 and password 1167, a time varying algorithm to compute a time based response code, or other user unique code) for corresponding to received computer identifier 1202. System authentication protocol information 1165 sent to security server 168 for comparison with authentication protocol 1242. If there is no match the authentication process recommences at Step 1300.

If there is a match the user has been authenticated to computer system 194. Any previous "no answer provided" or incorrect answers events that have been recorded can be erased (Steps 1408 and 1410), since the user has authenticated himself to device 10. It should be noted that Steps 1408 and 1410 can be performed prior to the user being authenticated to system 194, as the user has at least been authenticated to device 10.

The user is granted access to computer system 194 and logged on (Step 1412). Security server 168 records that the user corresponding to user name 1166 is now using terminal corresponding to terminal identifier 1232 (Step 1414). With the user authenticated to computer system 194, computer terminal 60 now writes reauthorization code 1157 to device 10 for later use (Step 1416). It can also be held by security server 168. As previously stated code 1157 may include time component 1158 based on the current time of authentication and computer system and neighborhood component 1159 of the neighborhood Ni corresponding to terminal 60.

While in the above discussion biometric indicia is measured by sensor 405 and compared by device 10 some of the process can be performed by computer terminal 60. For example in some cases the biometric indicia is measured or imaged by sensor 1199 and transmitted by transceiver 64 to device 10, which performs the comparison. In other cases the biometric indicia is measured by sensor 405, which is transmitted along with biometric reference measurements 1152 to computer terminal 60 for comparison or the indicia is measured by sensor 1199 and compare to measurements 1152 by computer terminal 60.

For optimal security it is preferable, but not required, that biometric reference measurements are not transferred to any terminal 60 or computer system 194. Each transfer opens the possibility for others to gains access to this information.

Figure 48:
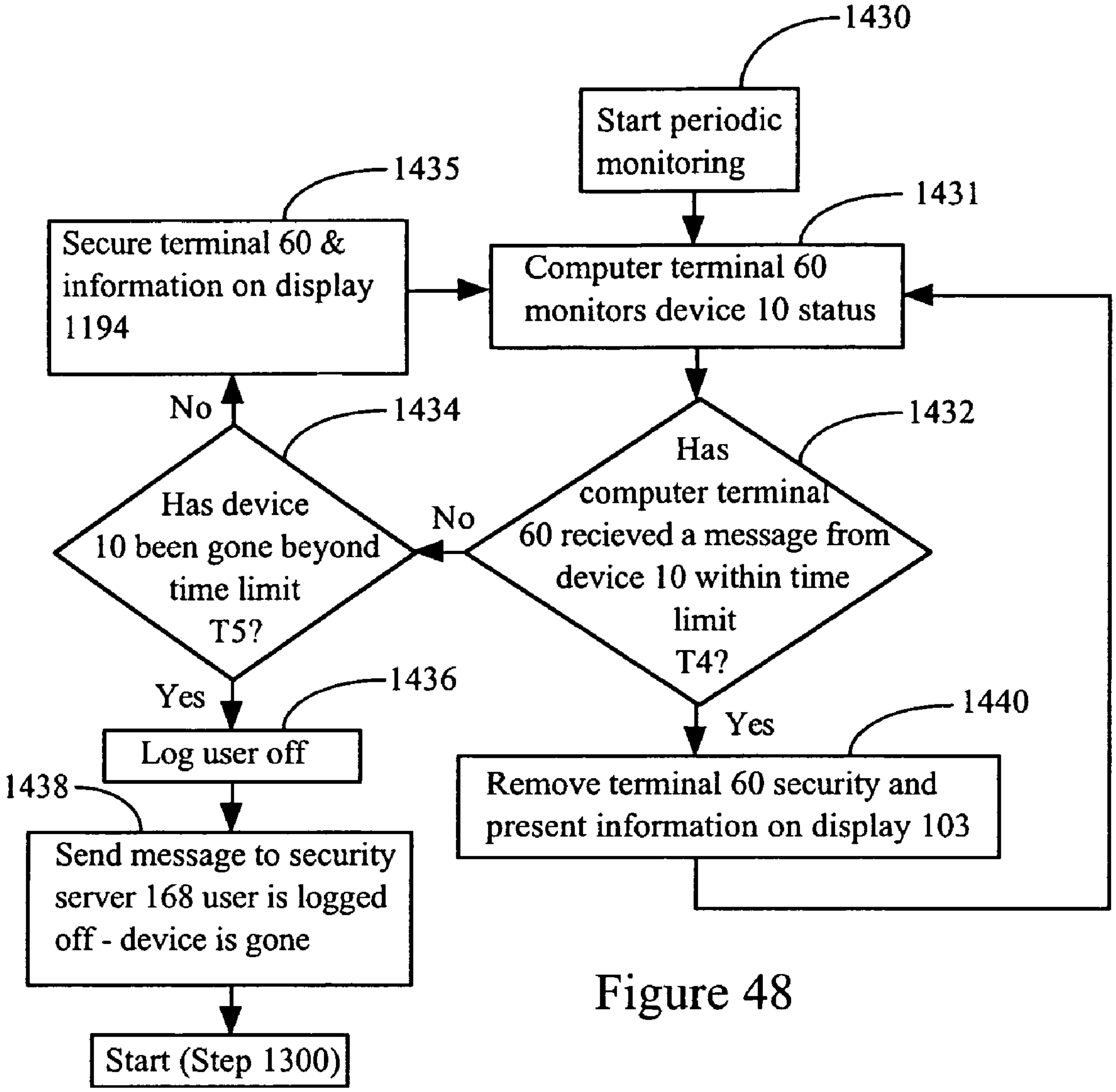
FIG. 48 is a flow chart showing how a computer terminal monitors for the presence of an electronic security device to maintain access for the user.

Monitoring Security Device 10 to Detect User Departure—(FIG. 48)

Once the user has been authenticated by computer system 194, the user uses computer terminal 60 and the resources of computer system 194. When the user is finished using computer terminal 60 two methods are commonly used to determine the user has left terminal 60. First the user may take steps to indicate to software on terminal to log him off. Secondly, the user may leave terminal 60, in which case software in terminal 60 detects that interactive device 105 remains inactive in excess of a time limit (e.g. 3 minutes) then software in terminal 60 determines the user has likely left and will log the user off.

However, the first method requires active steps be taken by the user which may delay them from other activities (e.g. a healthcare worker being called to an emergency) and the second allows the security threat of any new user who starts to use terminal 60 within the time limit complete access to computer system 194 as though they are the previous user.

After device 10 is used to authenticate a user to computer system 194 terminal 60 can start to periodically monitor that device 10 is present (Step 1430). When device 10 is kept within range of terminal 60 (or card 1140 left inserted in reader/writer 1198 its status can be monitored (Step 1431). This can be done by terminal 60 using transceiver 64 to broadcast an interrogation signal including device identifier 1148. Device 10 when it receives the signal responds with a return response (see above) or status message back to terminal 60.

Alternately device 10 may broadcast a status message identifying itself on a periodic basis to terminal 60. A comparison is made to determine if terminal 60 has received a status message within a period of time T4 (e.g. 30 seconds) (Step 1432). A further test can be made to determine if no message has been received within longer time limit T5 (e.g. 10 minutes). If time limit T5 has not been exceeded terminal 60 can take steps to secure itself (Step 1435) by limiting access; for example it can secure display 103 by removing any previously shown data and replace it with a message indicating that device 10 cannot be detected and that the user is soon to be logged off terminal 60; which may be part of a system security function. Limiting access can also include locking one or more of the terminal interactive device 105 such as a keyboard or a mouse; it can also include disabling the connection between terminal 60 and network 190 so as to limit access to computer system information, which may also be part of a system security function.

If time limit T5 is exceeded then the user access is further limited by logging him off terminal 60 (Step 1436) and a message is sent to security server 168 that the user is no longer present (Step 1438). In some cases the user is logged off immediately when time limit T4 has been exceeded (T5=T4). If a new user with his own electronic device 10 is sensed between T4 and T5 terminal 60 can automatically log the previous user off and proceed to allow the new user to authenticate himself to security server 168. The previous user's device identifier 1148 is removed from list 1230 and the new user's device identifier is inserted if they are authenticated to system 194.

When a status message is received by terminal 60 within time limit T5 the user can continue to use terminal 60 at the point they had previously being using it and any terminal security measures are removed (Step 1440).

When terminal 60 transmits interrogation signals, device 10 receives them to determine when it is near terminal 60. As stated before, device 10 can transmit response messages related to the interrogation signals. When device 10 has not received an interrogation signal within a period of time it can determine that it is no longer in communication with terminal 60 and erase any information about its interaction with terminal 60 in memory 262, although reauthorization code 1157 is preferably retained. Device 10 can also switch to an inactive mode, for example a powered down or power restricted mode.

Figure 49:
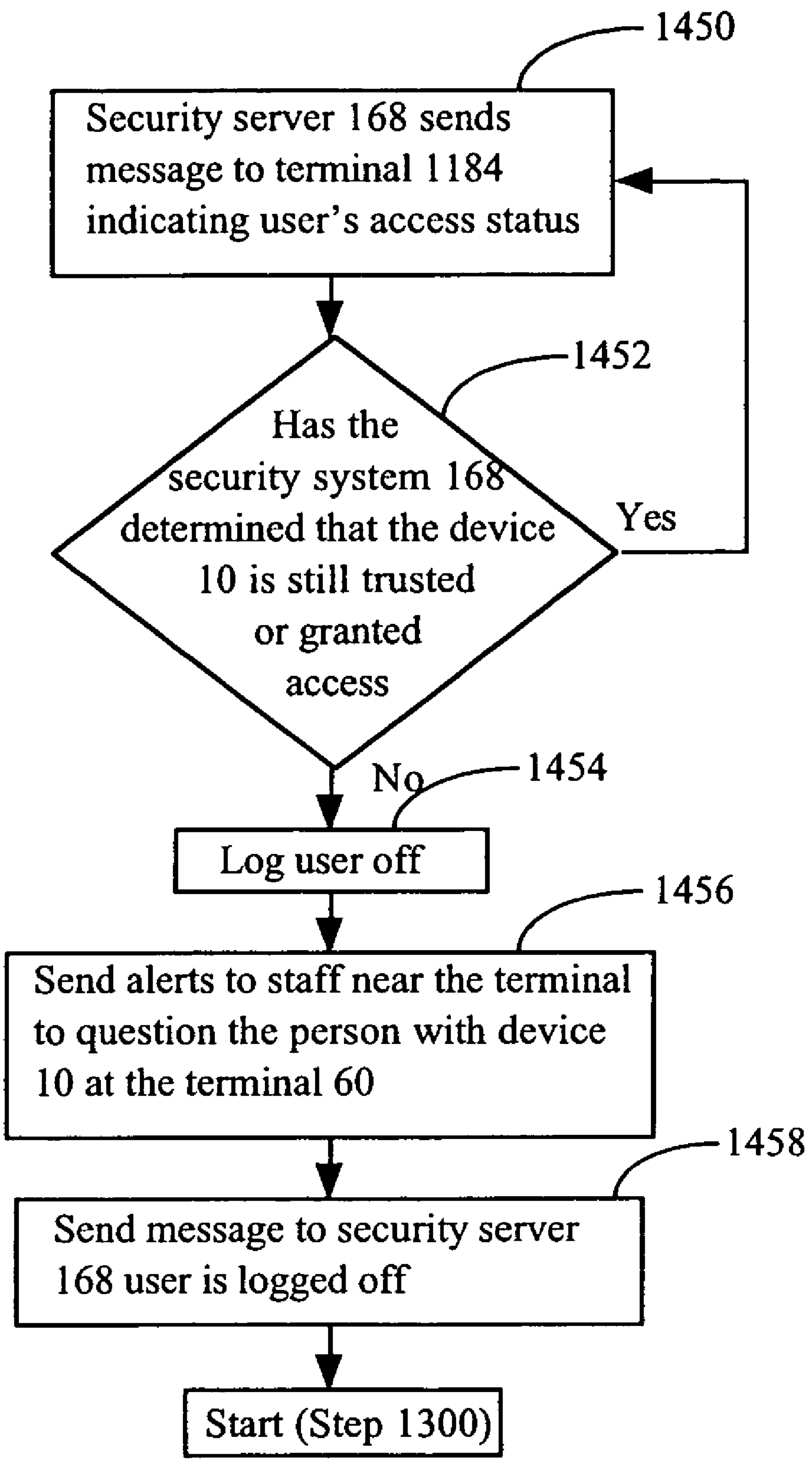
FIG. 49 is a flow chart showing how a security system can determine that a user who was authenticated by electronic security device should be logged off.

Monitoring User of Device 10 is Still Authorized to Use Computer System 194—(FIG. 49)

A request can be made episodically from terminal 60 to security server 168 requesting the most current user access status 1246 (Step 1450) to determine if the user identified by user identifier 1146, device identifier 1148, or user name 1166 is still trusted or granted access to computer system 194, e.g. to cancel access privileges if a user reports their badge or security device 10 stolen. In some cases security server 168 dynamically sends a message regarding the access status of the user's or device 10 to detect if it has changed. Terminal 60 determines if the user is still trusted (Step 1452). If they are still granted access the user continues to use computer terminal 60.

If device 10 or the person using it is no longer granted access they are logged off terminal 60 (Step 1454), a message can be sent to nearby staff (e.g. by e-mail, pager, or phone) to recover device 10 or otherwise assist the user (Step 1456), and a message can be sent back to server 168 that the user has been logged off. When appropriate the manager of computer system 194 may specify that a security function be performed to the memory 262, e.g. erasing some or all of information 300, especially that related to computer system 194 (see Step 1490). The authentication process recommences as Step 1300.

Figure 50:
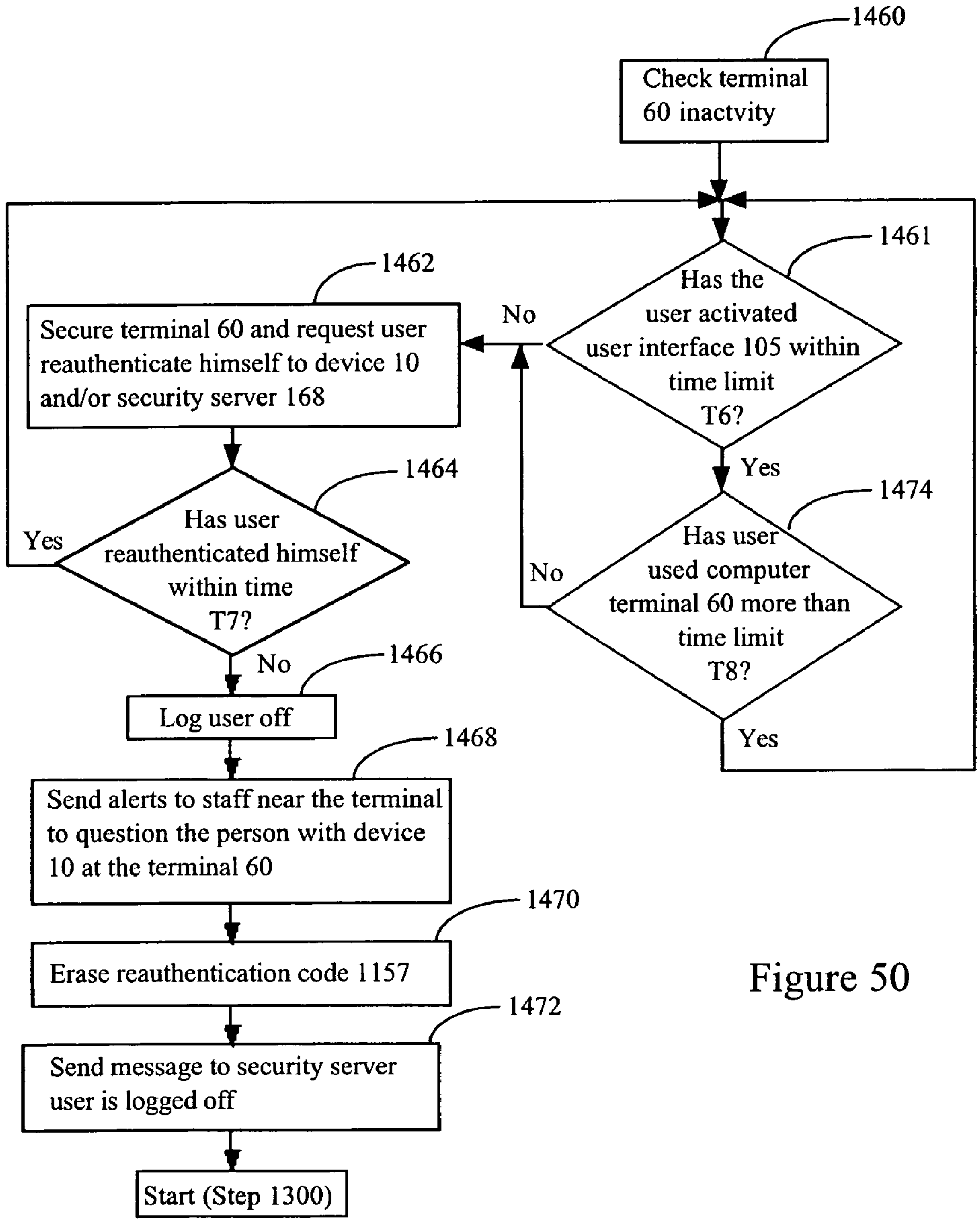
FIG. 50 is a flow chart showing how a computer terminal can detect that a user is no longer present at a terminal.

Monitoring Terminal 60 Inactivity—(FIG. 50)

Even while terminal 60 is able to detect device 10 (e.g. by receiving status messages) it remains possible that the use has left his device 10 (especially likely when card 1140 is used). In this case any one who uses terminal 60 will have complete access to it. To prevent this user interface 105 can be monitored periodically for activity (Step 1460), e.g. a lack of use or activation of interactive device 105 or other. If it remains inactive for a period longer than a time limit T6 (e.g. 3 minutes) (Step 1461), terminal 60 can either log the user off or secure terminal 60 and present a message asking the user to reauthenticate himself in some way to device 10 (e.g. by responding to challenge question 1154) or security server 168 (Step 1462). If the user fails to reauthenticate himself within period of time T7 (e.g. 30 seconds) (Step 1464), he will be logged off terminal 60 (Step 1466).

Furthermore a message indicating that the user may have left behind device 10 can be sent to security server 168. Server may mark status 1246 for device 10 as being left behind. A message can be sent (e.g. by e-mail, pager, or phone) to other staff near terminal 60 to secure device 10 so that it is not stolen or otherwise misused (Step 1468).

Any reauthentication code 1157 in device 10 can be erased (step 1470) to prevent code 1157 from being used reauthenticate a user to a terminal 60 as described above.

A message is sent to security server 168 indicating the user has been logged of because they could not reauthenticate himself even though device 10 was present. Sever 168 can maintain information about users that leave their device 10 at terminal 60. Users that to do this repeatedly can be reminded of the importance of computer security and may have their security privileges removed. When appropriate the manager of computer system 194 may specify that a security function be performed to the memory 262, e.g. erasing some or all of information 300, especially that related to computer system 194 (see Step 1490).

Reauthenticating a User who had Been Previously Authenticated—(FIG. 50)

In some cases it is desirable to reauthenticate a user even though his device 10 broadcasts status messages that are received by terminal 60 and interactive device 105 remains active. This can be done on the basis of a time interval or random basis, e.g. has the user used terminal 60 for more than time limit T8 (Step 1474)? For example any user who uses a terminal 60 in a specific neighborhood Ni may be asked to reauthenticate themselves every 4 hours, while in another neighborhood Nj, they are not asked to reauthenticate themselves.

Reauthentication can include answering a challenge question 1154 properly, providing a biometric indicia to device 10 or to security server 168, or following any other authentication protocols 1153 or 1242 (Step 1462). If the user does not reauthenticate himself within time limit T7 (Step 1464), he will be logged off (Step 1466), and otherwise denied access as indicated in Steps 1468 to 1472, which are not repeated in FIG. 52.

Figure 51:
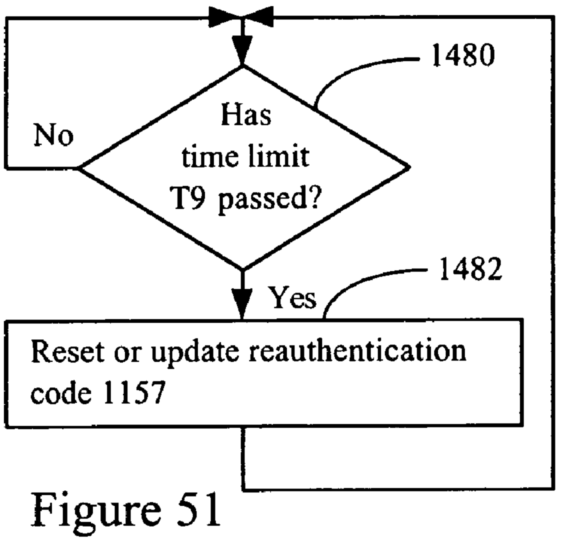
FIG. 51 is a flow chart showing how a reauthentication code can be dynamically updated.

Episodic Updating Reauthentication Code 1157—(FIG. 51)

Reauthentication code 1157 was set when the user was authenticated to security server 168. However, when a period of time is greater than time limit T9 (e.g. 60 seconds) (Step 1480) reauthentication code 1157 can be updated or reset (Step 1482). This ensures that should the user leave, without otherwise logging off computer system 194, that device 10 has the most recent code 1157. This is useful when the time range for reauthentication is set to be relatively short (e.g. 20 minutes) but is generally based on the last time a terminal 60 was used.

Figure 52:
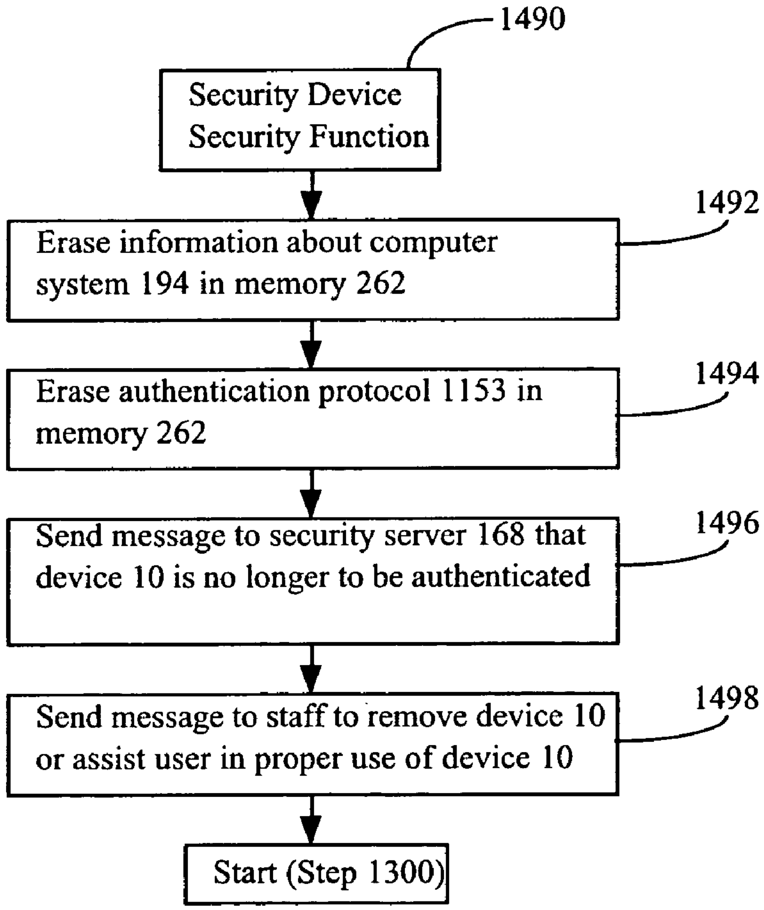
FIG. 52 is a flow chart showing the steps performed as part of a security function.

Security Function 1490—(FIG. 52)

When a user is unable to authenticate himself to device 10 or is unable to do so after trying several times device, 10 can activate a security function designed to protect computer system 194 from someone who may be trying to hack or otherwise guess answer 1155 to challenge question 1154 or attempting to provide a false biometric indicia.

The security function can take a number of different forms, one is to erase all the information about computer system 1162 corresponding to computer system identifier 1202 including authentication protocol 1165 from memory 262 (Step 1492). In other cases device can erase or otherwise prevent from being used device authentication protocol 1153 from memory 262 (step 1494). Additional information can also be erased. When the information is only prevented from being used it can be reset for use by transmitting a special code from terminal 60 to device 10 under the direction of the manager of computer system 194. Presumably this code is limited in distribution or knowledge of to a few trusted computer security staff members who are required to personally verify who the user is that is attempting to use device 10.

The security function can also include terminal 60 sending a message to server 168 that device 10 is no longer to be authenticated (Step 1496). Additional messages (e.g. by e-mail, pager, or phone) can be sent to nearby staff asking them to assist or question the user attempting to use device 10 (Step 1498). An alert can be presented on display 103 and indicator 20 can be activated. An appropriate status 1246 can be entered indicating that device 10 should no longer be authenticated to system 194 until an administrative staff member has spoken to the user or owner of device 10.

Using Device 10 to Activate User Specific Programs

When a user has been authenticated to computer system 194, device 10 may further interact with computer terminal 60. For example device 10 can download from memory 262 to terminal 60 list of specific application programs 1172 or functions the user needs or is allowed to activate or use. This list can be a part of user information 300 (see FIG. 33) e.g. computer system information 1160 and can differ for each computer system identifier 1162. The programs can be indicated by a program name or target address and may further include a disk domain in which the user is to operate the program. When only one program is specified that program can be automatically activated. When more than one is specified, the user is allowed to select which one to activate or use, e.g. as displayed selectable icons.

Each program activated may further require that device 10 provide additional authentication information in addition or in duplication to that provided to computer system 194. In this manner the user is authenticated to the selected program, perhaps using even more secure techniques than required by computer system 194. When a program is activated additional information regarding the user may be provided, e.g. owner name 1146, allowing the program to use this information in order to perform its function.

When the security device 10 is removed from terminal 60 and no longer communicates interrogation responses or status message, any activated programs can be notified or independently determine that the user is not longer present. The activated program can then deactivate or exit its operation. In some cases this will include saving any partial work of the user, e.g. in a folder or disk associated with the user's identity or other information 300 provided by device 10 to the program.

The list of specific programs 1172 a user is allowed to use may also be stored as part of electronic device list 1240 or user list 1250. It is sent from security server 168 to terminal 60 upon receipt of device identifier 1148 from device 10 or the entry of user identifier 1146.

Security Device 10 Ownership and Information 300 Knowledge—

Security device 10 can be owned either by the computer users who uses it. This is especially desirable when security device 10 is used by the user to gain access to several computer systems 194. However, notwithstanding the above statement, security device 10 can be owned by the enterprise or company operating one of the computer systems 194. Whichever party owns the security device 10 is referred to as the owner.

More maximal security, private key(s) 1151 and other valuable information, e.g. biometric reference measurements 1152 or portions of security information 1161, are stored in security device 10 so that they are not accessible outside of security device 10. This can be achieved by using a special security microprocessor for processor 260 and storing the keys in the memory of this processor. Such processors have special guards against external retrieving or detection (e.g. by scanning electron microscopes) of information stored within them. It is further preferred that private key(s) 1151 and other valuable information are not known to the computer user or the owner. The manufacturer of the security device 10 may provide private codes or key(s) 1151 at the time of manufacture in a randomized manner or distribute them in random manner so that the key(s) 1151 or other valuable information cannot be attributed to any specific security badge 10. In some embodiments device identifier 1148 and other information such as security code 1172 can be considered to be a private code.

In some cases the security device 10 may no longer be needed by the computer user and can be reassigned to a second computer user. However, before this can be done any information 300 related to the first computer user should be erased prior to entering in any new information about the second user. This will prevent the second user from accidentally using information that may be attributed to the first computer user. To effect the erasure of information 300 the first computer user may be required to authenticate himself to the security device 10 are previously discussed. Alternately when the security device 10 owner is the enterprise, a security code such as security code 1172 or another one that is used on global basis relative to information 300 can be transmitted to security badge 10. The security badge 10 upon recognition of this code can proceed to erase information 300.

Using Security Device 10 to Decrypt Private Messages—

Security device 10 can be used to decrypt private messages that are only to be read by the computer user having the security device 10. A message may be created and then encrypted using an encryption key, e.g. the public key of a public/private key encryption system or a guarded private key). The message is sent to a person with the security device 10. The message cannot be read by anyone who intercepts the message and cannot be read by the computer user to whom it sent unless they have the security device 10 with the corresponding decryption key (e.g. the private key of a public/private encryption system or a duplicate of the guarded private key). The computer user authenticates himself to the security device 10 as previously described, the security device can then receive the encrypted message or a message digest (e.g. a hash table related to the message). The device then uses the decryption key to decrypt the message or the message digest. When the message is decrypted it can be displayed on display 16 or 258 or it can be transferred to workstation 60 for presentation on display 103. In other cases the decrypted message digest is transferred to workstation 60 which uses the decrypted message digest to further decrypt the encrypted message for presentation on display 103. As is common with well known encryption and decryption methods various safeguards (e.g. checksums, or other verification steps) are used to ensure that the message being decrypted has not been tampered or altered since it was created. In this manner the computer user will be able to rely on the decrypted message as being one and the same as the created message.

Prior to decrypting the message, the user will typically be presented with a notification message on display 103 or 16 or 258 requesting that they activate the security device 10 in some manner (e.g. pressing activation button 18 before the message or message digest will be decrypted. This allows the computer user to control when messages are decrypted. It can be further advantageous to require that the computer user has authenticated himself to badge within a recent time period, e.g. with in 3 minutes. In some cases the user will be asked to authenticate himself to the security device 10 before each message is decrypted.

As a convenience the computer user may indicate to or set the security device 10 to decrypt multiple message with a single activation.

Using Security Device 10 to Sign Multiple Messages—

When several documents are to be signed by the user using security device 10 they can be signed with a single operation. The documents can be presented on display 103 as a summary, e.g. in a table with a title and date for each document, or as a list of subject heading, or the first paragraph of each document can be displayed. A message is displayed on display 103 requesting the user sign the documents and the documents or representative portions of the documents are sent to security device 10. When the user presses activation button 18 each of the documents or representative portions of the documents are digitally signed using encryption key 1151 to create digital signature information. The encrypted data is sent back to the terminal 60 and then to computer system for storage, e.g. with the respective documents when the entire document is not signed. However, the user can request that each document be presented to him prior to signing each of them as previously described.

The invention claimed is:

1. A method for use with a computer system containing information, the method comprising the steps of:

a. providing a separate portable security device for each of a plurality of computer users;

b. providing a terminal including a display screen for presenting information to computer users where the terminal is separate from the portable security devices;

c. communicating system authentication protocol information from at least one of the security devices to the computer system;

d. authenticating the at least one of the security devices with the computer system using the authentication protocol information;

e. upon successful completion of the authenticating step, initiating a first access by the computer user associated with the at least one of the security devices to the computer system via the terminal;
f. creating, sending, and storing a reauthentication code to the at least one of the security devices, where the reauthentication code is related to a time limit;
g. logging the computer user off the terminal; and
h. initiating a second access by the computer user associated with the at least one of the security devices to the computer system via the terminal by communicating the reauthentication code to the computer system from the security device and when the reauthentication code is within the time limit allowing the second access, the step of initiating the second access by the computer user to the computer system further including verifying that the reauthentication code includes a neighborhood identifier that matches a neighborhood identifier of the terminal that the computer user is attempting to use to access the computer system.

2. The method according to claim 1, further including the step of communicating signals generated by the security device to the computer system and when the computer system fails to receive a signal from the security device after a first preset time period the system performing a system security function.

3. The method according to claim 2, further including the step of limiting access to the computer system information as part of performing a system security function.

4. The method according to claim 3, where the step of limiting access includes causing information presented on the terminal display to be removed from the display.

5. The method according to claim 2, where the step of limiting access includes disabling the use of the terminal.

6. The method according to claim 3, further including the step of further limiting access to the computer system after a second preset time period is exceeded.

7. The method according to claim 6 where the step of further limiting access includes logging a user off the computer system.

8. The method according to claim 6, where the step of initiating either a first or second access by the computer user includes recording in a database that the computer user is using the terminal and the step of further limiting access includes removing from the database that the computer user is using the terminal.

9. The method according to claim 1, where the reauthentication signal is validated by at least one of the terminal which is proximal to the security device and the computer system.

10. The method according to claim 9, further including the step of comparing a time component of the reauthentication signal and the current time and determining that the current time is within a specified time limit of the time component.

11. The method according to claim 10, including the step of when the current time is not within a specified time limit requiring the security device be authenticated with the computer system by communicating the system authentication protocol information from the security device to the computer system.

12. The method according to claim 11, wherein prior to the step of authenticating the security device with the computer system, the method further includes the step of authenticating the computer user to the security device by the computer user providing response information to the security device selected from the list of a response to a question and a biometric indicia, and wherein the provided response information must match device authentication protocol information stored in the security device prior to authenticating the security device with the computer system.

13. The method according to claim 12 wherein, when biometric indicia is provided, the indicia is provided by the computer user using a biometric sensor in the security device to sense the indicia.

14. The method according to claim 12, further including the step of incrementing a count in the security device when the computer user is not authenticated to the security device, the count recording the inability of the security device to authenticate the computer user.

15. The method according to claim 14, further including the step of activating a security device security function selected from the list of (i) erasing a portion of the memory of the security device, (ii) transmitting an alert message to the computer system, and (iii) disabling the security device, when the count exceeds a limit.

16. The method according to claim 15, including the step of storing the count in the memory of the security device.

17. The method according to claim 16, further including the step of resetting the count to zero when the count is less than or equal to a limit and the computer user is able to authenticate himself to the security device.

18. The method according to claim 1, further including the step of receiving a computer system identifier by the security device and positively matching the received system identifier to a trusted computer system identifier prior to authenticating the security device to the computer system.

19. A method for use with a computer system containing information, the method comprising the steps of:
a. providing a terminal including a display screen for presenting information to the computer user where the terminal is separate from the security device;
b. communicating system authentication protocol information from the security device to the computer system;
c. authenticating the security device with the computer system using the authentication protocol information;
d. upon successful completion of the authenticating step, initiating a first access by the computer user to the computer system via the terminal;
e. storing a reauthentication code in the computer system and associating the code with user identification information associated with the computer user;
f. logging the computer user off the computer system;
g. initiating a second access between the computer system and the computer user via the terminal by using the security device to communicate at least a portion of system authentication protocol information to the computer system, the computer system determining that access is to be provided by using the at least a portion of system authentication protocol information to retrieve the reauthorization code and determining that the code allows access, where the step of initiating the second access is only performed when the reauthentication code includes a neighborhood identifier that matches a neighborhood identifier of the terminal the computer user is attempting to use to access the computer system; and
h. the security device receiving a computer system identifier and positively matching the computer system identifier to a trusted computer system identifier prior to authenticating the security device with the computer system.

20. The method according to claim 19, further including the step of communicating signals generated from the security device to the computer system and when the computer system fails to receive a signal from the security device after a first preset time period the system performing a system security function.

21. The method according to claim 20, where performing a system security function includes limiting access to the computer system information via the terminal.

22. The method according to claim 21, where the step of limiting access includes causing information presented on the terminal display to be removed from the display.

23. The method according to claim 20, where the step of limiting access includes disabling use of the terminal.

24. The method according to claim 21, where after a second preset time period the computer system further limiting access to the computer system.

25. The method according to claim 24 where the step of further limiting access includes logging a user off the terminal.

26. The method according to claim 24, further including the step of entering in a database that the computer user is using the terminal when access is to computer system is initiated and wherein the step of further limiting access includes removing from the database that the computer user is using the terminal.

27. The method according to claim 19, further including the step of determining that the reauthentication code includes a time component and the step of determining that the reauthentication code allows access includes comparing the time component to the current time to determine that a specified time limit has not been exceeded.

28. The method according to claim 27, including the step of authenticating the security device with the computer system by communicating system authentication protocol information from the security device to the computer system when the current time is not within the specified time limit.

29. The method according to claim 19, further including the step authenticating the computer user to the security device by the computer user providing information to the security device selected from the list of a response to a question and a biometric indicia, and wherein the provided information must match device authentication protocol information stored in the security device prior to authenticating the security device with the computer system.

30. The method according to claim 29 wherein, when biometric indicia is provided, the indicia is provided by the computer user using a biometric sensor in the security device to sense the indicia.

31. The method according to claim 29, further including the step of incrementing a count in the security device when the computer user is not authenticated to the security device, the count recording the inability of the security device to authenticate the computer user.

32. The method according to claim 31, further including the step of activating a security device security function selected from the list including (i) erasing a portion of the memory of the security device,(ii) transmitting an alert message to the computer system, and (iii) disabling the security device when the count exceeds a limit.

33. The method according to claim 32, including the step of storing the count in the memory of the security device.

34. The method according to claim 33, further including the step of resetting the count to zero when the count is less than or equal to a limit and the computer user is able to authenticate himself to the security device.

35. A method of initiating access between a computer user having a security device and a computer system containing information, the method comprising the steps of:

a. providing a first terminal including a display screen for presenting information to the computer user where the first terminal is separate from the security device;

b. communicating system authentication protocol information from the security device to the computer system at a first time;

c. authenticating the security device with the computer system using the authentication protocol information;

d. upon successful completion of the authenticating step, initiating a first access by the computer user to the computer system via the first terminal;

e. creating and storing a reauthentication code that is related to a time limit;

f. logging the computer user off the first terminal;

g. facilitating a second access by the computer user to the computer system via the first terminal using the reauthentication code at a second time that is within the time limit;

h. providing a second terminal where a neighborhood terminal is selected from a list including the first terminal and the second terminal;

i. presenting the security device at the neighborhood computer terminal and obtaining the authentication code at a third time subsequent to the second time;

j. determining that the third time is subsequent to the time limit; and k. where the third time is subsequent to the time limit, granting access to the computer system only after the user provides authentication protocol information via the neighborhood computer terminal and the provided information is matched to stored system authentication protocol information.

36. The method of claim 35 wherein the terminal is a first terminal and the method further includes providing a second terminal including a second display screen for presenting information to the computer user where the second terminal is separate from the security device, the first and second terminals in a common neighborhood of the computer system and wherein the step of initiating a first access to the computer system at the first time includes using the first terminal to obtain authentication protocol information and the step of facilitating a second access includes using the second terminal to obtain the reauthentication code.

37. The method of claim 35 wherein the security device is an externally powered electronic device.

38. The method of claim 36, wherein each of the first and second terminals includes at least one of a card reader, electrical contacts, radio frequency identification antenna, an infrared transceiver and a bar code reader.

39. The method of claim 36, wherein the step of facilitating a second access includes bringing the security device proximate to the second terminal so as to contact the terminal.

40. The method of claim 35 wherein step of communicating system authentication protocol information includes the step of providing a user identifier and a password.

41. The method of claim 35 wherein step of communicating system authentication protocol information includes providing a user biometric indicia.

42. The method of claim 35 wherein the step of facilitating a second access includes initiating a second access by the computer user to the computer system via the terminal by communicating the reauthentication code to the computer system from the security device and when the reauthentication code is within the time limit allowing the second access.

43. The method of claim 35 wherein the reauthentication code is stored by the computer system.

44. The method of claim 43 wherein the reauthentication code is associated with a security device identifier within the computer system.

45. The method of claim 35 wherein the security device must be proximate to the terminal to communicate with the computer system.

46. The method of claim 1 wherein the security device is an externally powered electronic device.

47. The method of claim 19 wherein the security device is an externally powered electronic device.

* * * * *